(12) United States Patent
Chung et al.

(10) Patent No.: US 9,610,370 B2
(45) Date of Patent: Apr. 4, 2017

(54) COMPOSITIONS AND METHODS FOR TUMOR IMAGING AND TARGETING BY A CLASS OF ORGANIC HEPTAMETHINE CYANINE DYES THAT POSSESS DUAL NUCLEAR AND NEAR-INFRARED PROPERTIES

(71) Applicants: Leland W. K. Chung, Beverly Hills, CA (US); Dongfeng Pan, Charlottesville, VA (US)

(72) Inventors: Leland W. K. Chung, Beverly Hills, CA (US); Dongfeng Pan, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 28 days.

(21) Appl. No.: 14/350,194

(22) PCT Filed: Oct. 5, 2012

(86) PCT No.: PCT/US2012/058917
§ 371 (c)(1),
(2) Date: Apr. 7, 2014

(87) PCT Pub. No.: WO2013/052776
PCT Pub. Date: Apr. 11, 2013

(65) Prior Publication Data
US 2014/0248213 A1    Sep. 4, 2014

Related U.S. Application Data

(60) Provisional application No. 61/544,915, filed on Oct. 7, 2011, provisional application No. 61/605,360, filed on Mar. 1, 2012.

(51) Int. Cl.
| | | |
|---|---|---|
| A61K 51/00 | (2006.01) | |
| A61M 36/14 | (2006.01) | |
| A61K 51/04 | (2006.01) | |
| A61K 49/00 | (2006.01) | |
| C07B 59/00 | (2006.01) | |
| C09B 23/01 | (2006.01) | |
| C09B 23/08 | (2006.01) | |
| A61B 5/00 | (2006.01) | |
| A61B 6/00 | (2006.01) | |
| A61K 49/04 | (2006.01) | |

(52) U.S. Cl.
CPC ........ *A61K 51/0482* (2013.01); *A61B 5/0035* (2013.01); *A61B 5/0075* (2013.01); *A61B 6/481* (2013.01); *A61K 49/0032* (2013.01); *A61K 49/0034* (2013.01); *A61K 49/0438* (2013.01); *A61K 51/0446* (2013.01); *C07B 59/002* (2013.01); *C09B 23/0016* (2013.01); *C09B 23/0066* (2013.01); *C09B 23/086* (2013.01); *A61K 51/0474* (2013.01)

(58) Field of Classification Search
None
See application file for complete search history.

(56) References Cited

U.S. PATENT DOCUMENTS

| | | | | |
|---|---|---|---|---|
| 5,453,505 A | * | 9/1995 | Lee | A61K 49/0032 435/4 |
| 6,534,041 B1 | * | 3/2003 | Licha | A61K 49/0032 424/1.11 |
| 6,593,148 B1 | * | 7/2003 | Narayanan | C07D 209/12 435/6.12 |
| 7,700,258 B2 | | 4/2010 | Kasperchik | |
| 2004/0141920 A1 | * | 7/2004 | Achilefu | A61K 41/0033 424/9.6 |
| 2004/0223913 A1 | * | 11/2004 | Achilefu | A61K 31/403 424/9.6 |
| 2007/0015092 A1 | * | 1/2007 | Gore | B41M 5/3333 430/332 |
| 2010/0040547 A1 | | 2/2010 | Frangioni | |

FOREIGN PATENT DOCUMENTS

| | | | | |
|---|---|---|---|---|
| DE | WO 2007088129 A2 | * | 8/2007 | ......... A61K 49/0032 |
| EP | 1815870 A1 | | 8/2007 | |
| JP | 2008133458 A | | 6/2008 | |
| WO | WO-0016810 | | 3/2000 | |
| WO | WO-2005019247 | | 3/2005 | |
| WO | WO-2007088129 | | 8/2007 | |
| WO | WO-2009152440 | | 12/2009 | |
| WO | WO-2013052776 | | 4/2013 | |

OTHER PUBLICATIONS

Hilderbrand et al. (Bioconj. Chem. 2005, 16, 1275-1281).*
Parker (Chem. Soc. Rev. 1990, 19, 271-291).*
Chipon, Bertrand, "Synthesis and post-synthetic derivatization of a cyanine-based amino acid. Application to the preparation of a novel water-soluble NIR dye", Tetrahedron Letters, 47, (2006), 8279-8284.
Hilderbrand, Scott A, "Monofunctional Near-Infrared Fluorochromes for Imaging Applications", Bioconjugate Chem, 16, (2005), 1275-1281.
"New Indane Contain Compound Radioisotope Label Dye Radioactive Pharmaceutical", DataBase WPI Week 200868, Thomson Scientific, XP002741309, 2 pgs, 2016.
Yang, Xiaojian, "Near IR Heptamethine Cyanine Dye-Mediated Cancer Imaging", Clinical Cancer Research, 16, (2010), 2833-2845.

* cited by examiner

*Primary Examiner* — Michael G Hartley
*Assistant Examiner* — Melissa Perreira
(74) *Attorney, Agent, or Firm* — Rodney L. Sparks

(57) ABSTRACT

The present invention provides for heptamethine cyanine dyes that possess both nuclear and near-infrared imaging capabilities. These dyes can be used for imaging, targeting and detecting tumors in patients.

2 Claims, 12 Drawing Sheets

T-half=256.9±13.2min (n=3 tumor mice), calibrated separated from T-half of three mice and averaged FIG. 12A-B
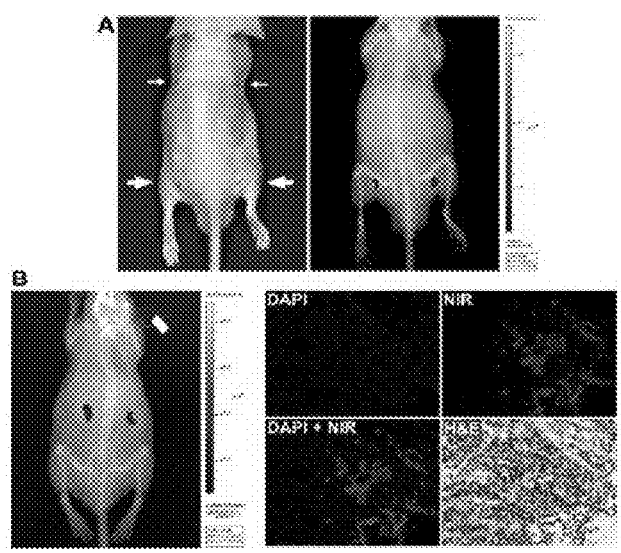
FIG. 13 A-C
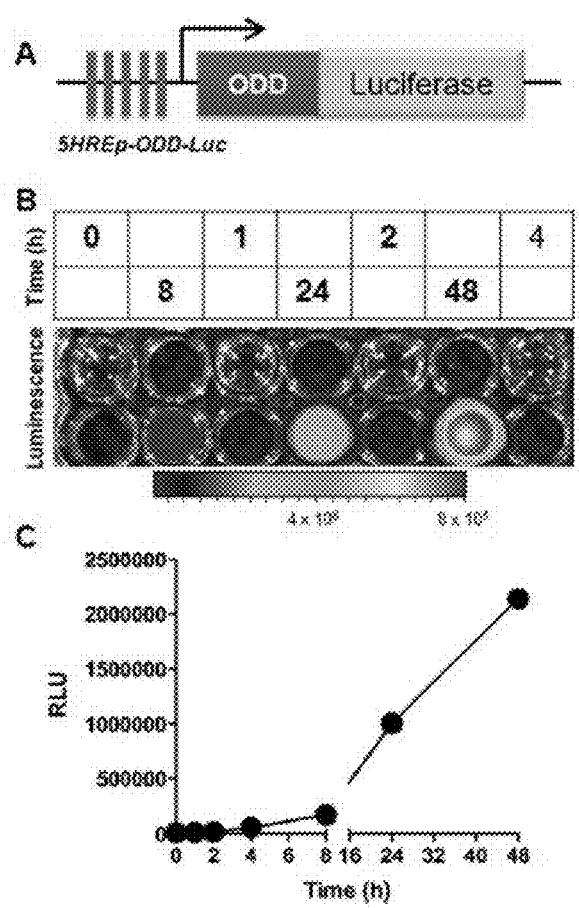

FIG. 14
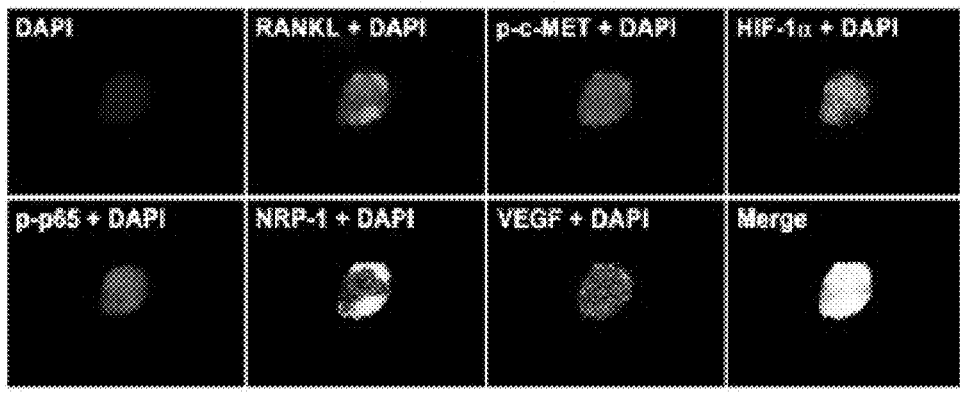
FIG. 15
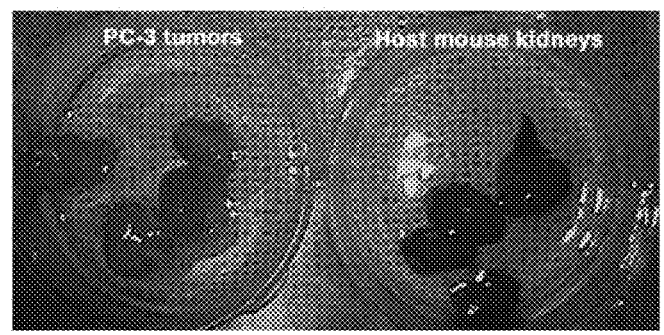
FIG. 16A-D
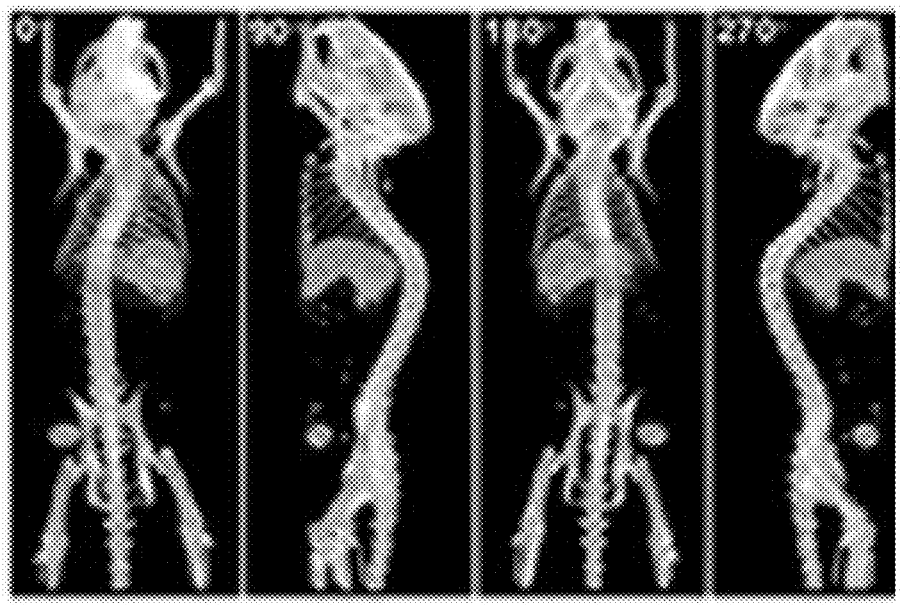

FIG. 17A-B
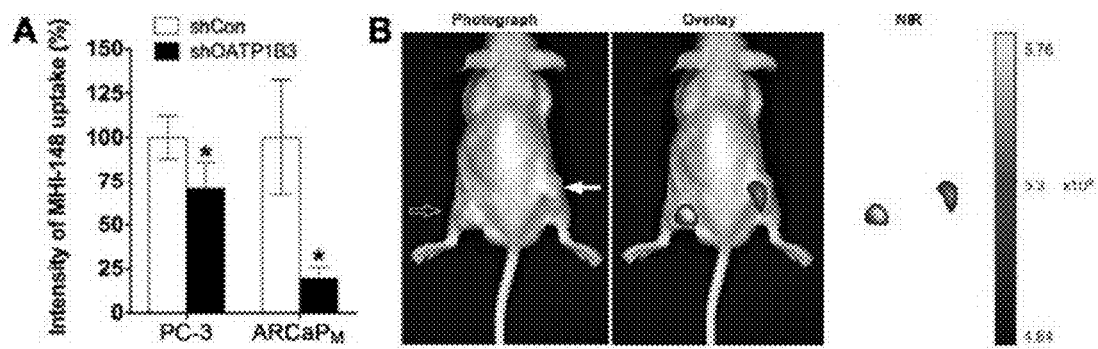
FIG. 18A-B
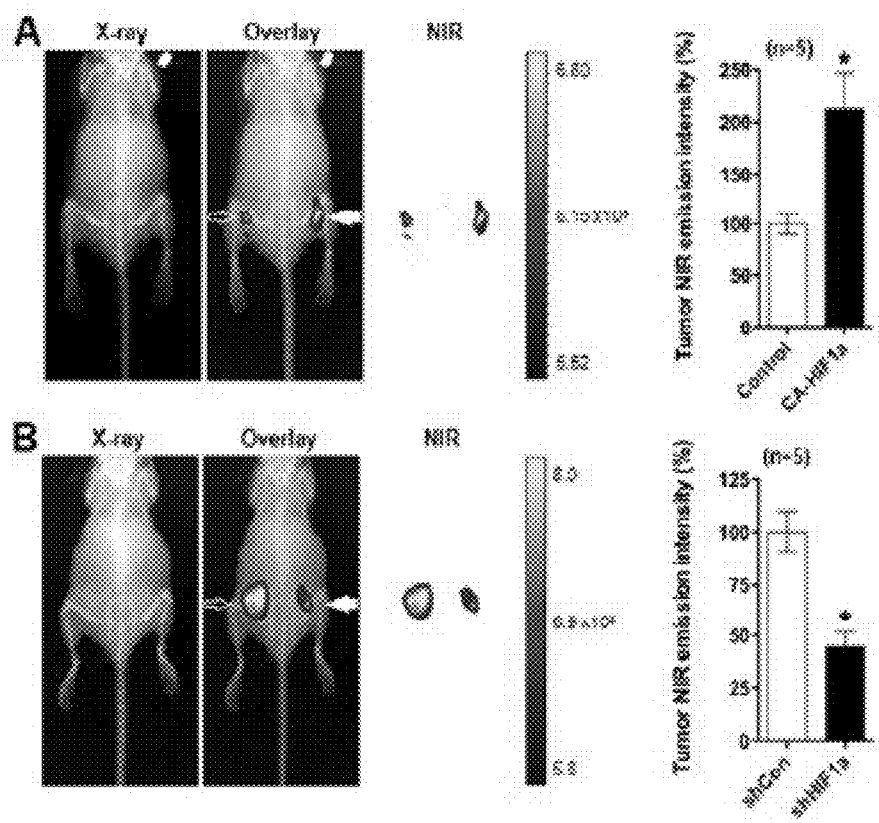

FIG. 20

|       | OATP1B3          | OATP2B1            | OATP5A1              |
|-------|------------------|--------------------|----------------------|
| PrEC  | 1.000 ± 0.196    | 1.000 ± 0.690      | 1.000 ± 0.342        |
| P69   | 0.023 ± 0.002    | 26.165 ± 7.856     | 1.134 ± 0.376        |
| PC-3  | 19.644 ± 4.359   | 1.458 ± 0.948      | 57.886 ± 12.795      |
| PC-3M | 41.820 ± 13.786  | 709.742 ± 233.670  | 1240.858 ± 607.955   |

COMPOSITIONS AND METHODS FOR TUMOR IMAGING AND TARGETING BY A CLASS OF ORGANIC HEPTAMETHINE CYANINE DYES THAT POSSESS DUAL NUCLEAR AND NEAR-INFRARED PROPERTIES

CROSS REFERENCE TO RELATED APPLICATIONS

This application is a national stage filing of International Application No. PCT/US2012/058917, filed Oct. 5, 2012, which claims benefit under 35 U.S.C. §119(e) of U.S. Provisional Patent Application Ser. No. 61/544,915 filed Oct. 7, 2011, and U.S. Provisional Patent Application Ser. No. 61/605,360 filed Mar. 1, 2012.

FIELD OF INVENTION

This invention relates to heptamethine cyanine dyes that possess both nuclear and near-infrared imaging capabilities, for imaging, targeting, detecting and treating tumors.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer mortality and morbidity can be greatly improved by the development of effective imaging and targeting agents. Many of the biomarkers adopted today for disease detection has been laborious and not cost-effective. In the case of prostate cancer, it remains controversial if screening for serum prostate-specific antigen (PSA) can effectively save lives (Schröder et al. 2009; Andriole et al. 2009). In a more recent study, Schröder et al. (Schröder et al. 2009) concluded that "to prevent one prostate-cancer death, 1410 men (or 1068 men who actually underwent screening) would have to be screened, and an additional 48 men would have to be treated". The ineffectiveness of screening for the presence of cancers in men justifies the development of more effective imaging and targeting agents, that can detect tumor earlier, follow tumor images in patients more reliably, and if necessary, treat cancer patients earlier to regress tumors when they are still small at the primary or at metastatic sites. This has not been achieved because of the barriers encountered in the imaging and targeting of cancers, due to tumor cell heterogeneity.

The area of developing more effective imaging and targeting agents is therefore considered as unmet medical need.

SUMMARY OF THE INVENTION

The present invention describes a class of dual imaging and targeting heptamethine cyanine dyes that possess both nuclear and near-infrared (NIR) properties, referred herein as Dual Nuclear/NIR Agents, for improved cancer diagnosis, prognosis and treatment.

The Dual Nuclear/NIR Agents of the present invention are represented by the formulas:

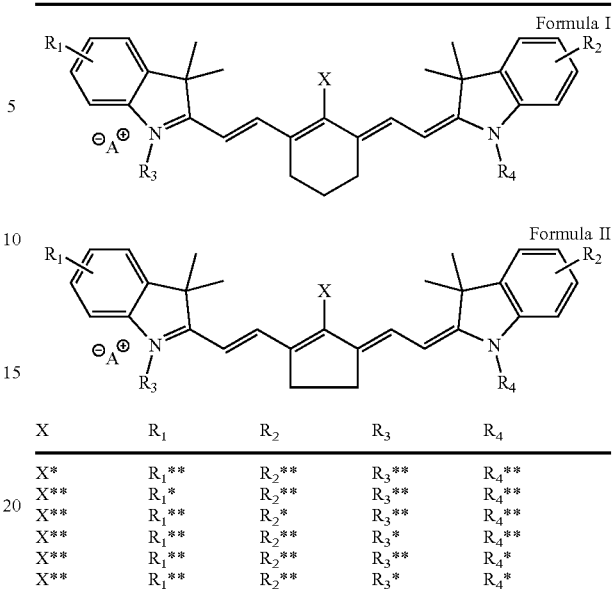

| X | $R_1$ | $R_2$ | $R_3$ | $R_4$ |
|---|---|---|---|---|
| X* | $R_1$** | $R_2$** | $R_3$** | $R_4$** |
| X** | $R_1$* | $R_2$** | $R_3$** | $R_4$** |
| X** | $R_1$** | $R_2$* | $R_3$** | $R_4$** |
| X** | $R_1$** | $R_2$** | $R_3$* | $R_4$** |
| X** | $R_1$** | $R_2$** | $R_3$** | $R_4$* |
| X** | $R_1$** | $R_2$** | $R_3$* | $R_4$* |

$R_1$ and $R_2$ can each be independently selected from the group consisting of radioisotopes I-125, I-123, I-131, I-124, F-18, hydrogen, sulfonato, any electron withdrawing group (EWG), and electron donating group (EDG), and can be independently attached at the various aromatic ring positions such as 3,3', 4,4', 5,5', 6,6';

$R_3$ can be selected from the group consisting of hydrogen, alkyl, aryl, aralkyl, ω-sulfonatoalkyl, ω-carboxylate-alkyl, ω-aminoalkyl, ω-amoniumalkyl, alkylsulfonato, alkylcarboxylic, alkylamino, ω-alkylaminium, ω-alkynyl, PEGyl, ω-carboxylate-PEGyl, ω-amoniumPEGyl, ω-aminoPEGyl PEGylcarboxylate, ω-PEGylaminium, PEGylamino, ω-PEGylalkynyl, ω-acyl-O-CT, and ω-PEGylcarboxyl-O-CT;

$R_4$ can be selected from the group consisting of hydrogen, alkyl, aryl, aralkyl, alkylsulfonato, alkylcarboxylic, alkylamino, ω-alkylaminium, ω-alkynyl, PEGyl, PEGylcarboxylate, ω-PEGylaminium, ω-acyl-NH—CR, ω-acyl-lysine-CR, ω-acyl-triazole-CR, ω-PEGylcarboxyl-NH—CR, ω-PEGylcarboxyl-lysine-CR, and ω-PEGylcarboxyl-triazole-CR;

X can be selected from the group consisting of a hydrogen, halogen, I-125, I-123, I-131, I-124, F-18, CN, Me, OH, 4-O-Ph-CH$_2$CH$_2$COOH, 4-O-Ph-NH—CR, NH—CR, 4-S-Ph-NH—CR, ω-iminoacyl-NH—CR, ω-aminoacyl-lysine-CR, ω-iminoacyl-triazole-CR, 4-O-Ph-CH$_2$CH$_2$COOCT, 4-O-Ph-O-CT, 4-S-Ph-O-CT, and ω-iminoacyl-O-CT;

CR can be selected from the group consisting of a metal chelating agent, a radioactive or nonradioactive metal complex, a radioiodine or iodine labeled Bolten-Hunter reagent, and a radioiodine or iodine labeled tyrosine moiety;

the metal can be selected from the group consisting of Cu-64, In-111, Tc-99m, Ga-68, Y-90, Lu-177, Re-188, At-211, Bi-213, Ac-225 and their nonradioactive counterparts;

CT can be selected from the group consisting of radiolabeled or non-radiolabeled cytotoxic drugs, antibodies, toxins, aptamers, siRNA, antisense constructs and microRNAs; and counteranion A can be selected from the group consisting of iodide, bromide, arylsulfonato, alkylsulfonato, tetrafluoroborate, chloride, and any pharmaceutically acceptable anions;

each of X*, $R_1$*, $R_2$*, $R_3$*, and $R_4$* refers to the radioactive substitutes selected from their counterpart group of X, $R_1$, $R_2$, and $R_4$, and X, $R_1$, $R_2$, $R_3$ and $R_4$** refers to the non-radioactive moieties.

The present invention also provides pharmaceutically acceptable salts of the compounds of the invention.

The present invention also provides radiopharmaceutical formulations or compositions.

BRIEF DESCRIPTION OF THE FIGURES

Exemplary embodiments are illustrated in referenced figures. It is intended that the embodiments and figures disclosed herein are to be considered illustrative rather than restrictive.

FIGS. 12A-B shows the uptake of a representative NIR dye, PC-001, by freshly obtained renal cancer tissues with results confirmed at the cellular level by fluorescence confocal microscopy. All images are shown at ×200 magnification.

FIGS. 13A-C illustrate the application of the degradable luciferase to sense hypoxic condition. FIG. 13A shows the construct of a recombinant luciferase (Luc) that is fused with an oxygen-dependent domain (ODD) for rapid degradation in normoxia. Under hypoxic conditions the hypoxia responsive elements (HRE) in tandem elicit a production of the Luc, stable due to reduced degradation of this protein because of the lack of oxygen. FIG. 13B shows a tagged PC-3 clone showed a time-dependent enhanced Luc activity specifically under hypoxic conditions. Note marked increased Luc activity in PC-3 cells exposed to hypoxia >8 hrs. FIG. 13C shows biochemical assays confirmed the marked activation of Luc activity between 8-48 hrs under hypoxia.

FIG. 14 illustrates mQDL characterization of gene expression in CTCs of Pca patients. Periphery blood samples of PCa patients were used to isolate CTCs based on NIR staining and EpCAM marker expression.

FIG. 15 shows that PC-3 tumors yield stronger emission than that of the normal mouse kidneys.

FIGS. 16A-D illustrate PET imaging of xenograft prostate tumors. Cu-DOTA-NIR dye (FIG. 16A) was shown to be uptaken and retained in a tumor xenograft with a small amount (<20%) of the 64Cu tracer demetalated and retained in the host liver (FIG. 16B).

FIGS. 17A-B illustrate the involvement of OATP1B3 in mediating carbocyanine dye uptake in PCa cells. Human PCa cells, PC-3 and ARCaPM, when subjected to genetic knockdown of OATP1B3 (shOTP1B3), uptake less PC-001 when copared to vector controls (shCon, FIG. 17A). This reduced uptake correlated directly with the efficiency of OATP1B3 knockdown. FIG. 17B shows 1B3 knockdown PC-3 cells grown as tumor xenografts in mice. Similar studies were conducted by upregulating OATP1B3 by genetically transfecting PC-3 cells with constitutively active HIF1α, which increased PC-001 uptake and OATP1B3 protein in PC-3 tumors.

FIGS. 18A-B illustrate the involvement of HIF1α in mediating carbocyaninie dye uptake in PCa cells. Steady-state level of expression of the HIF1α in PC-3 human PCa cell line was manipulated by either upregulate HIG1a through gene transfection (Constituvely active HIF1α, or CA-HIF1α, FIG. 18A) or downregulate HIF1α through shRNA treatment (FIG. 18B). These manipulations resulted in respectively either increased or decreased PC-001 uptake by PC-3 tumors in mice. Data are expressed as average +/−SEM of 5 mice per group.

FIG. 20 summarizes the relative expression levels of three OATPs, 1B3, 2B1 and 5A1 in normal and cancerous prostate epithelial cells

DETAILED DESCRIPTION OF THE INVENTION

Figure 1:
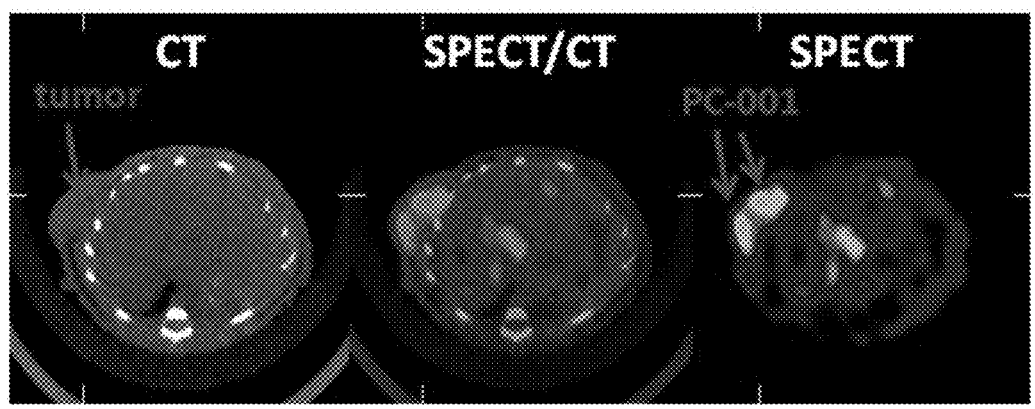
FIG. 1 depicts the SPECT/CT image of PC-001 with a nude mouse model of a human breast cancer MCF-7 xenograft in accordance with various embodiments of the present invention. PC-001 (3.82 mCi) was formulated in 2% of tween 80 (diluted with saline) and injected via tail vein. SPECT/CT scan was performed at 20 h post injection.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001), and March, *Advanced Organic Chemistry Reactions, Mechanisms and Structure* $5^{th}$ ed., J. Wiley & Sons (New York, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, the terms "alkyl," "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and can have from 3 to 10 ring carbon atoms. Exemplary cyclic groups include cyclopropyl, cyclopentyl, cyclohexyl, cyclopropylmethyl, adamantly, norbornane, and norbornene. This is also true of groups that include the prefix "alkyl-," such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylacohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

These may be straight chain or branched, saturated or unsaturated aliphatic hydrocarbon, which may be optionally inserted with N, O, or S. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

As used herein, the term "alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, the term "alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Alkoxy" refers to an —OR group, wherein R is alkyl or substituted alkyl, preferably C1-C20 alkyl (e.g., methoxy, ethoxy, propyloxy, benzyloxy, etc.), most preferably C1-C7.

"PEGyl" refers to a polyethylene chain with repeated moiety of (—$CH_2$—$CH_2$—O—)$_n$. n is ranging from 2 to 20. The remote end of the PEG is functionalized with amino, carboxylate, sulfonate, alkyne, sulfohydryl, hydroxyl, or any other functional group to enhance hydrophilicity or allow conjugation with radiometal chelators or other radiolabeled prosthetic compounds.

"CR" refers to a complex of a radiometal and its chelator or a radiolabeled prosthetic group.

"Radiometal or radioisotope" refers to a positron or gamma emitter for imaging application or a beta or alpha emitter for therapy application. Exemplary radioisotopes include, but are not limited to, I-125, I-123, I-131, I-124, F-18, Cu-64, In-111, Tc-99m, Ga-68, Y-90, Lu-177, Re-188, At-211, Bi-213, Ac-225, and the like.

"CT" refers to the group consisting of radiolabeled or non-radiolabeled cytotoxic drugs, antibodies, toxins, aptamers, siRNA, antisense constructs and microRNAs.

"Non-interfering substituents" are those groups that, when present in a molecule, are typically non-reactive with other functional groups contained within the molecule.

The term "substituted" as in, for example, "substituted alkyl" refers to a moiety (e.g., an alkyl group) substituted with one or more non-interfering substituents, such as, but not limited to: C3-C8 cycloalkyl, e.g., cyclopropyl, cyclobutyl, and the like; halo, e.g., fluoro, chloro, bromo, and iodo; cyano; alkoxy; phenyl; substituted phenyl; and the like.

"Aryl" as used herein includes carbocyclic aromatic rings or ring systems. As used herein, the term "aryl" refers to an aromatic 5-8 membered monocyclic, 8-12 membered bicyclic, or 11-14 membered tricyclic ring system. Examples of aryl groups include phenyl, naphthyl, biphenyl, fluorenyl and indenyl.

"Substituted aryl" is aryl having one or more non-interfering groups as a substituent. For substitutions on a phenyl ring, the substituents may be in any orientation (i.e., ortho, meta, or para).

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen. Multiple rings may be fused, as in quinoline or benzofuran. Particularly preferred heterocycle groups are 5-10 membered rings with 1-3 heteroatoms selected from O, S, and N.

"Substituted heterocycle" is a heterocycle having one or more side chains formed from non-interfering substituents.

"Heteroaryl" is an aryl group containing from one to four N, O, or S atoms(s) or a combination thereof, which heteroaryl group is optionally substituted at carbon or nitrogen atom(s) with C1-6 alkyl, —$CF_3$, phenyl, benzyl, or thienyl, or a carbon atom in the heteroaryl group together with an oxygen atom form a carbonyl group, or which heteroaryl group is optionally fused with a phenyl ring.

Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1, 2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. Particularly preferred heteroaryl groups are 5-10-membered rings with 1-3 heteroatoms selected from O, S, and N.

"Substituted heteroaryl" refers a heteroaryl having one or more non-interfering groups as substituents.

Each of the terms "drug," "biologically active molecule," "biologically active moiety," "active agent" and "biologically active agent", when used herein, means any substance which can affect any physical or biochemical properties of a biological organism, including but not limited to viruses, bacteria, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of an agent and/or conjugate of the invention present in a pharmaceutical preparation that is needed to provide a desired level of active agent and/or conjugate in the bloodstream or in the target tissue. The precise amount will depend upon numerous factors, e.g., the particular active agent, the components and physical characteristics of the pharmaceutical preparation, intended patient population, patient considerations, and the like, and can readily be determined by one skilled in the art, based upon the information provided herein and available in the relevant literature.

The term "prodrug" refers to a compound that formulated as a precursor compound that, following administration, activates or releases the active component of the compound in vivo via a chemical or physiological process (e.g., upon being brought to physiological pH or through enzyme activity). A discussion of the synthesis and use of prodrugs is provided by Higuchi and Stella, Prodrugs as Novel Delivery Systems, vol. 14 of the ACS Symposium Series, and Bioreversible Carriers in Drug Design, ed. Edward B. Roche, American Pharmaceutical Association and Pergamon Press, 1987. Accordingly, the term "prodrug" refers to compounds that can be converted via some chemical or physiological process (e.g., enzymatic processes and metabolic hydrolysis) to an inactive form that can be activated in vivo by some co-compound or a specific environmental condition, e.g., pH etc. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject.

An "active metabolite" is a physiologically active compound which results from the metabolism of a compound of the invention, or a prodrug thereof, when such compound or prodrug is administered to a mammal.

"Polypeptide" or "poly(amino acid)" refers to any molecule comprising a series of amino acid residues, typically at least about 5-20 residues, linked through amide linkages (also referred to as peptide linkages) along the alpha carbon backbone. While in some cases the terms may be used synonymously herein, a polypeptide is a peptide typically having a molecular weight up to about 10,000 Da, while peptides having a molecular weight above that are commonly referred to as proteins. Modifications of the peptide side chains may be present, along with glycosylations, hydroxylations, and the like. Additionally, other non-peptidic molecules, including lipids and small drug molecules, may be attached to the polypeptide. The polypeptide may comprise any combination or sequence of amino acid residues. The polymers of the invention are suitable for covalent attachment to both polypeptides and proteins.

"Amino acid" refers to organic acids containing both a basic amine group and an acidic carboxyl group. The term encompasses essential and non-essential amino acids and both naturally occurring and synthetic or modified amino acids. The most common amino acids are listed herein by either their name or by the three letter or single letter abbreviations: Glycine (Gly, G), Alanine (Ala, A), Valine (Val, V), Leucine (Leu, L), Isoleucine (Ile, I), Methionine (Met, M), Proline (Pro, P), Phenylalanine (Phe, F), Tryptophan (Trp, W), Serine (Ser, S), Threonine (Thr, T), Asparagine (Asn, N), Glutamine (Gln, Q), Tyrosine, (Tyr, Y), Cysteine (Cys, C), Lysine (Lys, K), Arginine (Arg, R), Histidine (His, H), Aspartic Acid (Asp, D), and Glutamic acid (Glu, E).

By "residue" is meant the portion of a molecule remaining after reaction with one or more molecules. For example, an amino acid residue in a polypeptide chain is the portion of an amino acid remaining after forming peptide linkages with adjacent amino acid residues.

"Electron withdrawing group" or EWG refers to functional groups that remove electron density from the ring by making it less nucleophilic. This class can be recognized by the atom adjacent to the π system having several bonds to more electronegative atoms or the presence of a formal charge. Examples of these groups include halogens, aldehydes, ketones, esters, carboxylic acids, acid chlorides, nitriles, nitrosos, and sulfonic acids.

"Electron donating group" or EDG refers to functional groups that add electron density to the ring by making it more nucleophilic. This class can be recognized by lone pairs on the atom adjacent to the π system. Examples of these groups include alkyl, alkenyl, alkynyl, amides, ethers, alkoxides, alcohols, and amines.

The term "patient," refers to a living organism suffering from or prone to a condition that can be prevented or treated by administration of an agent, and includes both humans and animals.

"Optional" or "optionally" means that the subsequently described circumstance may or may not occur, so that the description includes instances where the circumstance occurs and instances where it does not.

The present invention describes a class of dual imaging and targeting heptamethine cyanine dyes that possess both nuclear and near-infrared (NIR) properties, referred herein as Dual Nuclear/NIR Agents, for improved cancer diagnosis, prognosis and treatment. The application of Dual Nuclear/NIR Agents, for cancer imaging and targeting could have important implications in personalized oncology and medicine because these series of agents could detect tumors in preclinical animal models with high degree of precision, sensitivity and reliability when compared with the current gold standard, [18F]-fluorodeoxyglucose ([18F]FDG). [18F]FDG, a PET imaging tracer, has been widely used in oncology based on the well-known mechanism of increased glucose transport and utilization, by cancer cells. Unlike [18F]FDG, the uptake mechanism of Dual Nuclear/NIR Agents is thought to be energy-dependent, which relies upon the differential expression of a series of organic anion transporter peptides between cancer and normal cells (Yang et al. 2010). The present invention is superior to [18F]FDG in that Dual Nuclear/NIR Agents are both imaging and targeting agents and can image cancer cells regardless of their basal metabolic status. One added advantage is that Dual Nuclear/NIR Agents can be chemically modified to possess cytotoxicities against tumor cell growth. By tracking the pharmacokinetics and pharmacodynamics of the Dual Nuclear/NIR Agents, the inventors anticipate that the present invention can provide sensitive and specific agents to support surgeons, oncologists, pathologists and laboratory medicine personnels, on a real-time basis, for the early detection of cancers in patients, and for the eradication of pre-existing tumor cells in patients.

In summary, in comparison to [18F]FDG, Dual Nuclear/NIR Agents have the following advantages: 1) Unlike [18F]FDG which is not a cancer-specific tracer and it cannot differentiate between cells that have a high metabolic rate associated with neoplasia, and those for which the increased metabolic rate is associated with other etiologies, such as infection or inflammation, Dual Nuclear/NIR Agents are specific for cancer and not normal cells irrespective of the metabolic status of the cells; and 2) Dual Nuclear/NIR Agents can be readily modified chemically to become cytotoxic agents targeting cancer but not normal cells, while [18F]FDG is more difficult and less likely due to its uptake by both normal and tumor tissues. In comparison to other imaging agents developed for cancer imaging, the Dual Nuclear/NIR Agents have the advantage of being broad spectrum cancer-specific regardless of the cancer types. In a recent publication (Yang et al. 2010), one of the inventor's group reported that several other heptamethine cyanine dyes were uptaken by cancer cells and tissues across the animal species; for example, mouse and human. This advantage can be of great importance due to the well-recognized problem of imaging or targeting tumors due to the well-known tumor cell heterogeneity. This invention also provides new possibility of testing the effectiveness of pharmacologic agents by tracking the tumor sizes reflected by their ability to uptake the Dual Nuclear/NIR Agents.

The techniques for the detection and treatment of cancer of this invention have several advantages, such as (1) in vivo distribution of the agents can be detected by a PET or SPECT scanner, (2) the agents are preferentially retained by the cancer cells as opposed to non cancerous cells, (3) the agents labeled with a beta or alpha emitter exhibit toxicity toward cancer cells, (4) the process of the targeted delivery of a drug into tumor tissues by conjugating the drug with the Dual Nuclear/NIR Agents can be individually evaluated with a non-invasive PET, SPECT, or optical imaging techniques, (5) the agents have their emission spectra in the near infrared region of the light spectrum, and (6) the relevant optical images and nuclear images can be correlated with the same imaging agents. The Dual Nuclear/NIR Agents of the present invention are represented by the formulas:

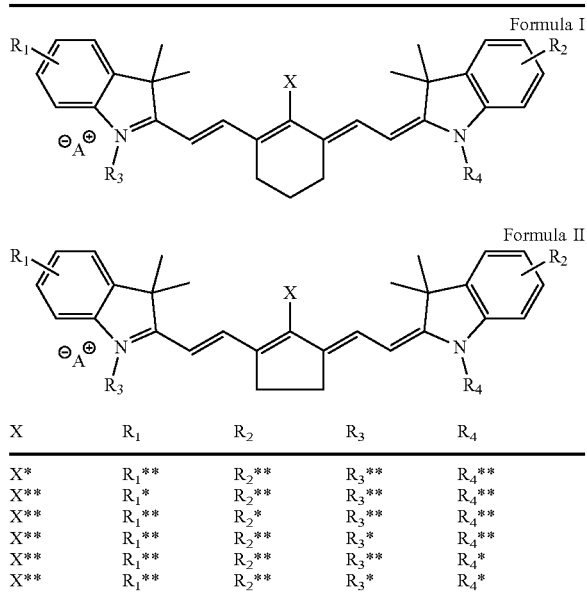

| X | $R_1$ | $R_2$ | $R_3$ | $R_4$ |
|---|---|---|---|---|
| X* | $R_1$** | $R_2$** | $R_3$** | $R_4$** |
| X** | $R_1$* | $R_2$** | $R_3$** | $R_4$** |
| X** | $R_1$** | $R_2$* | $R_3$** | $R_4$** |
| X** | $R_1$** | $R_2$** | $R_3$* | $R_4$** |
| X** | $R_1$** | $R_2$** | $R_3$** | $R_4$* |
| X** | $R_1$** | $R_2$** | $R_3$* | $R_4$* |

$R_1$ and $R_2$ can each be independently selected from the group consisting of radioisotopes I-125, I-123, I-131, I-124, F-18, hydrogen, sulfonato, any electron withdrawing group (EWG), and electron donating group (EDG), and can be independently attached at the various aromatic ring positions such as 3,3', 4,4', 5,5', 6,6';

$R_3$ and $R_4$ can independently be selected from the group consisting of hydrogen, alkyl, aryl, aralkyl, alkylsulfonato, alkylcarboxylic, alkylamino, ω-alkylaminium, ω-alkynyl, PEGyl, PEGylcarboxylate, ω-PEGylaminium, ω-acyl-NH—CR, ω-acyl-lysine-CR, ω-acyl-triazole-CR, ω-PEGyl-carboxyl-NH—CR, ω-PEGylcarboxyl-lysine-CR, and ω-PEGylcarboxyl-triazole-CR;

X can be selected from the group consisting of a hydrogen, halogen, I-125, I-123, I-131, I-124, F-18, CN, Me, OH, 4-O-Ph-CH$_2$CH$_2$COOH, 4-O-Ph-NH—CR, NH—CR, 4-S-Ph-NH—CR, ω-iminoacyl-NH—CR, ω-aminoacyl-lysine-CR, ω-iminoacyl-triazole-CR, 4-O-Ph-CH$_2$CH$_2$COOCT, 4-O-Ph-O-CT, 4-S-Ph-O-CT, and ω-iminoacyl-O-CT;

CR can be selected from the group consisting of a metal chelating agent, a radioactive or nonradioactive metal complex, a radioiodine or iodine labeled Bolten-Hunter reagent, and a radioiodine or iodine labeled tyrosine moiety;

the metal can be selected from the group consisting of Cu-64, In-111, Tc-99m, Ga-68, Y-90, Lu-177, Re-188, At-211, Bi-213, Ac-225 and their nonradioactive counterparts;

CT can be selected from the group consisting of radiolabeled or non-radiolabeled cytotoxic drugs, antibodies, toxins, aptamers, siRNA, antisense constructs and microRNAs; and counteranion A can be selected from the group consisting of iodide, bromide, arylsulfonato, alkylsulfonato, tetrafluoroborate, chloride, and any pharmaceutically acceptable anions;

Each of X*, R1*, R2*, R3*, and R4* refers to the radioactive substitutes selected from their counterpart group of X, R1, R2, and R4, and X, R1, R2, R3 and R4** refers to the non-radioactive moieties.

In some embodiments Cu refers to any isotope of Cu, for example, $^{63}$Cu, $^{64}$Cu, and $^{65}$Cu.

In some embodiments In refers to any isotope of In, for example $^{113}$In, $^{114}$In and $^{115}$In.

In some embodiments Tc refers to any isotope of Tc, for example $^{95m}$Tc, $^{96}$Tc, $^{97}$Tc, $^{97m}$Tc, $^{98}$Tc, $^{99}$Tc, and $^{99m}$Tc.

In some embodiments Ga refers to any isotope of Ga, for example $^{69}$Ga, $^{70}$Ga and $^{71}$Ga.

In some embodiments Y refers to any isotope of Y, for example $^{87}$Y, $^{88}$Y, $^{89}$Y, $^{90}$Y and $^{91}$Y.

In some embodiments Lu refers to any isotope of Lu, for example 173Lu, $^{174}$Lu, $^{175}$Lu, $^{176}$Lu and $^{177}$Lu.

In some embodiments Re refers to any isotope of Re, for example $^{185}$Re, $^{186}$Re and $^{187}$Re.

In some embodiments At refers to any isotope of At, for example $^{209}$At, $^{210}$At, and $^{211}$At.

In some embodiments Bi refers to any isotope of Bi, for example $^{207}$Bi, $^{208}$Bi, $^{209}$Bi and $^{210}$Bi.

In some embodiments Ac refers to any isotope of Ac, for example $^{225}$Ac, $^{226}$Ac and $^{227}$Ac.

In some embodiments I refers to any isotope of I, for example $^{123}$I, $^{124}$I, $^{125}$I, $^{126}$I, $^{127}$I, $^{128}$I, $^{129}$I, $^{130}$I and $^{131}$I.

In some embodiments F refers to any isotope of F, for example $^{18}$F, and $^{19}$F.

In some embodiments Br refers to any isotope of Br, for example $^{79}$Br, $^{80}$Br, and $^{81}$Br.

In some embodiments Cl refers to any isotope of Cl, for example $^{35}$Cl, $^{26}$Cl, $^{37}$Cl.

In some embodiments, A is selected from the group consisting of iodide, bromide, arylsulfonato, alkylsulfonato, tetrafluoroborate, and chloride. In some embodiments, A is chloride. In some embodiments, A is bromide.

In some embodiments, at least one of X, $R_1$, $R_2$, $R_3$ and $R_4$ is a radioactive substituent.

In some embodiments, X can be selected from the group consisting of a hydrogen, halogen, I-125, I-123, I-131, I-124, F-18, CN, Me, OH, 4-O-Ph-CH$_2$CH$_2$COOH, 4-O-Ph-NH—CR, NH—CR, 4-S-Ph-NH—CR, ω-iminoacyl-NH—CR, ω-aminoacyl-lysine-CR, ω-iminoacyl-triazole-CR, 4-O-Ph-CH$_2$CH$_2$COOCT, 4-O-Ph-O-CT, 4-S-Ph-O-CT, and ω-iminoacyl-O-CT. In some embodiments, X can be selected from the group consisting of a hydrogen, halogen, I-125, I-123, I-131, I-124, F-18, CN, Me, OH. In some embodiments, X can be selected from the group consisting of a hydrogen, halogen, I-125, I-123, I-131, I-124, F-18. In some embodiments, X is hydrogen. In some embodiments, X is F, Cl, Br, or I.

In some embodiments, X is selected from the group consisting of I-125, I-123, I-131, I-124, and F-18.

In some embodiments, $R_1$ and $R_2$ are the same. In some embodiments, $R_1$ and $R_2$ are different. In some embodiments $R_1$ and $R_2$ are independently selected from the group consisting of hydrogen, SO$_3$, F, Cl, Br, I, and CN. In some embodiments $R_1$ and $R_2$ are independently selected from the group consisting of I-125, I-123, I-131, I-124, and F-18.

In some embodiments, $R_1$ is at C1. In some embodiments, $R_1$ is at C2. In some embodiments, $R_1$ is at C3. In some embodiments, $R_1$ is at C4.

In some embodiments, $R_2$ is at C1'. In some embodiments, $R_2$ is at C2'. In some embodiments, $R_2$ is at C3'. In some embodiments, $R_2$ is at C4'.

In some embodiment $R_1$ is at C1 and $R_2$ is at C1'. In some embodiment $R_1$ is at C1 and $R_2$ is at C2'. In some embodiment $R_1$ is at C3 and $R_2$ is at C3'. In some embodiment $R_1$ is at C4 and $R_2$ is at C4'

In some embodiments, $R_1$ is at C2 and $R_2$ is at C1'. In some embodiments, $R_1$ is at C3 and $R_2$ is at C1'. In some embodiments, $R_1$ is at C4 and $R_2$ is at C1'.

In some embodiments, $R_1$ is at C1 and $R_2$ is at C2'. In some embodiments, $R_1$ is at C3 and $R_2$ is at C2'. In some embodiments, $R_1$ is at C4 and $R_2$ is at C2'.

In some embodiments, $R_1$ is at C1 and $R_2$ is at C3'. In some embodiments, $R_1$ is at C2 and $R_2$ is at C3'. In some embodiments, $R_1$ is at C4 and $R_2$ is at C3'.

In some embodiments, $R_1$ is at C1 and $R_2$ is at C4'. In some embodiments, $R_1$ is at C2 and $R_2$ is at C4'. In some embodiments, $R_1$ is at C3 and $R_2$ is at C4'.

In some embodiments, $R_1$ and $R_2$ are joined to form a ring.

In some embodiments $R_1$ or $R_2$ is selected from the group consisting of I-125, I-123, I-131, I-124, and F-18.

In some embodiments, $R_3$ and $R_4$ are the same. In some embodiments, $R_3$ and $R_4$ are different. In some embodiments, $R_3$ and $R_4$ are independently selected from the group consisting of $C_{1-5}$alkyl-$R_{10}$, $C_{1-4}$alkylC(O)N(H)C(H)(CO$_2$H)C$_{1-4}$alkylN(H)C(O)—C$_6$arylN(H)—$R_{10}$, $C_{1-4}$alkyl-$R_{10}$, $C_{1-4}$alkylC(O)N(H)C(H)(CO$_2$H)C$_{1-4}$alkylN(H)C(O)—C$_6$heteroarylN(H)—$R_{10}$, $C_{1-4}$alkylC(O)N(H)C$_{1-4}$alkylC(H)(CO$_2$H)N(H)—$R_{10}$; $C_{1-6}$alkylC(O)N(H)—$R_{10}$; $C_{1-6}$alkylN(H)—$R_{10}$; [(CH$_2$)$_2$O]$_{2-4}$CH$_2$N(H)

In some embodiments, $R_3$ and $R_4$ are independently selected from the group consisting of

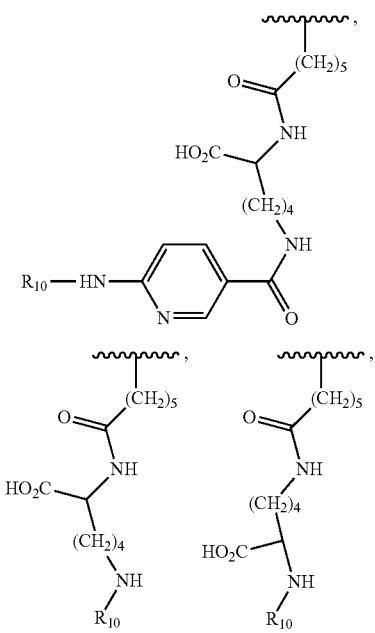

$C_{3-5}$alkylC(O)N(H)—$R_{10}$; $C_{3-5}$alkylN(H)—$R_{10}$.

In some embodiments, $R_{10}$ is a metal chelating agent. In some embodiments, $R_{10}$ is a radiolabeled moiety. In some embodiments, $R_{10}$ is selected from the group consisting of

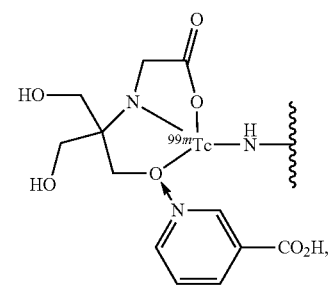

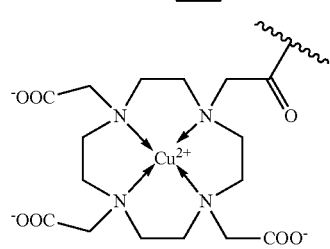

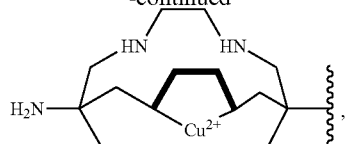

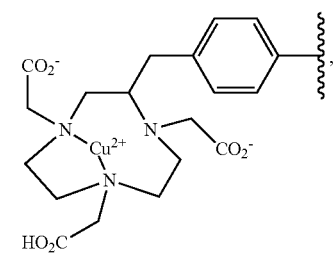

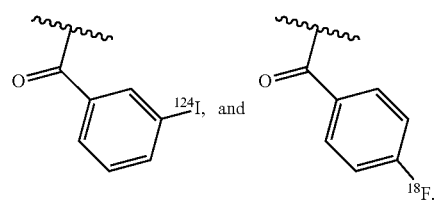

In some embodiments, at least one of $R_3$ or $R_4$ is selected from the group consisting of

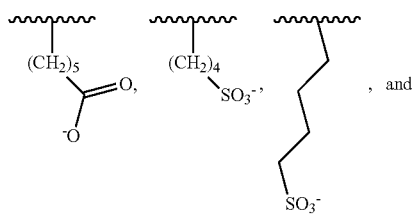

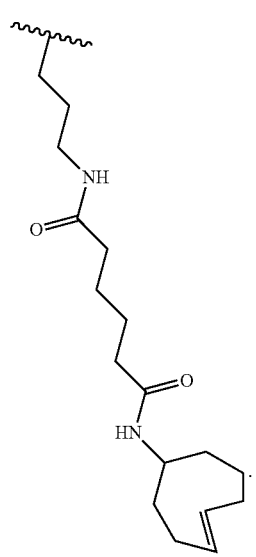

In some embodiments, at least one of R₃ or R₄ is selected from the group consisting of
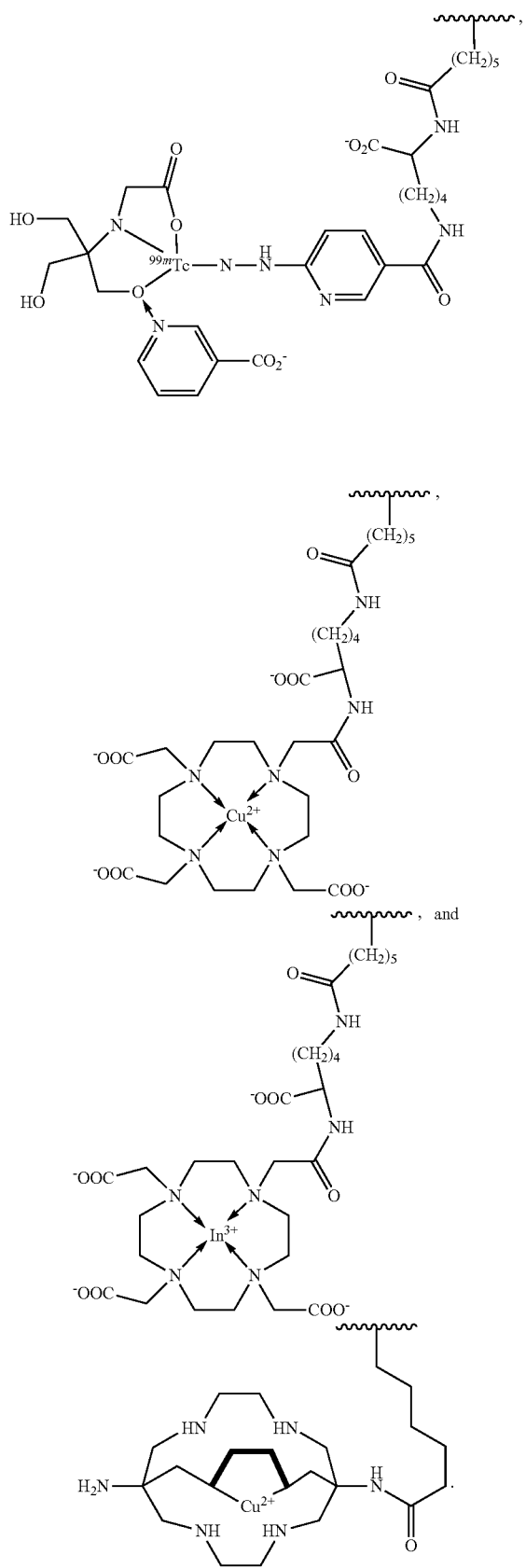
In some embodiments, the Dual Nuclear/NIR Agents is selected from the group consisting of,
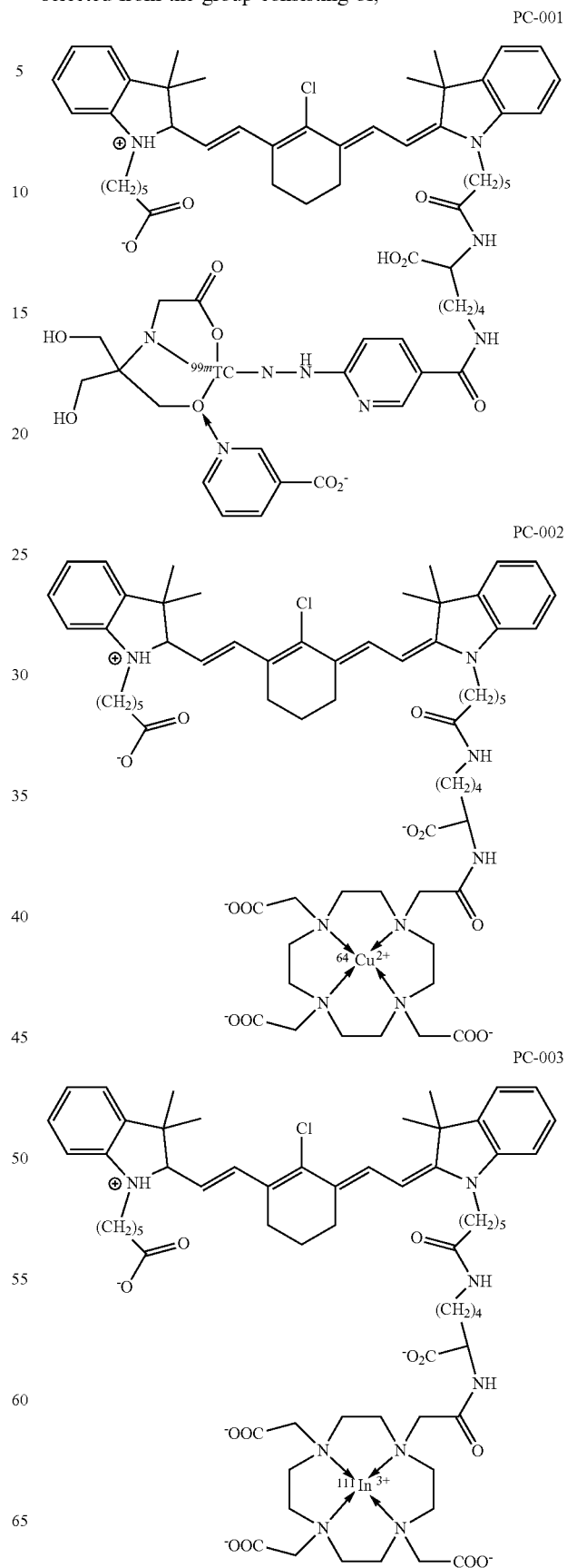

PC-004
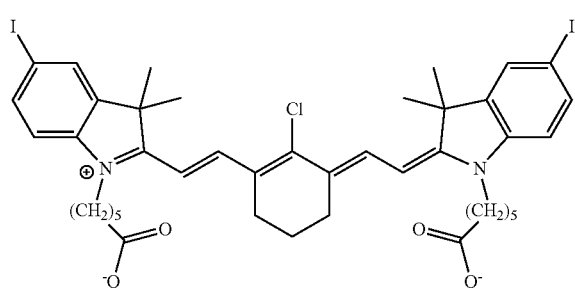
PC-007
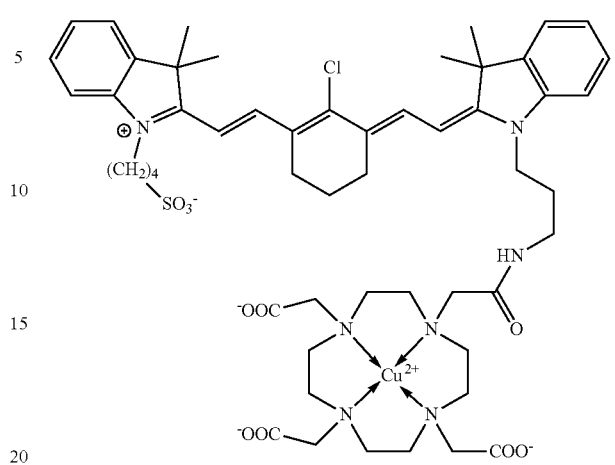
PC-005
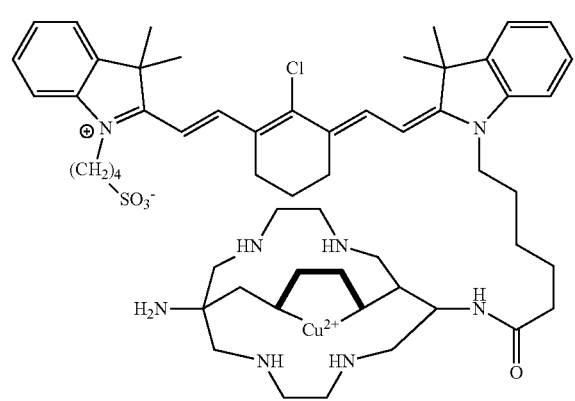
PC-1001
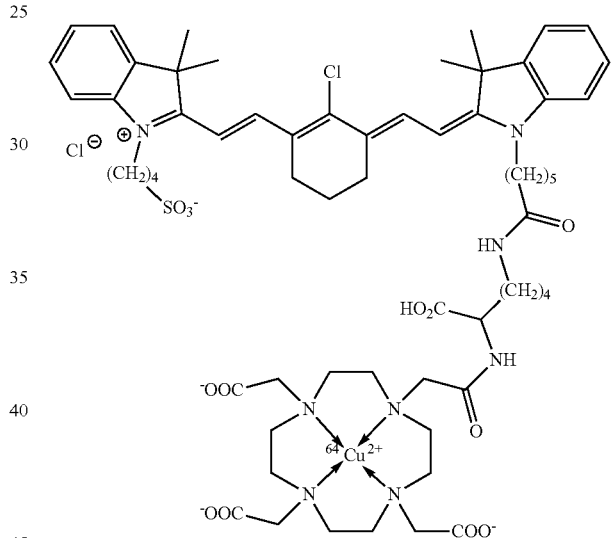
PC-006
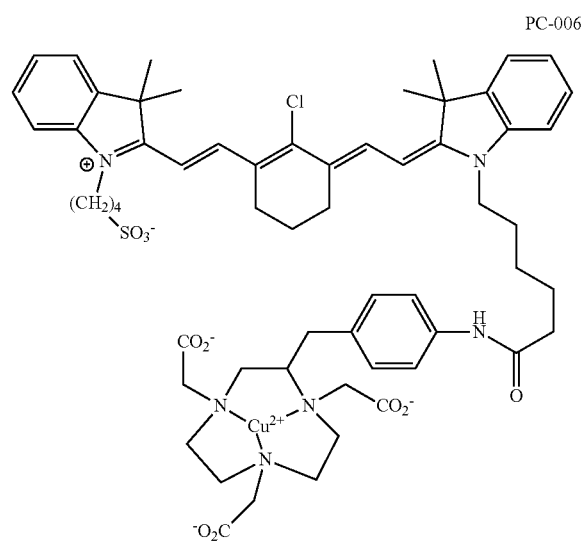
PC-1002
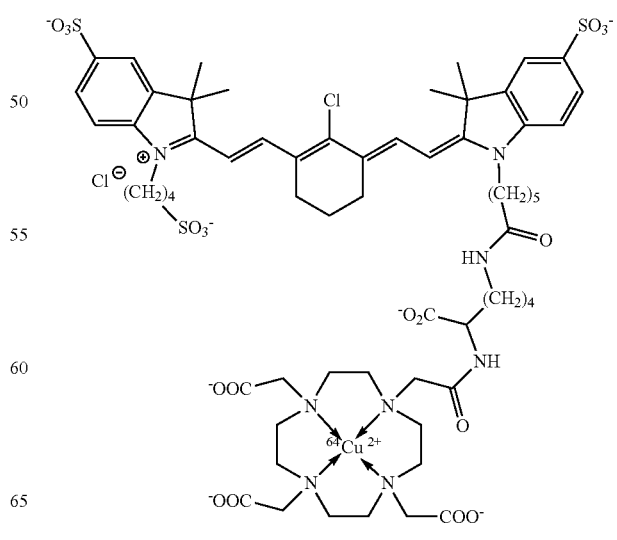

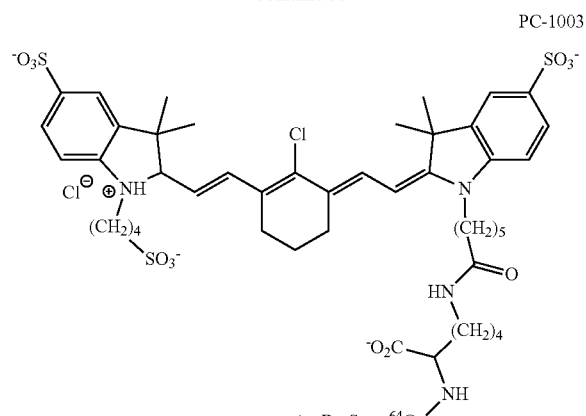
PC-1003
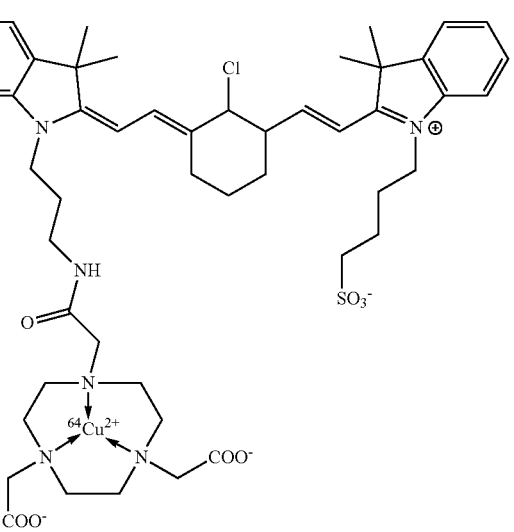
PC-1006
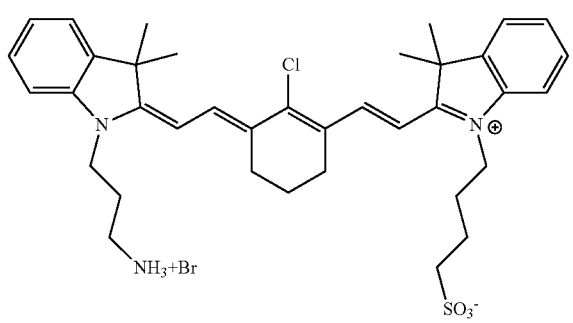
PC-1004
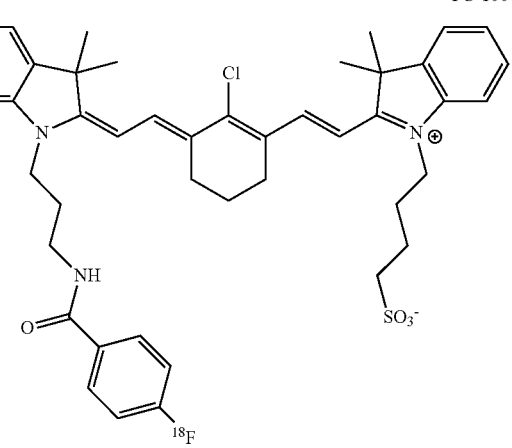
PC-1007
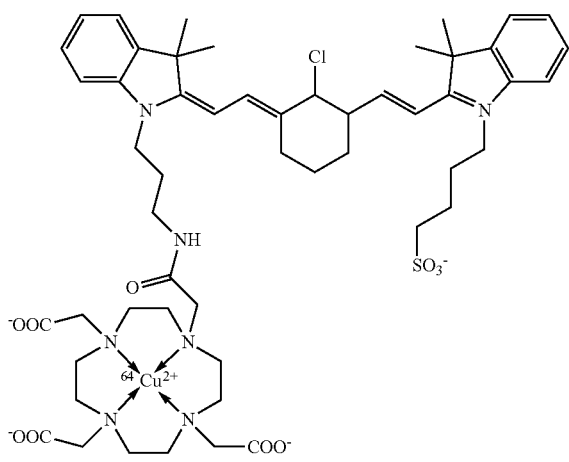
PC-1005
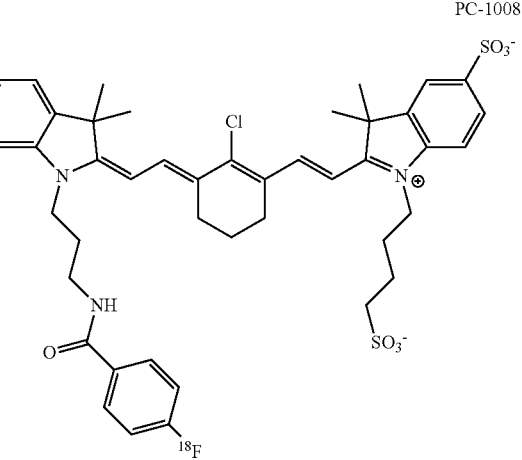
PC-1008

PC-1009
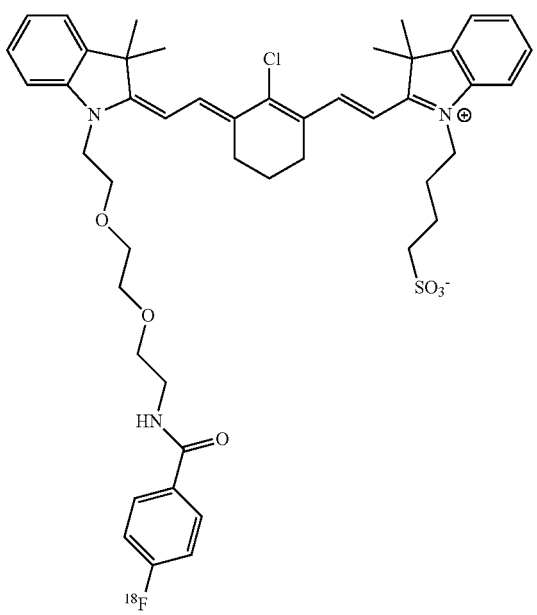
PC-1010
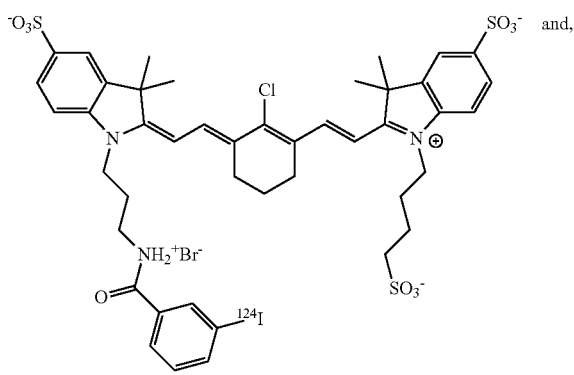
PC-1011
PC-1012
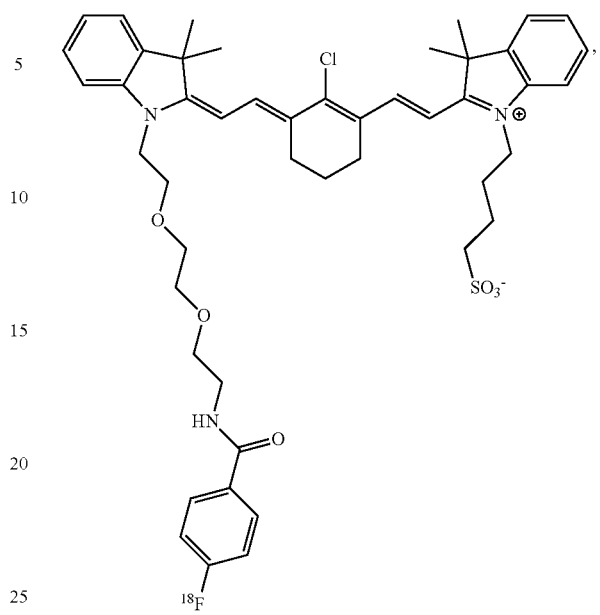
wherein AmBarSa has the chemical structure:
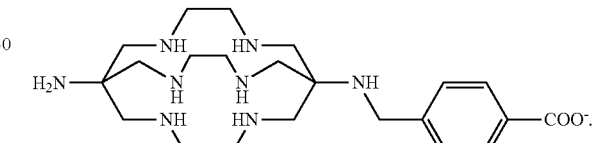
In some embodiments, the compound of the invention is selected from the group consisting of:
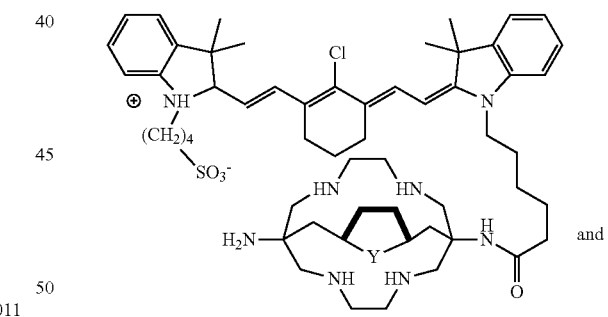
and,
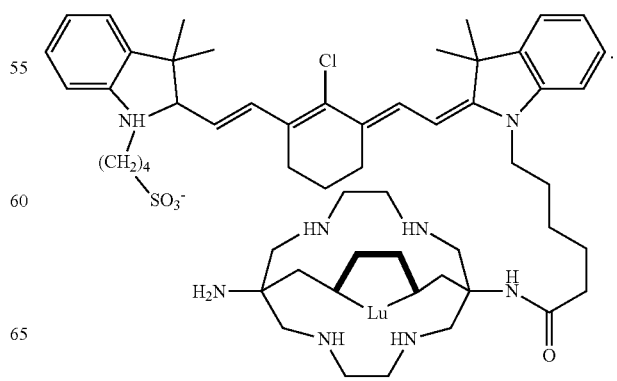

A Two-step pretargeting imaging strategy is employed to decouple the NIR dye-based targeting agent (PC-1013) from its respective imaging reporter with $^{18}F$ isotope (PC-1014).

ester 6 with $N^{\omega}$-(t-butoxyhydrazinonicotinyl)-lysine 7 in acetonitrile-sodium borate buffer by incubating; adding TFA to the mixture; incubating the mixture to remove the t-bu

PC-10013

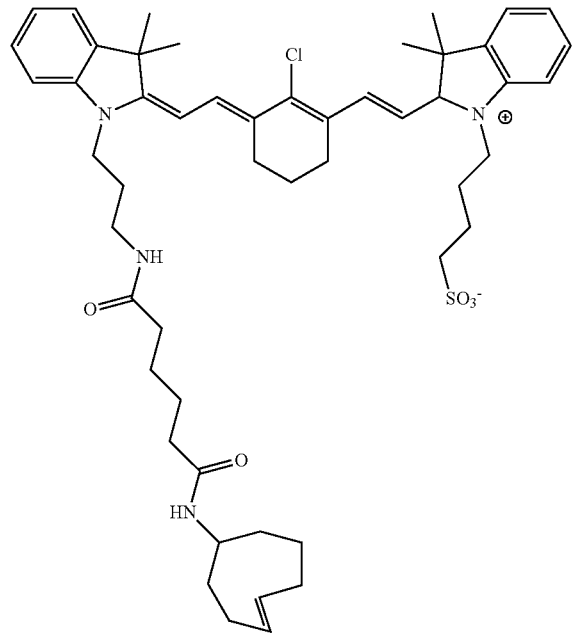

PC-10014

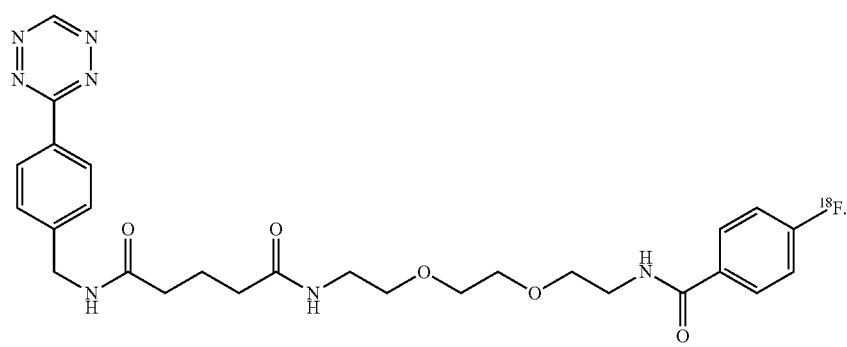

The Dual Nuclear/NIR Agents of the present invention can be in the form of an ester, amide, salt, solvate, or metabolite.

Any method of synthesis known to one of the ordinary skill in the art may be used to synthesized the compounds of the invention. Examples of synthesis are illustrated in the Examples section.

In some embodiments, a method of synthesizing and radiolabeling of PC-001 (Scheme 1) comprises: heating an ethanol solution of 2,3,3-trimethylindolenine 1 and 6-bromohexanoic acid 2 to produce 1-(5'-carboxypentyl)-2,3,3-trimethylindolinium bromide 3; mixing compound 3 with N-[5-anilino-3-chloro-2,4-(propane-1',3'-diyl)-2,4-pentadien-1-ylidene]anilinium chloride 4 and sodium acetate in ethanol; refluxing the solution; concentrating the solution to dryness; trituated the residue with HCl; drying the residue to yield 5; adding DCC to a solution of 5 and N-hydroxysuccimide in methylene chloride; stirring the mixture; removing the precipitates; removing methylene chloride to obtain monosuccinimide ester 6; conjugating monosuccinimide toxyl protecting group; removing the solvent; purifying the concentrated residue to obtain the labeling precursor, 2-((E)-2-((E)-3-((E)-2-(1-(6-(1-carboxy-5-(6-hydrazinylnicotinamido)pentylamino)-6-oxohexyl)-3,3-dimethylindolin-2-ylidene)ethylidene)-2-chlorocyclohex-1-enyl)vinyl)-1-(5-carboxypentyl)-3,3-dimethyl-3H-indolium 8; consecutively adding together 8, ethanol, tricine solution, 100 nicotinic acid solution, $^{99m}TcO_4^-$ solution, and $SnCl_2$ solution; mixing the reaction mixture; heating the reaction mixture; cooling the reaction mixture; and purifying the reaction mixture to obtain PC-001.

In some embodiments, a method of synthesizing and radiolabeling PC-002 (Scheme 2) comprises: heating an ethanol solution of 2,3,3-trimethylindolenine 1 and 6-bromohexanoic acid 2 to produce 1-(5'-carboxypentyl)-2,3,3-trimethylindolinium bromide 3; mixing compound 3 with N-[5-anilino-3-chloro-2,4-(propane-1',3'-diyl)-2,4-pentadien-1-ylidene]anilinium chloride 4 and sodium acetate in ethanol; refluxing the solution; concentrating the solution to dryness; trituated the residue with HCl; drying the residue to yield 5; adding DCC to a solution of 5 and N-hydroxysuccimide in methylene chloride; stirring the mixture; removing the precipitates by filtration; removing methylene chloride to obtain monosuccinimide ester 6; conjugating monosuccinimide ester 6 with N-α-tBoc-lysine; treating the conjugated monosuccinimide ester 6 with TFA to yield M10; coupling of 10 with DOTA-Sulfo-NHS, in acetonitrile-water to yield the 12; adding $^{64}CuCl_2$ to 12 in ammonium acetate buffer; incubating the mixture; and purifying the mixture to obtain PC-002.

In some embodiments, a method of synthesizing PC-004 (Scheme 3) comprises: heating a solution of 4-Iodophenylhydrazine 15, isopropylmethylketone, EtOH and concentrated $H_2SO_4$ under reflux; cooling the solution; filtering the solution to obtain a filtrate; adding the filtrate to distilled water; extracting 5-iodo-2,3,3-trimethylindolenine 16 with $CH_2Cl_2$; washing the combined organic layer with $NaHCO_3$ and distilled water; drying the 5-iodo-2,3,3-trimethylindolenine 16; filtering the 5-iodo-2,3,3-trimethylindolenine 16; evaporating the 5-iodo-2,3,3-trimethylindolenine 16; heating a solution of the 5-iodo-2,3,3-trimethylindolenine 16 and 6-bromohexanoic acid 2 to produce 1-(5'-carboxypentyl)-5-iodo-2,3,3-trimethylindolinium bromide 17; mixing 1-(5'-carboxypentyl)-5-iodo-2,3,3-trimethylindolinium bromide 17 with N-[5-anilino-3-chloro-2,4-(propane-1',3'-diyl)-2,4-pentadien-1-ylidene]anilinium chloride 4 and sodium acetate in ethanol; refluxing the solution; concentrating the solution to dryness; trituating the residue with HCl; drying the residue to produce 18.

The present invention also provides pharmaceutically acceptable salts of the compounds of the invention. Examples of pharmaceutically acceptable salts of the compounds according to the invention include acid addition salts. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, ptoluenesulfonic, benzesulfonic, and isothionic acids. Other useful acid addition salts include propionic acid, glycolic acid, oxalic acid, malic acid, malonic acid, benzoic acid, cinnamic acid, mandelic acid, salicylic acid, and the like. Particular examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, harates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound of the present invention may be prepared in a similar manner using a pharmaceutically acceptable inorganic or organic base, such as an amine (primary, secondary or tertiary), an alkali metal or alkaline earth metal hydroxide or the like.

Illustrative examples of suitable salts include, but are not limited to, organic salts derived from amino acids such as glycine and arginine, ammonia, primary, secondary and tertiary mines, and cyclic amines such as piperidine, morpholine and piperazine, and inorganic salts derived from sodium, calcium, potassium, magnesium, manganese, iron, copper, zinc, aluminum and lithium.

Exemplary bases include, but are not limited to, sodium hydroxide, potassium hydroxide, ammonium hydroxide, calcium hydroxide, triethylamine, or the like.

Esters of the compounds of the present invention may be prepared through functionalization of hydroxyl and/or carboxyl groups that may be present within the molecular structure of the compound. Esters and amides of compounds of the invention can be made by reaction with a carbonylating agent (e.g., ethyl formate, acetic anhydride, methoxyacety) chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C.

Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid formulations of the precursors of the radiolabeled compounds, it is understood that the inventive compounds may exist in different forms, such as stable and metastable crystalline forms and isotropic and amorphous forms, all of which are intended to be within the scope of the present invention. The present invention also includes stereoisomers of the compounds described herein, where applicable, either individually or admixed in any proportions.

Stereoisomers may include, but are not limited to, enantiomers, diastereomers, racemic mixtures and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in a mixture with other isomers of the compounds described herein.

The term "isomer" as used herein refers to a compound with the same molecular formula but different structural formulas. Isomers do not necessarily share similar properties, unless they also have the same functional groups. There are many different classes of isomers, like stereoisomers, enantiomers, geometrical isomers, etc. There are two main forms of isomerism: structural isomerism and stereoisomerism (spatial isomerism).

The designations "R" and "S" are used to denote the absolute configuration of a molecule about its chiral center. The designations can appear as a prefix or as a suffix; they can or cannot be separated from the isomer by a hyphen; they can or cannot be hyphenated; and they can or cannot be surrounded by parentheses.

The term "S isomer" as used herein refers to an enantiomer with the chiral center S according to a system by which its substituents are each assigned a priority, according to the Cahn-Ingold-Prelog priority rules (CIP), based on atomic number, where the priority of atomic number decreases in counterclockwise direction, it is S enantiomer (from the Latin Sinestra, meaning "left"). Without wishing to be limited to theory, if the center is oriented so that the lowest-priority of the four is pointed away from a viewer, the viewer will then see two possibilities: If the priority of the remaining three substituents decreases in clockwise direction, it is labeled R (from the Latin Rectus, meaning "right"), if it decreases in counterclockwise direction, it is S (from the Latin Sinestra, meaning "left").

Radiopharmaceutical Compositions Comprising Dual Nuclear/NIR Agents

The present invention also provides radiopharmaceutical formulations or compositions, both for veterinary and for human medical use, which comprise the compounds of the invention (or ester, amide, salt, solvate, metabolite, or derivative thereof) with one or more pharmaceutically acceptable carriers thereof. The carrier(s) must be pharmaceutically acceptable in the sense of being compatible with the other ingredients of the formulation and not unduly deleterious to the recipient thereof. Such carriers are known in the art. See, Wang et al. (Wang 1980) herein incorporated by reference in its entirety. Formulations of the present invention may include short-term, rapid-onset, rapid-offset, controlled release, sustained release, delayed release vary, especially depending upon the condition of the recipient and the disorder being treated.

The compounds and radiopharmaceutical compositions of the present invention can be administered by an appropriate route. Suitable routes of administration include, but are not limited to, orally, intraperitoneally, subcutaneously, intramuscularly, transdermally, rectally, sublingualis intravenously, buccally, or inhalationally. In some embodiments, the radiopharmaceutical compositions of the invention contain a pharmaceutically acceptable excipient suitable for rendering the compound or mixture administrable orally, parenterally, intravenously, intradermally, intramuscularly or subcutaneously, rectally, via inhalation or via buccal administration, or transdermally. In some embodiments, the radiopharmaceutical compositions can be administered through urogenital routes to reach to targets, such as internal organs, topical lesions, or organs can be accessed by instillation (such as urinary bladder, vaginal cannel) more effectively and efficiently.

The active ingredients can be admixed or compounded with a conventional, pharmaceutically acceptable excipient. It will be understood by those skilled in the art that a mode of administration, vehicle, excipient or carrier conventionally employed and which is inert with respect to the active agent can be utilized for preparing and administering the pharmaceutical compositions of the present invention. Illustrative of such methods, vehicles, excipients, and carriers are those described, for example, in *Remington's Pharmaceutical Sciences*, 18th ed. (1990), the disclosure of which is incorporated herein by reference. The formulations of the present invention for use in a subject comprise the agent, together with one or more acceptable excipient thereof, and optionally other therapeutic agents. The excipient must be "acceptable" in the sense of being compatible with the other ingredients of the formulation and not deleterious to the recipient thereof.

The radiopharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds according to the present invention (or a pharmaceutically acceptable ester, amide, salt, or solvate thereof) with a suitable carrier or other adjuvant, which may consist of one or more ingredients. The combination of the active ingredient with the one or more adjuvants is then physically treated to present the formulation in a suitable form for delivery (e.g., forming an aqueous suspension).

Since administration of parenteral dosage forms typically bypasses the patient's natural defenses against contaminants, parenteral dosage forms can be sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Adjuvants or accessory ingredients for use in the formulations of the present invention can include any pharmaceutical ingredient commonly deemed acceptable in the art, such as mixtures, buffers, solubility enhancers, and the like.

Suitable vehicles that can be used to provide parenteral dosage forms of the compounds of the invention include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a compound of the invention as disclosed herein can also be incorporated into the parenteral dosage forms of the disclosure, including conventional and controlled-release parenteral dosage forms.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active compound.

Forms suitable for oral or sublingual administration include tablets, troches, capsules, elixirs, suspensions, syrups, wafers, chewing gum, or the like prepared by art recognized procedures. The amount of active compound in such therapeutically useful compositions or preparations is such that a suitable dosage will be obtained. A syrup formulation will generally consist of a suspension or solution of the compound or salt in a liquid carrier, for example, ethanol, glycerine or water, with a flavoring or coloring agent.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

In some embodiments, a compound of the invention as described herein can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

It is appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It is appreciated that the therapies employed can achieve a desired effect for the same disorder (for example, an inventive compound can be administered concurrently with another cancer therapeutic agent), or they can achieve different effects (e.g., control of an adverse effects).

For example, other therapies, imaging agents, and/or cancer therapeutic agents that can be used in combination with the inventive compounds of the present invention for imaging, targeting, detecting and/or treating tumors including, radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE®. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In certain embodiments, the pharmaceutical compositions of the present invention further comprise one or more additional therapeutically active ingredients (e.g., chemotherapeutic and/or palliative). For purposes of the invention, the term "palliative" refer, to treatment that is focused on the relief of symptoms of a disease and/or side effects of a therapeutic regimen, but is not curative.

The radioactive salts of the present invention may be especially useful in the treatment of cancer, although other patient treatments are also within the scope of the present invention.

In embodiments which involve salts of compounds of the invention containing radiolabelled phosphorous, and especially, the implantation of the radioactive salts in a tumor in vivo may provide desirable exposure of the tumor to radiation while minimizing the exposure to radiation of nearby, normal tissue. It is contemplated that a wide variety of cancers, especially solid tumor cancers, may be treated using the radioactive salts of the present invention. Examples of such solid tumor cancers include, for example, cancers of the head, such as brain cancer, and cancers of the neck, endometrium, liver, breast, ovaries, kidney, cervix and prostate. Embodiments of the invention which involve radioactive salts compounds of the invention, may be particularly suitable for use in the treatment of cancer. The radioactive salts of the present invention may be administered to the patient in a variety of forms, depending on the particular route of administration, the particular salt and/or isotope involved, the particular cancer being treated, and the like. In the case of brachytherapy, the radioactive salts may be administered using techniques which are well known to those skilled in the art, including, for example, surgical implantation. In the case of the administration of radioactive salts in the form, for example, of an aqueous composition or suspension (discussed more fully hereafter), the aqueous composition or suspension may be administered by being injected at the desired site. In addition, the radioactive salts of the present invention may be administered in the form of a radiopharmaceutical matrix (discussed more fully hereafter), also by injection or surgical implantation at the desired site. The particular technique employed for administering the matrix may depend, for example, on the shape and dimensions of the involved matrix. In some embodiments, the radioactive salt is introduced substantially homogeneously in a tumor to minimize the occurrence in the tumor of cold (untreated) areas. In certain embodiments, the radioactive salt is administered in combination with a pharmaceutically acceptable carrier. A wide variety of pharmaceutically acceptable carriers are available and can be combined with the present radioactive salts. Such carriers would be apparent to one skilled in the art, based on the present disclosure. In some embodiments, any material used as a carrier is biocompatible.

"Biocompatible", as used herein, refers to materials which are generally not injurious to biological functions and which will not result in any degree of unacceptable toxicity, including allergenic responses and disease states. Suitable carriers include, but are not limited to, water, buffer or saline solution. Other suitable carriers are described, for example, in Remington's, Pharmaceutical Sciences, Gennaro, A. R., ed., Mack Publishing Co., Easton, Pa. (1985), and The United States Pharmacopeia—The National Formulary, 22nd Revision, Mack Printing Company, Easton, Pa. (1990), the disclosures of each of which are hereby incorporated herein by reference, in their entirety.

The concentration of the radioactive salt employed in the pharmaceutical compositions and/or the amount of radioactive salt administered to the patient may vary and depends upon a variety of factors including, for example, the particular radioactive salt and/or pharmaceutically acceptable carrier employed, the particular disease being treated, the extent of the disease, the size and weight of the patient, and the like. Typically, the radioactive salt may be employed in the pharmaceutical compositions, and the compositions may be administered to a patient to provide initially lower levels of radiation dosages which may be increased until the desired therapeutic effect is achieved. Generally speaking, the radioactive salt may be employed in pharmaceutical compositions which comprise an aqueous carrier to provide a concentration of absolute radioactivity which may range from about 4 MBq per milliliter (mL) (about 0.1 mCi/mL) or less to about 370 MBq/mL (about 10 mCi/mL), and all combinations and subcombinations of ranges therein. In some embodiments, the concentration of the radioactive salt in the pharmaceutical compositions may be from about 37 MBq/mL (about 1 mCi/mL) to about 370 MBq/mL (about 10 mCi/mL). In addition, the compositions may be administered to a patient to provide a radiation dose which may range from about 1 KSv (about 1×105 Rem) to about 74 KSv (about 7.4 MRem), and all combinations and subcombinations of ranges therein. In some embodiments, the compositions may be administered to a patient to provide a radiation dose of from about 7.4 KSv (about 7.4×105 Rem) to about 74 KSv (about 7.4 MRem). Such amounts are referred to herein as effective amounts or therapeutically effective amounts. In certain embodiments, the pharmaceutically acceptable carrier may further comprise a thickening agent.

"Thickening agent", as used herein, refers to any of a variety of generally hydrophilic materials which, when incorporated in the present compositions, may act as viscosity modifying agents, emulsifying and/or solubilizing agents, suspending agents, and/or tonicity raising agents. Thickening agents which may be suitable for use in the present radiopharmaceutical compositions include, for example, gelatins, starches, gums, pectin, casein and phycocolloids, including carrageenan, algin and agar, semisynthetic cellulose derivatives; polyvinyl alcohol and carboxyvinylates; and bentonite, silicates and colloidal silica. Exemplary of the foregoing materials are, for example, carbohydrates such as, for example, mannitol, glucose and dextrose, and the phosphorylated and sulfonated derivatives thereof; agarose; polyethers, including polyethers having a molecular weight of, for example, from about 400 to about 100,000; di- and trihydroxy alkanes and their polymers having a molecular weight of, for example, about 200 to about 50,000; acacia; diethanolamine; glycerol monostearate; lanolin alcohols; lecithin; mono- and diglycerides; monoethanolamine; oleic acid; oleyl alcohol; polyoxyethylene 50 stearate; polyoxyl 35 castor oil; polyoxyl 10 oleyl ether; polyoxyl 20 cetostearyl ether; polyoxyl 40 stearate; propylene glycol diacetate; propylene glycol monostearate; sodium stearate; stearic acid; trolamine; emulsifying wax; agar; alginic acid; aluminum monostearate; bentonite; magma; carbomer 934P; hydroxyethyl starch; carboxymethylcellulose; calcium and sodium and sodium 12; carrageenan; cellulose; dextran; gelatin; guar gum; locust bean gum; veegum; hydroxyethyl cellulose; hydroxypropylmethylcellulose; agnesiumaluminum-silicate; methylcellulose; pectin; polyethylene oxide; povidone; propylene glycol alginate; silicon dioxide; sodium alginate; tragacanth; xanthan gum; a-dgluconolactone; glycerol; mannitol; polyethyleneglycol (PEG); polyvinylpyrrolidone (PVP); polyvinylalcohol (PVA); polypropylene glycol; polysorbate; sorbitol; propyleneglycol; glycerol; and polyoxyethylene-polyoxypropylene glycol block copolymers. Preferred among the polyoxyethylene-polyoxypropylene glycol block copolymers are a-hydroxy-w-hydroxypoly(oxyethylene)poly(oxypropylene)-poly(oxyethylene) block copolymers. These latter block copolymers are generally referred to as poloxamer copolymers. Examples of poloxamer copolymers include, for example, poloxamer F68, poloxamer L61 and poloxamer L64. These poloxamer copolymers are commercially available from Spectrum 1100 (Houston, Tex.). Preferred among the thickening agents listed above are gelatins, polyvinylpyrrolidone and polyoxyethylene-polyoxypropylene glycol block copolymers. Other thickening agents, in addition to those exemplified above, would be apparent to one skilled in the art, based on the present disclosure.

The concentration of thickening agent, when present in the compositions of the present invention, may vary and depends upon various factors, including, for example, the particular thickening agent, radioactive salt, pharmaceutically acceptable carrier, and the like, employed. In some embodiments, the concentration of thickening agent is at least sufficient to impart desirable properties to the compositions, including, for example, a modification of the viscosity of the compositions. Generally speaking, the concentration of thickening agent may range from about 0.1 to about 500 milligrams (mg) per mL of pharmaceutical composition, and all combinations and subcombinations of ranges therein. In certain embodiments, the concentration of thickening agent may be from about 1 to about 400 mg/mL. In some embodiments, the concentrations range from about 5 to about 300 mg/mL. In some embodiments, the concentration of thickening agent can be 20 from about 10 to about 200 mg/mL. In some embodiments, the concentrations range from about 20 to about 100 mg/mL. The concentrations of thickening agent of from about 25 to about 50 mg/mL. Compositions which may be prepared from the radioactive salts, pharmaceutically acceptable carriers and optional thickening agents include, for example, suspensions, emulsions, and dispersions. In some embodiments, the radioactive salts can be formulated and administered to a patient as a suspension.

"Suspension", as used herein, refers to a 30 mixture, dispersion or emulsion of finely divided colloidal particles in a liquid.

"Colloidal", as used herein, refers to a state of subdivision of matter which comprises particles of single large molecules or aggregations of smaller molecules. The particles may be sized microscopically and together comprise the dispersed phase. This dispersed phase is generally surrounded by different matter, generally referred to as the dispersion medium or external phase. Suspensions may be obtained, for example, by combining the radioactive salt with an inert support material.

"Inert", as used herein, refers to substances which are generally resistant to chemical or physical action. In some embodiments, the inert substances are also biocompatible. In some embodiments, the inert support material is an adsorbent and/or absorbent solid on which the radioactive salt may be adsorbed and/or absorbed. In some embodiments, the inert solid may comprise particles. In some embodiments, the particles are finely divided particles. Such support materials are referred to herein as "particulate support materials." Particulate support materials which may be suitable for use as an inert solid support in the compositions of the present invention include, for example, materials derived from carbon, including those forms of carbon typically referred to as carbon black (lampblack) and/or activated carbon, as well as finely powdered oxides, Kieselguhr, and diatomaceous earth. In some embodiments, the support material comprises carbon black or activated carbon. The size of the particles of the particulate support material may vary and depends, for example, on the particular support material, radioactive salt, thickening agent, and the like, employed. Generally, the particulate support material 60 may comprise particles ranging in size, for example, from about 0.1 micrometer (mm) to about 50 mm, and all combinations and subcombinations of ranges therein. In some embodiments, the particle size may be from about 0.5 to about 25 mm. In some embodiments, the particle size ranges from about 1 to about 10 mm. In some embodiments, the particle size of the particulate support material may be from about 2 to about 5 mm. Geigy Corp. (Brawater, N.Y.).

The concentration of the radioactive salt employed may vary and depends upon a variety of factors including, for example, the particular radioactive salt and/or polymeric resins employed, the use of additional agents in the resin mixture, such as curing agents and/or hardening agents, the particular disease being treated, the extent of the disease, the size and weight of the patient, and the like. Typically, the radioactive salt may be employed in the polymeric resin or resins and, accordingly, the matrices, and the matrices may be administered to a patient to provide initially lower levels of radiation dosages which may be increased until the desired therapeutic effect is achieved. Generally speaking, the radioactive salt may be employed in a concentration of from greater than 0 to about 50%, and all combinations and subcombinations of ranges therein, based on the total weight of the resin or resins and optional curing or hardening agent employed. In some embodiments, the concentration of the radioactive salt is from about 0.5 to about 40%. In some embodiments, the concentration ranges from about 1 to about 30%. In some embodiments, the radioactive salt is employed in a concentration of from about 1.5 to about 20%. In some embodiments the concentration ranges from about 2 to about 10%. In some embodiments, the concentration of radioactive salt is from about 3 to about 5%. In some embodiments, the concentration is about 4%.

The mixture of radioactive salt, polymeric resin, and optional additional ingredients may be blended until homogenous, and the resulting mixture may be introduced into the biocompatible sleeve, such as a Dacron® sleeve, so that the sleeve substantially surrounds the radioactive resin mixture. The introduction of the resin mixture into the sleeve may be accomplished, for example, by pumping the mixture into the sleeve using an appropriate mechanical and/or vacuum pump. Suitable pumps for this purpose are readily available and would be apparent to one of ordinary skill in the art, based on the present disclosure.

The particular pump employed may depend, for example, on a variety of factors, including the viscosity of the resinous mixture, as well as the dimensions of the sleeve employed, namely, its length and inner and outer diameters. The dimensions of the sleeve employed, in turn, can vary and depends upon a variety of factors including, for example, the particular radioactive salt and/or polymeric resins employed, the particular disease being treated, the extent of the disease, the size and weight of the patient, and the like. Generally speaking, the length of the sleeve employed can range from about 0.1 cm to about 5 cm, and all combinations and subcombinations of ranges therein. In some embodiments, the sleeve length can range from about 0.3 cm to about 3 cm. In some embodiments, the length is from about 0.8 cm to about 2 cm. In some embodiments, the sleeve length can be about 1 cm. The external diameter of the sleeve can range from about 0.2 mm to about 2 mm, and all combinations of ranges therein. In some embodiments, the external diameter can range from about 0.5 mm to about 1.5 mm. In some embodiments, the external diameter is of about 1 mm. The internal diameter of the sleeve can range from about 0.1 mm to about 1.8 mm, and all combinations of ranges therein. In some embodiments, the internal diameter can range from about 0.3 mm to about 1.3 mm. In some embodiments, the internal diameter can range about less than about 1 mm, such as about 0.8 mm.

In some embodiments, after introduction into the sleeve, the resin mixture containing the radioactive salt is cured to provide the present solid matrices. The curing method employed can vary and depends, for example, on the particular polymeric resin and optional curing and/or hardening agents employed. Generally speaking, the resin mixture can be cured, for example, by the application of heat or ultraviolet (UV) light. In some embodiments, the curing is done with heat curing. The resulting matrix can thereafter be administered to a patient, as described herein.

The present invention also provides convenient pharmaceutical kits. Such kits can comprise a radioactive salt of compound of the invention and, typically, a pharmaceutically acceptable carrier. The kit can also further comprise conventional kit components, such as needles for use in injecting the compositions, one or more vials for mixing the composition components, and the like, as are apparent to those skilled in the art. In addition, instructions, either as inserts or as labels, indicating quantities of the components, guidelines for mixing the components, and protocols for administration, can be included in the kits.

Methods of Using the Dual Nuclear/NIR Agents of the Invention

The compounds of the invention are believed to act as agents with preferential entry and retention in cancer cells in vivo upon ambient administration. It is believed that the compounds are, therefore, useful to identify and treat or prevent any condition responsive to the preferential entry and retention properties of the compounds of the invention.

Subjects which can be imaged or treated include animal subjects, typically vertebrates, including both mammalian (e.g., human, cat, dog, cow, horse, sheep, pig, monkey, ape, etc.) and avian subjects (e.g., chicken, turkey, duck, goose, quail, pheasant, etc.).

For example, the compounds of the present invention can be used in the treatment of cancerous tissue and the tumors associated therewith, including breast, colon, prostate and skin cancer.

In one aspect of the invention, administering an effective amount of a compound of the invention to a subject can result in detection of cancerous tissue. Additionally, the same or other compounds of this invention can be cytotoxic in cancerous tissue. Thus, the present invention can provide methods for detecting and treating tumor-bearing subjects in which the compounds of the invention are administered to the subject in need of such treatment in a manner effective to identify and/or treat such tumors.

By "treatment or prevention" the term is intended to refer to the alleviation of the signs, symptoms, or causes of a disease, or any other desired alteration of a biological system. Accordingly, the method of the invention "prevents" (i.e., delays or inhibits) and/or "reduces" (i.e., decrease, slows, or ameliorates) the detrimental effects of the cancer, or neoplastic disease or disorder, in the mammal receiving the therapy.

As used herein, a "neoplastic disease or disorder" is characterized by one or more of the following properties: cell growth that is not regulated by the normal biochemical and physical influences in the environment; anaplasia (i.e., lack of normal coordinated cell differentiation); and in some instances, metastasis. Further, as used herein, the term "cancer" is understood to mean a disease characterized by abnormal growth of cells that is not regulated by the normal biochemical and physical influences in the environment. Accordingly, as used herein, the terms cancer and neoplasia are intended to be interchangeable.

Neoplastic diseases capable of treatment according to the invention include, for example, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, ductal carcinoma, gastric carcinoma, squamous cell carcinoma, basal cell carcinoma, and soft tissue sarcoma. Additional neoplastic disorders can be found in, for example, Isselbacher et al. (1994) Harrison S Principles of Internal Medicine 1814-1877, which is herein incorporated by reference.

Delivery of a therapeutically effective activity of a radiopharmaceutical of the invention can be obtained via administration of a pharmaceutical composition comprising a therapeutically effective activity of this agent. By "therapeutically effective activity" or "dose" is meant a concentration of a labeled construct of the invention that is sufficient to elicit the desired therapeutic effect according to the various methods of treatment described herein. Accordingly, in one embodiment, a therapeutically effective activity is an activity effective to treat cancer, such as inhibiting or slowing growth of cancerous tissue. The therapeutically effective dosage of any specific compound will vary somewhat from compound to compound, patient to patient, and will depend upon the condition of the patient and the route of delivery. The effective activity of any particular compound would be expected to vary according to the weight, sex, age, and medical history of the subject. Other factors which influence the effective dose can include, but are not limited to, the severity of the patient's condition, the disease or disorder being treated, the stability of the compound according to the invention, and, if appropriate, any additional antineoplastic therapeutic agent being administered with the compound of the invention. Methods to determine efficacy and dosage are known to those skilled in the art. See, for example, Isselbacher et al. (1996) Harrison S Principles of Internal Medicine 13 ed., 1814-1882, herein incorporated by reference.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods exhibit large therapeutic indices. A therapeutically effective dose can be estimated initially from cell culture assays. Also, a dose can be formulated in animal models to achieve a circulating plasma concentration range that includes the IC50 (i.e., the concentration of the compound of the invention, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, an effective dose of a composition comprising a compound of the invention can be administered to a patient to identify, image or localize cancerous cells and tumors. In some embodiments, a compound of the invention can be administered to a patient once. In certain embodiments, an effective dose of a composition comprising a compound of the invention can be administered to a patient repeatedly. Patients can be administered a therapeutic amount of a composition comprising a compound of the invention, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising a compound of the invention can be administered over a period of time, such as over a 5 minute, 10 minute, 15 minute, 20 minute, or 25 minute period. If warranted, the administration can be repeated, for example, on a regular basis, such as hourly for 3 hours, 6 hours, 12 hours or longer or such as biweekly (i.e., every two weeks) for one month, two months, three months, four months or longer. In some instances, after an initial treatment regimen, the treatments can be administered on a less frequent basis. For example, after administration biweekly for three months, administration can be repeated once per month, for six months or a year or longer.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the compound of the invention.

In certain embodiments, an effective dose of a composition comprising a compound of the invention can be administered to treat, inhibit, or prevent a cancer in a patient. In certain embodiments, an effective dose of a composition comprising a compound of the invention as described herein can be administered to a patient once. In certain embodiments, an effective dose of a composition comprising a compound of the invention can be administered to a patient repeatedly. In certain embodiments, an effective dose of a composition comprising a compound of the invention can be administered to a patient via skin patches, instillation into urinary bladder through urethral, or vaginal channel through ring implantation. Patients can be administered a therapeutic amount of a composition comprising a compound of the invention, such as, e.g. 0.0001 mg/kg, 0.001 mg/kg, 0.01 mg/kg, 0.05 mg/kg, 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising a compound of the invention can be administered over a period of time, such as over a 5 minute, 10 minute, 15 minute, 20 minute, or 25 minute period. If warranted, the administration can be repeated, for example, on a regular basis, such as hourly for 3 hours, 6 hours, 12 hours or longer or such as biweekly (i.e., every two weeks) for one month, two months, three months, four months or longer. In some instances, after an initial treatment regimen, the treatments can be administered on a less frequent basis. For example, after administration biweekly for three months, administration can be repeated once per month, for six months or a year or longer. Administration of a composition comprising compound of the invention can reduce levels of a biomarker or a symptom of cancer, e.g. the size of a tumor or the rate of growth of a tumor by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the compound of the invention.

As used herein "radiation" is intended to include any treatment of a neoplastic cell or subject by neutrons, electrons, or other type of ionizing radiation. Such radiations include, but are not limited to, X-ray, gamma-radiation, or heavy ion particles, such as alpha or beta particles. Additionally, the radiation can be radioactive. The means for irradiating neoplastic cells in a subject are well known in the art and include, for example, external beam therapy, and brachytherapy. Uptake of Dual Nuclear/NIR Agents either alone or with therapeutic moieties can be accomplished in normal cells by the attachment of a targeting ligand. Based upon the unique and attractive pharmacokinetic properties of Dual Nuclear/NIR Agents (i.e., washout from systemic circulation but retained in tumors), the inventors propose that this compound can be chemically conjugated to various radionuclides for the imaging and treatment of metastatic tumor growth in live animals and that this technology can be expanded to human use for a number of attractive applications.

Embodiments of the present invention related to the use of carbocyanine dyes, particularly, Dual Nuclear/NIR Agents, include but not limited to study the in situ pharmacokinetics and pharmacodynamics of pharmaceuticals in live animals and humans. This application is important and significant because until now, pharmacokinetics and pharmacodynamics are measured using bodily fluids available for detection. The ability of the Dual Nuclear/NIR Agents to be specifically taken up by tumor tissues could lead to methods of determining the in situ pharmacokinetics and pharmacodynamics of clinically useful imaging agents and radiotherapeutic drugs in the body and at tumor sites. Dual Nuclear/NIR Agents can be used as a chemical tag for tumor cells. The tagged tumor cells can be isolated by FACS sorting. The isolated tumor cells from biological fluids can be further characterized. Dual Nuclear/NIR Agents can also be used to tag stem cells, putative tumor stem cells or any biologicals that can penetrate organ, tissue or cellular compartment for improved real-time imaging.

Dual Nuclear/NIR Agents can be chemically conjugated to drugs, organic and inorganic molecules, or radionuclides with ligands known to bind to normal cells for normal organ, tissue repair and regeneration. Because of its unique property, it can be visualized at the site of drug action and the biologic response of the tissues and organs to these reagents can be assessed and correlated.

Dual Nuclear/NIR Agents can be used as an agent to image and treat patients on a personalized basis. It is known that drug accumulation and metabolism in individual patients are different, but unfortunately it is difficult to monitor the pharmacokinetic and pharmacodynamic properties of drugs with desirable precision. Dual Nuclear/NIR Agents conjugation to pharmaceuticals could solve this problem because this compound can be imaged at tumor sites, thus providing vital information on the pharmacokinetic and pharmacodynamic properties of drugs.

Dual Nuclear/NIR Agents can be used to tag circulating stem cells for the assessment of stem cell grafting of bone marrow or other vital organs. Normal cells can have a low rate of uptake and this can be improved by the use of internalized cell surface ligand in conjugation with Dual Nuclear/NIR Agents, which could potentially increase the amount of uptake into stem cell populations.

This same concept can be applied by the conjugation of Dual Nuclear/NIR Agents to other tissue and organ-specific cell surface molecules for potential imaging and cytotoxicity purposes. For example, Dual Nuclear/NIR Agents can be guided into human BPH tissues using a prostate cell surface ligand plus cytotoxic drug conjugates for tumor ablation.

Likewise, a number of benign tumors which can be difficult for surgical approaches can also be candidates for selective tumor ablation using Dual Nuclear/NIR Agents as the imaging and cytotoxic agent.

Various embodiments provide for pharmaceutical composition comprising an imaging agent of the present invention and a pharmaceutically acceptable carrier.

In one aspect of the present invention, pharmaceutical compositions are provided, which comprise one or more (e.g. 1, 2, 3, 4, 5, 6, 7, 8, 9, 10, or more) of the compounds described herein (or a prodrug, pharmaceutically acceptable salt, or other pharmaceutically acceptable form thereof), and optionally a pharmaceutically acceptable excipient. In certain embodiments, these compositions optionally further comprise one or more additional therapeutic agents. Alternatively, a compound of the invention can be administered to a patient in need thereof in combination with the administration of one or more other therapeutic agents. For example, in the regulation of skin pigmentation, an additional therapeutic agents for conjoint administration or inclusion in a pharmaceutical composition with a compound of this invention can be an approved skin pigmentation agent.

Amount of the compound or compounds in the pharmaceutical composition can be based on weight, moles, or volume. In some embodiments, the pharmaceutical composition comprises at least 0.0001% compounds of the invention. In some embodiments, the pharmaceutical composition comprises at least 0.1% compounds of the invention. In some embodiments, the pharmaceutical composition comprises at least 0.5% compounds of the invention. In some embodiments, the pharmaceutical composition comprises at least 1% compounds of the invention. In some embodiments, the pharmaceutical composition comprises at least 2% compounds of the invention. In some embodiments, the pharmaceutical composition comprises at least 3% compounds of the invention. In some embodiments, the pharmaceutical composition comprises at least 4% compounds of the invention. In some embodiments, the pharmaceutical composition comprises at least 5% compounds of the invention. In some embodiments, the pharmaceutical composition comprises at least 10% compounds of the invention. In some embodiments, the pharmaceutical composition comprises 0.01%-99% of the compounds of the invention. In some embodiments, the pharmaceutical composition comprises 0.05%-90% of the compounds of the invention. In some embodiments, the pharmaceutical composition comprises 0.1%-85% of the compounds of the invention. In some embodiments, the pharmaceutical composition comprises 0.5%-80% of the compounds of the invention. In some embodiments, the pharmaceutical composition comprises 1%-75% of the compounds of the invention. In some embodiments, the pharmaceutical composition comprises 2%-70% of the compounds of the invention. In some embodiments, the pharmaceutical composition comprises 3%-65% of the compounds of the invention. In some embodiments, the pharmaceutical composition comprises 4%-60% of the compounds of the invention. In some embodiments, the pharmaceutical composition comprises 5%-50% of the compounds of the invention.

Various embodiments provide for a method of identifying, imaging or localizing cancerous cells and tumors in a patient in need thereof. The method can comprise providing the Dual Nuclear/NIR Agent of the present invention; administering the Dual Nuclear/NIR Agent to the patient; and performing PET scan or a SPECT scan. In various embodiments, performing the PET scan or the SPECT scan is at about 6 to 48 hours post injection.

Various embodiments provide for a method of identifying, imaging or localizing cancerous cells and tumors in a patient in need thereof. The method can comprise providing the Dual Nuclear/NIR Agent of the present invention; administering the Dual Nuclear/NIR Agent to the patient; and imaging the tumor location within the NIR spectral region. In various embodiments, imaging the tumor is performed about 6 to 48 hours post injection.

Various embodiments provide for a method of treating or preventing cancer in a patient in need thereof. The method can comprise providing the Dual Nuclear/NIR Agent of the present invention that is dual-labeled with a positron or gamma emitting radioisotope and a beta or alpha radionuclide; and administering the Dual Nuclear/NIR Agent to the patient.

Various embodiments provide for a method of treating or preventing cancer in a patient in need thereof. The method can comprise providing the Dual Nuclear/NIR Agent of the present invention that is co-labeled with a positron or gamma emitting radioisotope and a CT selected from the group consisting of a radiolabeled or non-radiolabeled cytotoxic drug, antibody, toxin, aptamer, siRNA, antisense construct and microRNA; and administering the Dual Nuclear/NIR Agent to the patient.

The compositions and methods described herein can be administered to a subject having or diagnosed as having cancer. In some embodiments, the methods described herein comprise administering an amount of compositions described herein to a subject in order to treat or prevent cancer. For example, as compared with an equivalent untreated control, a reduction of a symptom by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral or parenteral routes, including intravenous, intramuscular, subcutaneous, transdermal, airway (aerosol), pulmonary, or intratumoral. Administration can be local or systemic.

The term "effective amount" as used herein refers to the amount compound of the instant invention needed to alleviate the cancer, and relates to a sufficient amount of pharmacological composition to provide the desired effect. The term "therapeutically effective amount" therefore refers to an amount of a compound of the invention that is sufficient to cause a particular anti-cancer effect when administered to a typical subject. An effective amount as used herein, in various contexts, would also include an amount sufficient to delay the development of a symptom of the disease, alter the course of a symptom disease (for example but not limited to, slow the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods exhibit large therapeutic indices. A therapeutically effective dose can be estimated initially from cell culture assays. Also, a dose can be formulated in animal models to achieve a circulating plasma concentration range that includes the IC50 (i.e., the concentration of the compound of the invention, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inhibition of cancer cell proliferation, among others. The dosage can be determined by a physician and adjusted, as necessary, to suit observed effects of the treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the compound of the invention.

Various embodiments provide for a method for the detection of a molecule in tumor or normal cells, or tumor or normal tissue. The method can comprise providing the Dual Nuclear/NIR Agent of the present invention; conjugating or complexing the molecule with the Dual Nuclear/NIR Agent, wherein the molecule is selected from the group consisting of a drug, a radionuclide, a microorganism, a substrate, a metabolite, a gene, gene transcript, gene modifier, or gene product; and imaging the tumor or normal cells, or tumor or normal tissue.

Various embodiments provide for a method of conducting in situ pharmacokinetic and pharmacodynamic analyses of the Dual Nuclear/NIR Agent of the present invention and its drug or radionuclide payload in a tumor or normal cell or tissue. The method can comprise providing the Dual Nuclear/NIR Agent of the present invention and its drug or radionuclide payload; contacting the Dual Nuclear/NIR Agent of the present invention and its drug or radionuclide payload with the tumor or normal cell or tissue; and imaging the tumor or normal cell or tissue.

Various embodiments provide for a method of conducting surgical removal of a tumor in a patient in need thereof. The method can comprise providing the Dual Nuclear/NIR Agent of the present invention; administering the Dual Nuclear/NIR Agent to the patient; imaging the patient to detect cancer cells in situ at surgical margin at the time of surgery; and performing the surgical removal of the tumor.

Various embodiments provide for a method to tag a cell, microorganism and small molecule. The method can comprise providing the Dual Nuclear/NIR Agent of the present invention; contacting the Dual Nuclear/NIR Agent with the cell, microorganism, or small molecule; and imaging the Dual Nuclear/NIR Agent with the cell, microorganism, or small molecule to follow its movements in live subjects.

Various embodiments provide for a method of studying cancer metastases in conventional or transgenic animal. The method can comprise providing the Dual Nuclear/NIR Agent of the present invention or its conjugate; injecting the Dual Nuclear/NIR Agent or its conjugate into a conventional or transgenic animal bearing either a mouse or human tumor; and monitoring the tumor by using PET, SPECT, or optical imaging technology.

Various embodiments of the present invention also provide for methods of synthesizing and radiolabeling the Dual Nuclear/NIR Agents; for example, PC-001, PC-002, PC-003, PC-004, PC-005, PC-006 and PC-007. In some embodiments, the methods of synthesizing and radiolabeling PC-001, PC-002, PC-003, PC-004, PC-005, PC-006 and PC-007 are described in more detail in the schemes 1-8 and the examples below.

In some embodiments, the invention can be described by any one of the numbered paragraph:

1. A Dual Nuclear/NIR Agent having a structure according to one of the following formulas:

Formula I

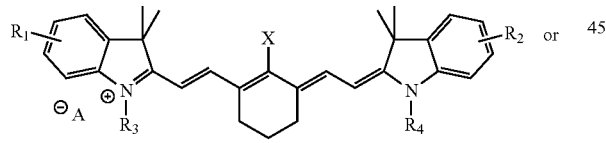

or

Formula II

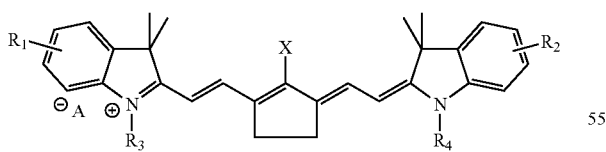

wherein $R_1$ and $R_2$ are each independently selected from the group consisting of radioisotopes I-125, I-123, I-131, I-124, F-18, hydrogen, sulfonato, an electron withdrawing group (EWG), an electron donating group (EDG), and are each independently attached at any of the aromatic ring positions;

$R_3$ and $R_4$ are independently selected from the group consisting of hydrogen, alkyl, aryl, aralkyl, alkylsulfonato, alkylcarboxylic, alkylamino, ω-alkylaminium, ω-alkynyl, PEGyl, PEGylcarboxylate, ω-PEGylaminium, ω-acyl-NH—CR, ω-acyl-lysine-CR, ω-acyl-triazole-CR, ω-PEGylcarboxyl-NH—CR, ω-PEGylcarboxyl-lysine-CR, and ω-PEGylcarboxyl-triazole-CR;

X is selected from the group consisting of a hydrogen, halogen, I-125, I-123, I-131, I-124, F-18, CN, Me, OH, 4-O-Ph-CH$_2$CH$_2$COOH, 4-O-Ph-NH—CR, NH—CR, 4-S-Ph-NH—CR, ω-iminoacyl-NH—CR, ω-aminoacyl-lysine-CR, ω-iminoacyl-triazole-CR, 4-O-Ph-CH$_2$CH$_2$COOCT, 4-O-Ph-O-CT, 4-S-Ph-O-CT, and ω-iminoacyl-O-CT, wherein CR is selected from the group consisting of a metal chelating agent, a radioactive or nonradioactive metal complex, a radioiodine or iodine labeled Bolten-Hunter reagent, and a radioiodine or iodine labeled tyrosine moiety, wherein the metal is selected from the group consisting of Cu-64, In-111, Tc-99m, Ga-68, Y-90, Lu-177, Re-188, At-211, Bi-213, Ac-225 and their nonradioactive counterparts, wherein CT is selected from the group consisting of radiolabeled or non-radiolabeled cytotoxic drugs, antibodies, toxins, aptamers, siRNA, antisense constructs and microRNAs; and counteranion A is selected from the group consisting of iodide, bromide, arylsulfonato, alkylsulfonato, tetrafluoroborate, chloride, and a pharmaceutically acceptable anion.

2. The Dual Nuclear/NIR Agent of paragraph 1, having one of the following structures:

PC-001

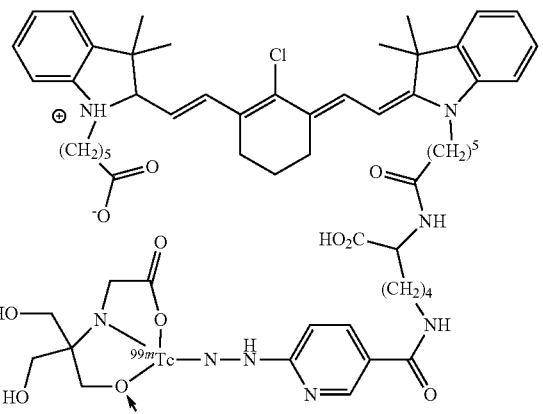

PC-002

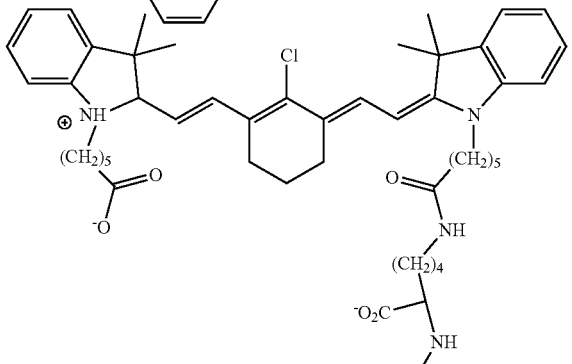

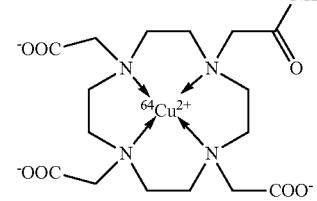

-continued
PC-003
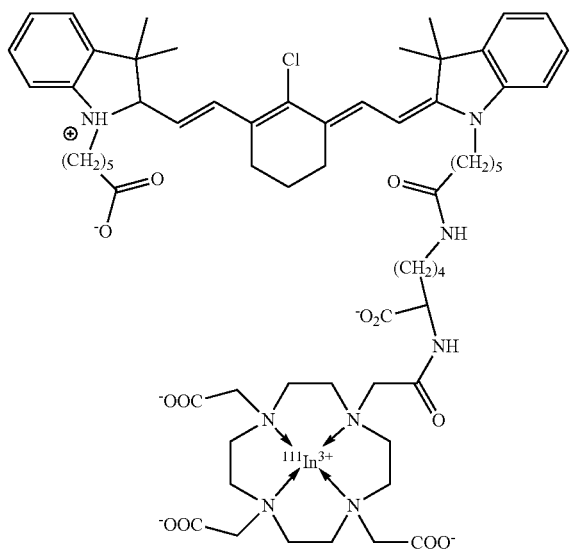
PC-004
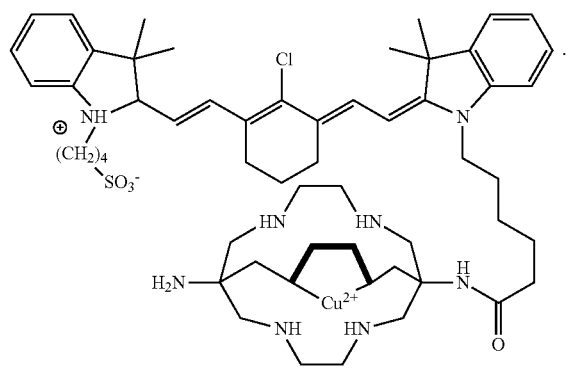
3. The Dual Nuclear/NIR Agent of paragraph 1, having the following structure:
4. The Dual Nuclear/NIR Agent of paragraph 1, having the following structure:
PC-006
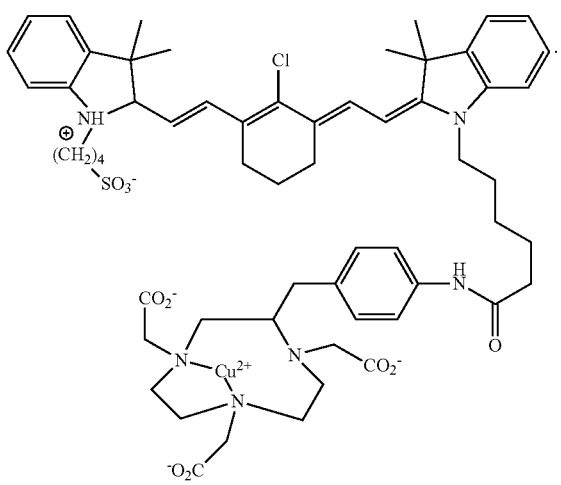
5. The Dual Nuclear/NIR Agent of paragraph 1, having the following structure:
PC-007
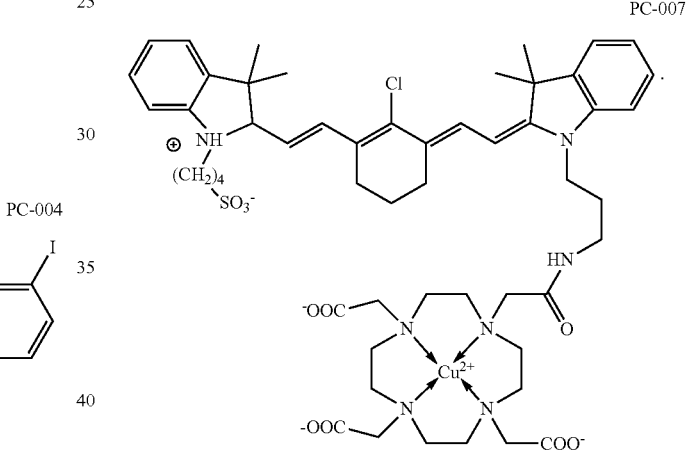
6. The Dual Nuclear/NIR Agent of paragraph 1, having one of the following structures:
PC-1001
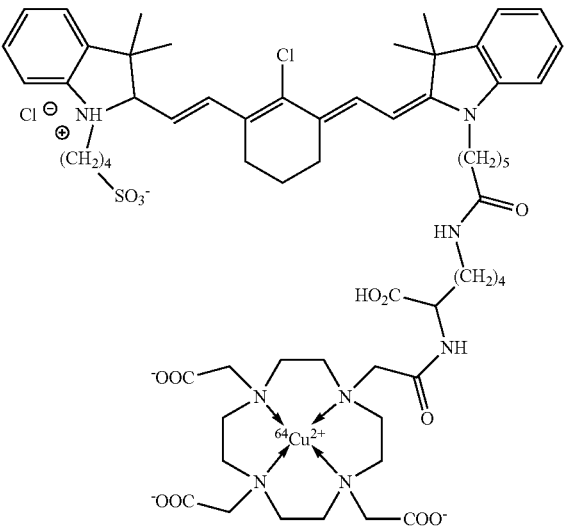

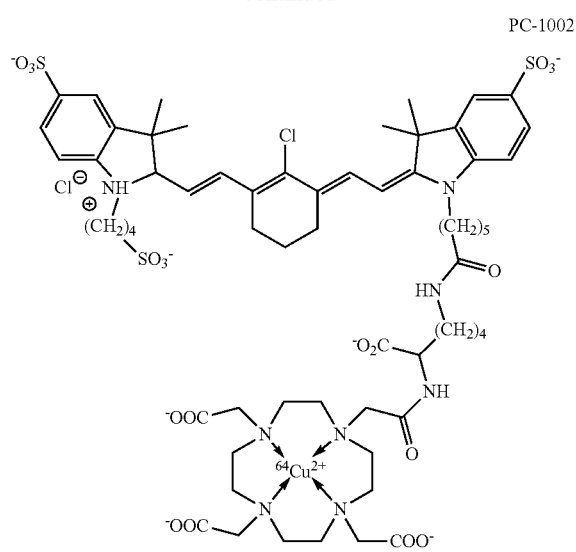
PC-1002
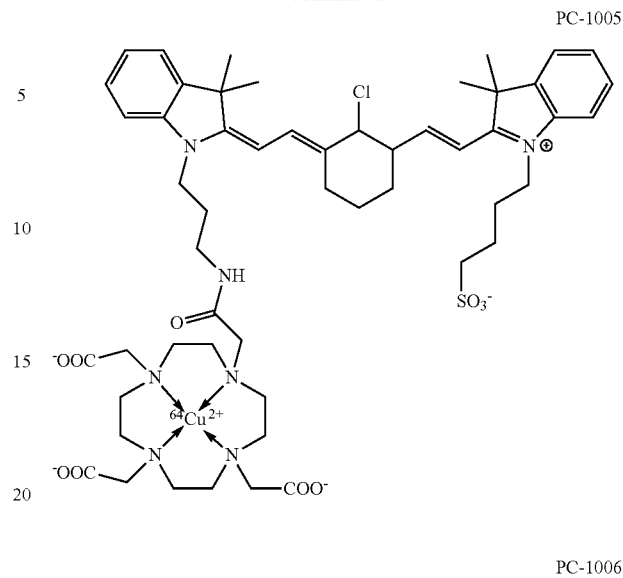
PC-1005
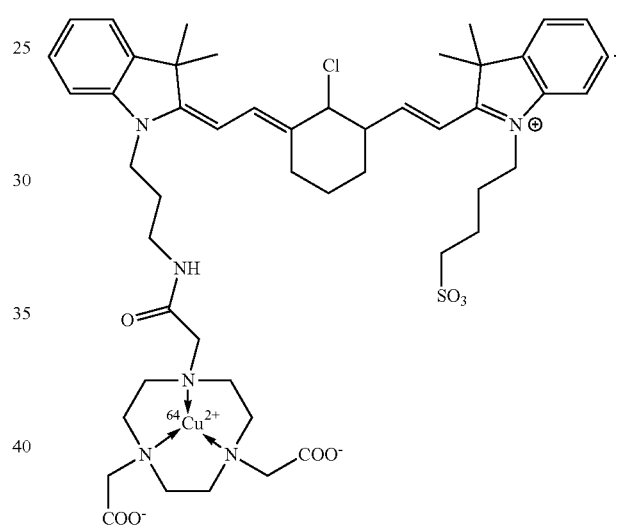
PC-1006
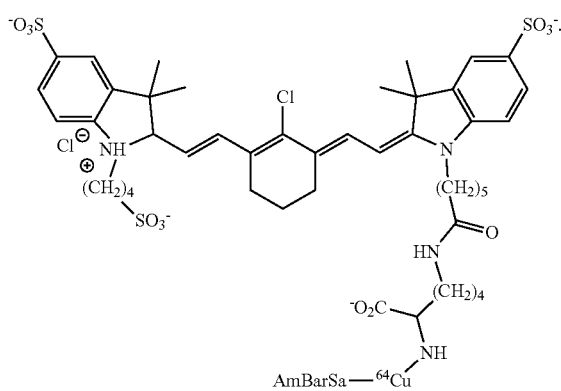
PC-1003
8. The Dual Nuclear/NIR Agent of paragraph 1, having one of the following structures:
7. The Dual Nuclear/NIR Agent of paragraph 1, having one of the following structures:
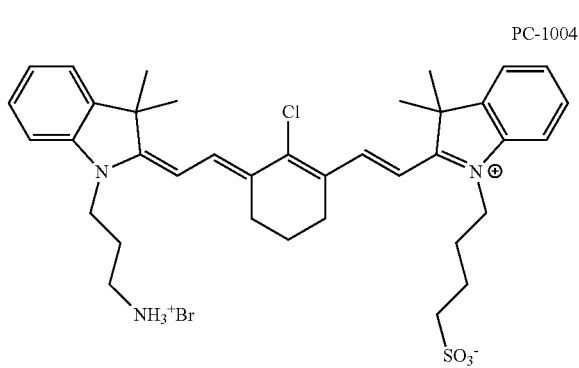
PC-1004
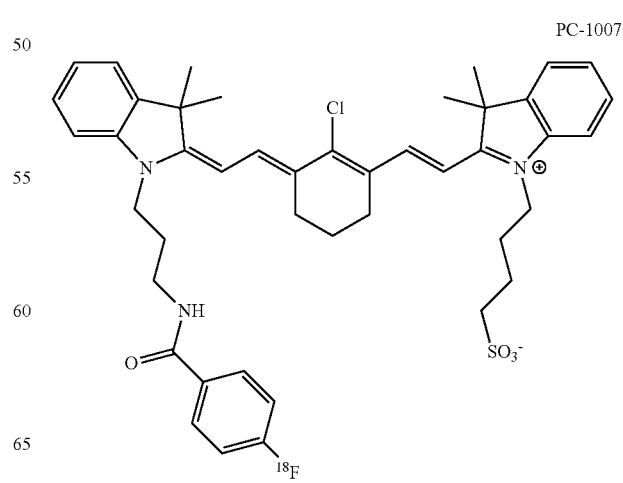
PC-1007

PC-1008

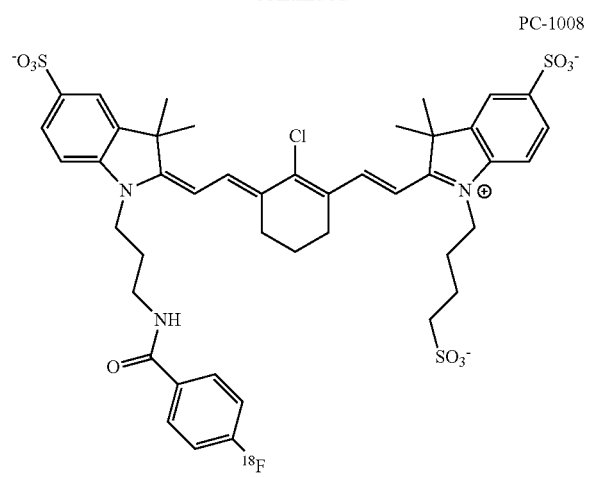

PC-1011

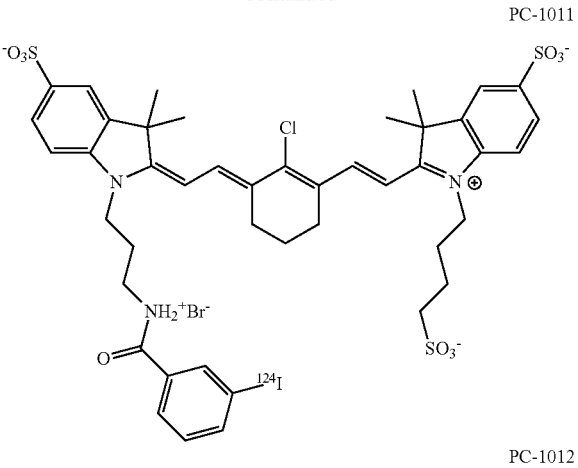

PC-1009

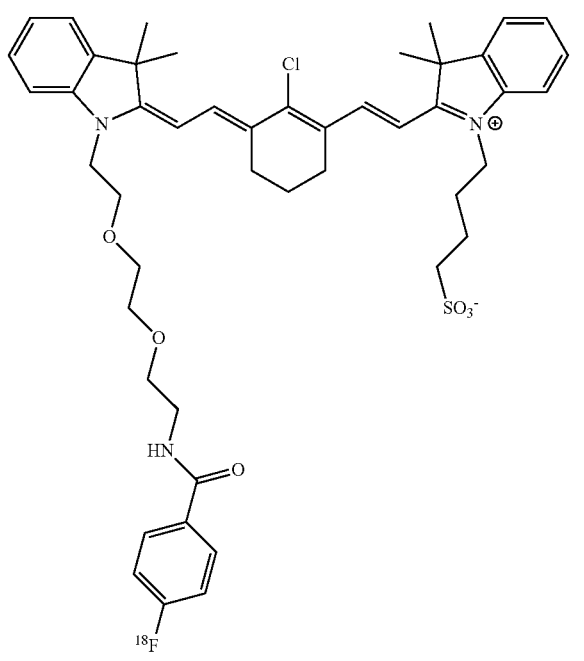

PC-1012

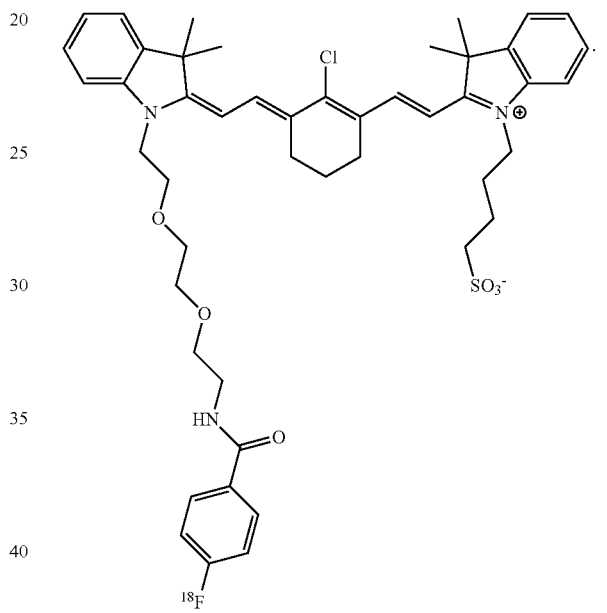

PC-1010

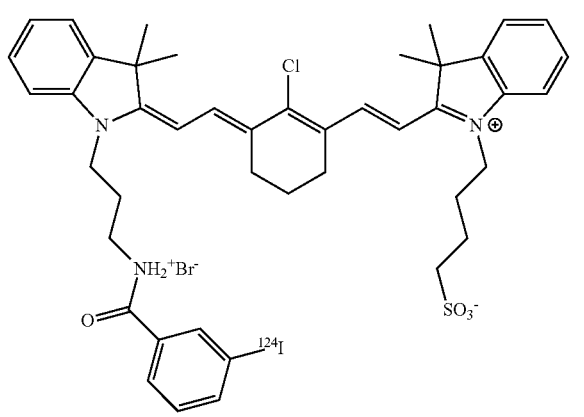

9. A process of manufacturing the Dual Nuclear/NIR Agent of paragraph 1, comprising:
   providing a compound of Formula I or Formula II, wherein $R_3$ and $R_4$ are each independently in each instance, $(CH_2)_m R_A$, where m is an integer from 1 to 12, $R_A$ is independently $CH_3$, $NH_2$, SH, COOH, $SO_3H$, OH, halogen and CO—N-hydroxysuccinimide;
   reacting the compound with N-hydroxysuccimide to form a monocuccinimide ester of the compound;
   reacting monocuccinimide ester of the compound with $N^\omega$-(t-butoxyhydrazinonicotinyl)-lysine to form a labeling precursor compound; and
   reacting the labeling precursor compound with $^{99m}TcO_4^-$ to form the Dual Nuclear/NIR Agent of paragraph 1.

10. A process of manufacturing the Dual Nuclear/NIR Agent of paragraph 1, comprising:
    providing a compound of Formula I or Formula II, wherein $R_3$ and $R_4$ are each independently in each instance, $(CH_2)_m R_A$, where m is an integer from 1 to 12, $R_A$ is independently $CH_3$, $NH_2$, SH, COOH, $SO_3H$, OH, halogen and CO—N-hydroxysuccinimide;
    reacting the compound with N-hydroxysuccimide to form a monocuccinimide ester of the compound;
    reacting monocuccinimide ester of the compound with N-α-tBoc-lysine for form a conjugated monocuccinimide ester of the compound;

reacting the monocuccinimide ester of the compound with TFA to yield the compound-Lys;
coupling of the compound-Lys with DOTA-Sulfo-NHS, in acetonitrile-water to yield the compound-DOTA;
adding $^{64}$CuCl$_2$ or adding $^{111}$InCl$_3$ to obtain Dual Nuclear/NIR Agent of paragraph 1.

11. A process of manufacturing the Dual Nuclear/NIR Agent of paragraph 1, comprising: using a click chemistry method.

12. A process of manufacturing the Dual Nuclear/NIR Agent of paragraph 1, comprising: using a Staudinger ligation method.

13. A pharmaceutical composition comprising the Dual Nuclear/NIR Agent according to paragraph 1 and at least one pharmaceutically acceptable carrier.

14. A method of identifying, imaging or localizing cancerous cells and tumors in a patient in need thereof, comprising:
providing the Dual Nuclear/NIR Agent of paragraph 1;
administering the Dual Nuclear/NIR Agent to the patient; and
performing a PET scan or a SPECT scan.

15. A method of identifying, imaging or localizing cancerous cells and tumors in a patient in need thereof, comprising:
providing the Dual Nuclear/NIR Agent of paragraph 1;
administering the Dual Nuclear/NIR Agent to the patient; and
imaging the tumor location within the NIR spectral region.

16. A method of treatment, inhibition, or prevention of a cancer in a patient in need thereof, comprising:
providing the Dual Nuclear/NIR Agent of paragraph 1, that is dual-labeled with a positron or gamma emitting radioisotope and a beta or alpha radionuclide; and
administering the dual-labeled Dual Nuclear/NIR Agent to the patient.

17. A method of treatment, inhibition, or prevention of cancer in a patient in need thereof, comprising:
providing the Dual Nuclear/NIR Agent of paragraph 1, that is co-labeled with a positron or gamma emitting radioisotope and a CT selected from the group consisting of a radiolabeled or non-radiolabeled cytotoxic drug, antibody, toxin, aptamer, siRNA, antisense construct and microRNA; and
administering the co-labeled Dual Nuclear/NIR Agent to the patient.

18. A method for the detection of a molecule in tumor or normal cells, or tumor or normal tissue, comprising:
providing the Dual Nuclear/NIR Agent of paragraph 1;
conjugating or complexing the molecule with the Dual Nuclear/NIR Agent, wherein the molecule is selected from the group consisting of a drug, a radionuclide, a microorganism, a substrate, a metabolite, a gene, gene transcript, gene modifier, or gene product; and
imaging the tumor or normal cells, or tumor or normal tissue.

19. A method of conducting in situ pharmacokinetic and pharmacodynamic analyses of the Dual Nuclear/NIR Agent of paragraph 1 and its drug or radionuclide payload in a tumor or normal cell or tissue, comprising:
providing the Dual Nuclear/NIR Agent of paragraph 1 and its drug or radionuclide payload;
contacting the Dual Nuclear/NIR Agent of paragraph 1 and its drug or radionuclide payload with the tumor or normal cell or tissue; and
imaging the tumor or normal cell or tissue.

20. A method of conducting surgical removal of a tumor in a patient in need thereof, comprising:
providing the Dual Nuclear/NIR Agent of paragraph 1;
administering the Dual Nuclear/NIR Agent to the patient;
imaging the patient to detect cancer cells in situ at a surgical margin at the time of surgery; and
performing the surgical removal of the tumor.

21. The method of paragraph 20 further comprising administering ICG.

22. A method to tag a cell, microorganism and small molecule, comprising:
providing the Dual Nuclear/NIR Agent of paragraph 1;
contacting the Dual Nuclear/NIR Agent with the cell, microorganism, or small molecule; and
imaging the cell, microorganism, or small molecule to follow its movements in live subjects.

23. A method of studying cancer metastases in a conventional or transgenic animal, comprising:
providing the Dual Nuclear/NIR Agent of paragraph 1 or its conjugate;
injecting the Dual Nuclear/NIR Agent or its conjugate into a conventional or transgenic animal bearing either a mouse or human tumor; and
monitoring the tumor by using PET, SPECT, optical imaging technology, or a combination thereof.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Method of Synthesizing Dual Nuclear/NIR Agents

Schemes 1, 2, 3, 4, 5, 6, 7, and 8, are examples of synthetic schemes by which compounds of Formula 1 can be synthesized.

Example 1

Preparation of PC-001 (9)

Scheme 1 depicts a reaction pathway for the synthesis and labeling $^{99m}$Tc labeled SPECT probe PC-001.

Scheme 1

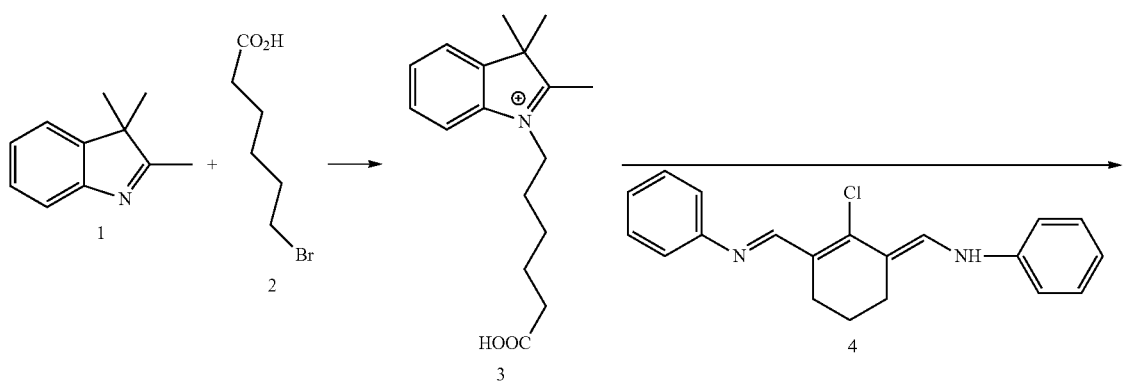

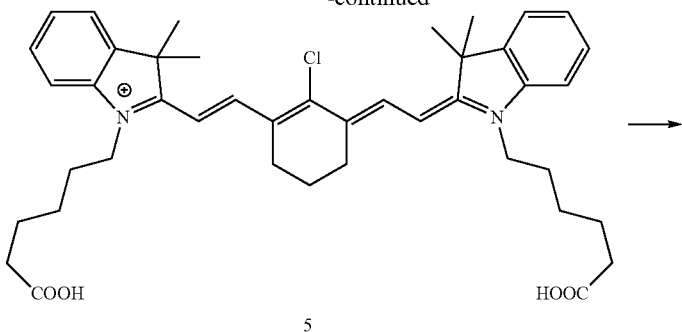
5
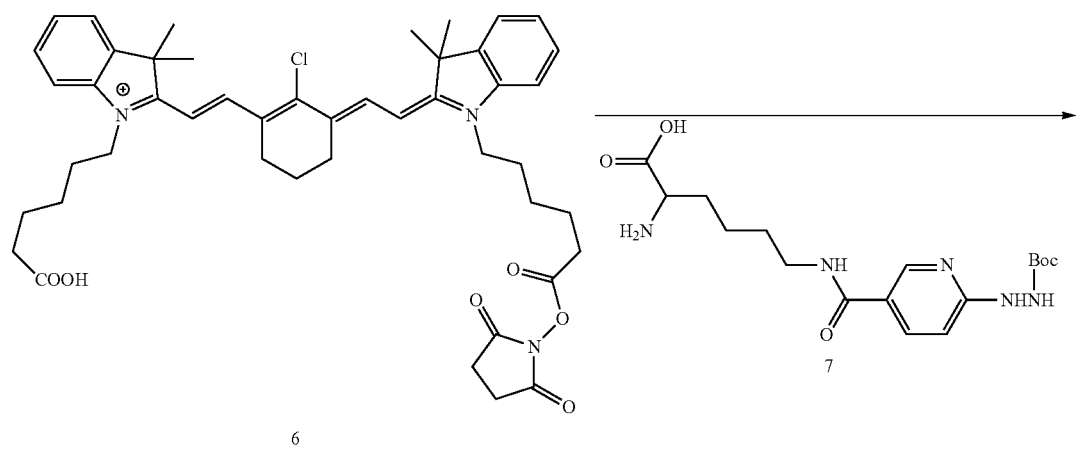
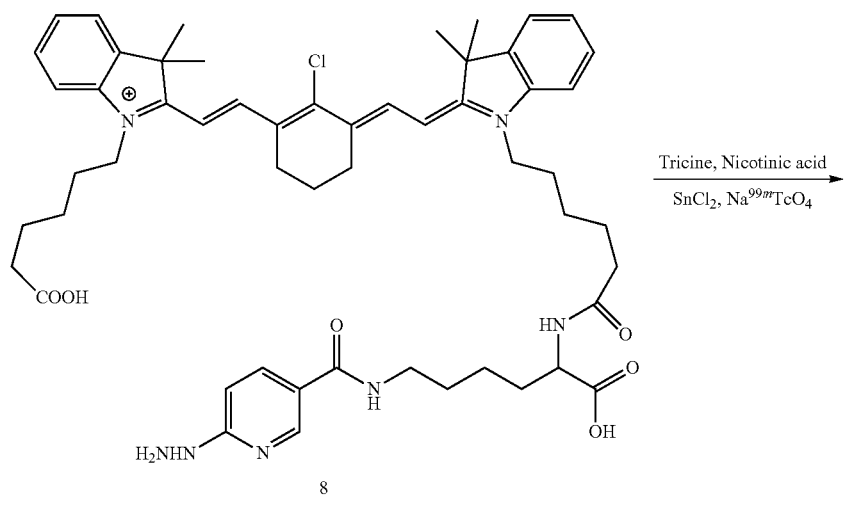

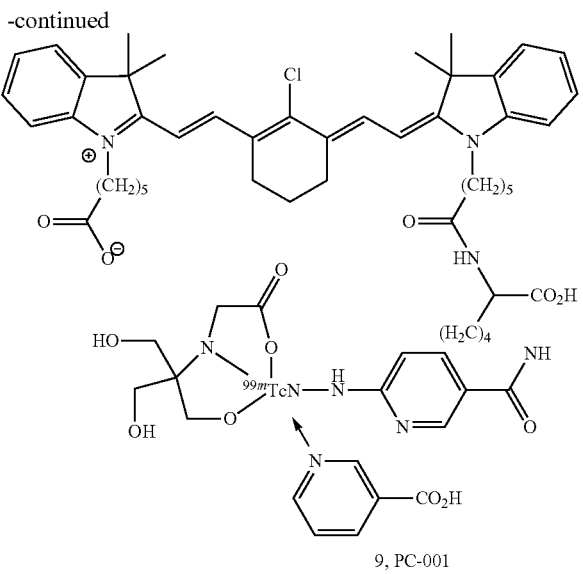

9, PC-001

N-[(3-(Anilinomethylene)-2-chloro-1-cyclohexen-1-yl) methylene]aniline monohydrochloride 4,2,3,3-Trimethylindolenine 1,6-Bromohexanoic acid 2, Fmoc-Lys-OH hydrochloride were purchased from Sigma-Aldrich Chemicals. N,N'-Dicyclohexylcarbodiimide (DCC), N-hydroxysuccinimide and sodium acetate were purchased from Arcos Chemicals. Boc-HNA-OSu was purchase from Solulink. Compound 5 and $N^\omega$-(t-butoxyhydrazinonicotinyl)-lysine 7 were synthesized according to literature procedures. Chemicals were used without further purification. $Na^{99m}TcO_4$ was obtained from Cardinal Health INC (Charlottesville, Va.). Semipreparative reversed-phase high-performance liquid chromatography (RP-HPLC) was performed with an Apollo C18 reversed-phase column (5μ, 250×10 mm) on a Varian system with ABI Spectroflow 783 UV detector and Bioscan NaI solid scintillation Flow Count Radio-HPLC detector. The mobile phase was changed from 30% Solvent A (0.1% TFA in water) and 70% Solvent B (0.1% TFA in 80% aqueous acetonitrile) to 100% Solvent B at 30 min at a flow rate 3 mL/min. MALDI-TOF mass spectroscopy analysis was performed on samples of peptide products at the W.M. Keck Biomedical Mass Spectrometry Laboratory at the University of Virginia (UVa) and the data was obtained on a Bruker Daltonics system (Billerica, Mass.).

Synthesis of 8: An ethanol solution of 2,3,3-trimethylindolenine 1 and 6-bromohexanoic acid 2 was heated at 110° C. for 8 hrs to produce 1-(5'-carboxypentyl)-2,3,3-trimethylindolinium bromide 3. The compound 3 (100 mg, 0.28 mmol) was mixed with N-[5-anilino-3-chloro-2,4-(propane-1',3'-diyl)-2,4-pentadien-1-ylidene]anilinium chloride 4 (50 mg, 0.14 mmol) and sodium acetate (50 mg, 0.36 mmol) in 20 mL of ethanol and the solution was refluxed for 30 min. The solution was then concentrated to dryness and the residue was triturated twice with 5 ml of 2N HCl. The residue was dried under vacuum to yield 5 as dark solid. To a solution of 5 (200 mg, 0.28 mmol) and N-hydroxysuccinimide (32 mg, 0.28 mmol) in methylene chloride (140 mL) was added 57.3 mg (0.28 mmol) of DCC. The mixture was stirred for 12 h at room temperature and the precipitates were removed by filtration. Monosuccinimide ester 6 was obtained by removing methylene chloride with a rotary vacuum evaporator. Monosuccinimide ester 6 (100 mg, 0.12 mmol) was conjugated with Nω-(t-butoxyhydrazinonicotinyl)-lysine 7 (56 mg, 0.15 mmol) in 4 mL of acetonitrile-sodium borate buffer (0.1N, pH 8.5) (50/50, v/v) by incubating at 4° C. overnight. TFA 2 mL was then added and the mixture was incubated at RT for 2 h to remove the t-butoxyl protecting group. The solvent was removed under reduced pressure by rotary evaporator. The concentrated residue was purified by HPLC to obtain the labeling precursor, 2-((E)-2-((E)-3-((E)-2-(1-(6-(1-carboxy-5-(6-hydrazinylnicotinamido)pentylamino)-6-oxohexyl)-3,3-dimethylindolin-2-ylidene)ethylidene)-2-chlorocyclohex-1-enyl)vinyl)-1-(5-carboxypentyl)-3,3-dimethyl-3H-indolium 8 mass spectrum (MALDI-TOF), m/z 946.5 (M+H).

PC-001 (9): To a 1.5 mL vial was consecutively added 100 ug of 8 200 uL of Ethanol, 200 uL of tricine solution (30 mg/mL in water), 100 uL of nicotinic acid solution (10 mg/mL in water), 30mCi of 99 mTcO4-solution, and 25 uL of SnCl2 solution (3.0 mg/mL in Ethanol). The reaction mixture was stirred by shaking and heated at 60° C. for 15 min. After being cooled to room temperature for 10 min, the reaction mixture was purified by HPLC as described in the general methods. Compound 9 was obtained at a retention time of 10.7 min with a radiochemical yield higher than 90%.

Example 2

Preparation of PC-002 and PC-003

Scheme 2 depicts a reaction pathway for the synthesis and labeling $^{64}$Cu labeled PET probe PC-002 and $^{111}$In labeled SPECT probe PC-003.

Scheme 2
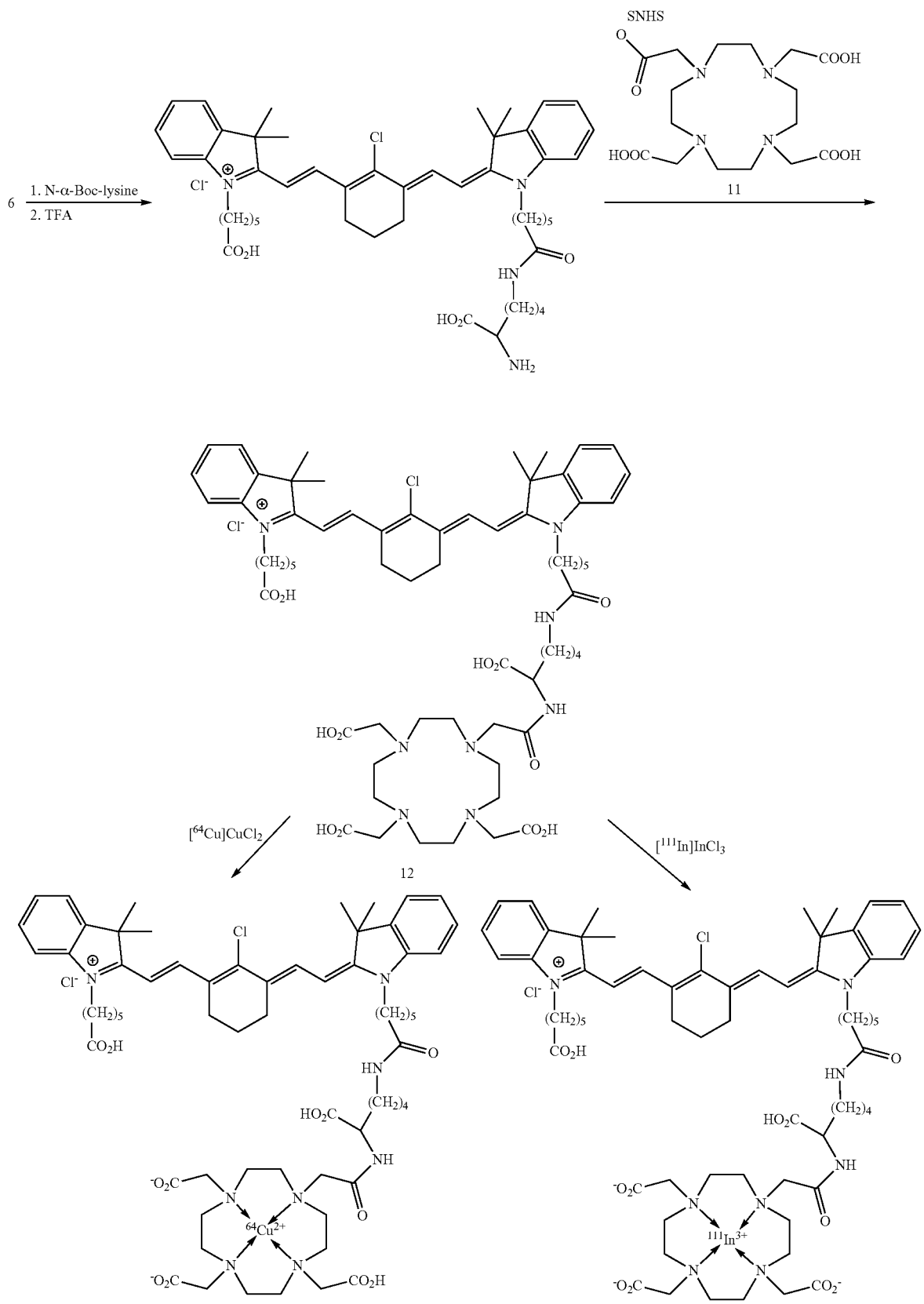

Synthesis of 12: 6 was synthesized according to scheme 1. The 6 was then conjugated with N-α-tBoc-lysine, followed by treatment of TFA to yield 10. Coupling of 10 with DOTA-Sulfo-NHS, in acetonitrile-water at 4° C. and pH 8.5 overnight, yield 12, mass spectrum (MALDI-TOF), m/z 1197.8 (M+H).

PC-002 (13): The radiolabeling was accomplished by addition of 0.5-2 mCi of 64CuCl$_2$ to 50-100 mg of 12 in 0.1N ammonium acetate (pH 5.5) buffer and the mixture was incubated at 40° C. for 20 minutes. The mixture was injected as is for RP-HPLC purification. The column elute was monitored by UV absorbance at 254 nm and with a gamma detector. The mobile phase was changed from 40% Solvent A (0.1% TFA in water) and 60% Solvent B (0.1% TFA in 80% aqueous acetonitrile) to 100% Solvent B at 30 min at a flow rate 3 mL/min. PC-002 was obtained at a retention time of 14.5 min with a radiochemical yield higher than 90%.

A method of synthesizing and radiolabeling PC-003 (Scheme 2): it involves: heating an ethanol solution of 2,3,3-trimethylindolenine 1 and 6-bromohexanoic acid 2 to produce 1-(5'-carboxypentyl)-2,3,3-trimethylindolinium bromide 3; mixing compound 3 with N-[5-anilino-3-chloro-2,4-(propane-1',3'-diyl)-2,4-pentadien-1-ylidene]anilinium chloride 4 and sodium acetate in ethanol; refluxing the solution; concentrating the solution to dryness; triturated the residue with HCl; drying the residue under vacuum to yield 5; adding DCC to a solution of 5 and N-hydroxysuccimide in methylene chloride; stirring the mixture; removing the precipitates by filtration; removing methylene chloride to obtain monosuccinimide ester 6; conjugating monosuccinimide ester 6 with N-α-tBoc-lysine; treating the conjugated monosuccinimide ester 6 with TFA to yield 10; coupling of 10 with DOTA-Sulfo-NHS, in acetonitrile-water to yield the 12; adding $^{111}$InCl$_3$ 12 in ammonium acetate buffer; incubating the mixture; and purifying the mixture to obtain PC-003.

Example 3

Preparation of PC-004

Scheme 3

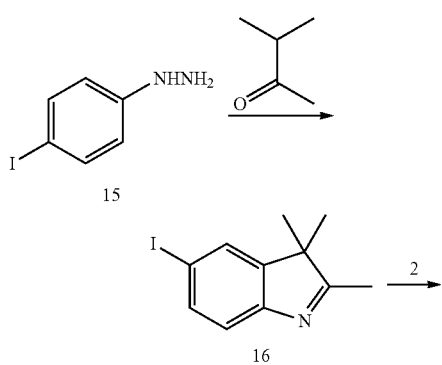

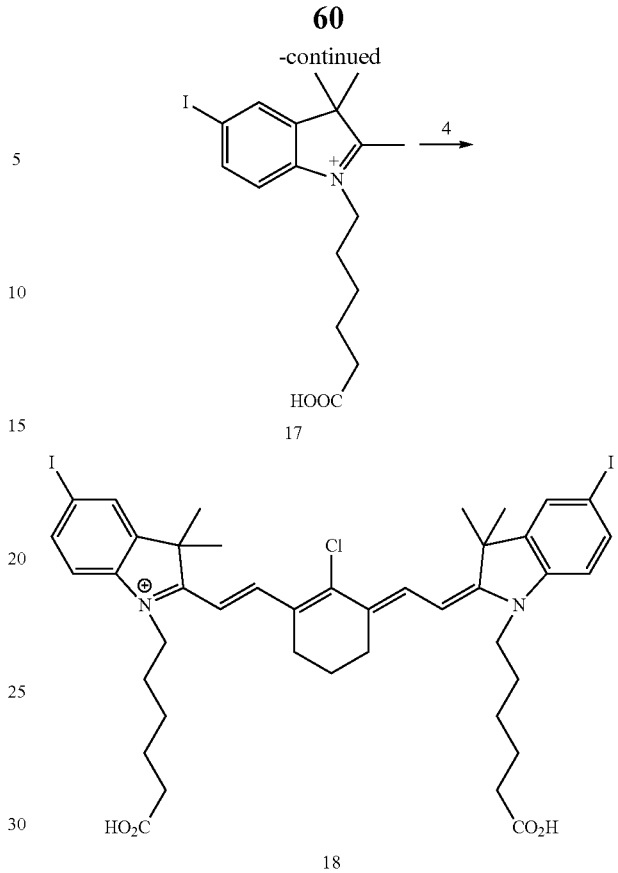

Scheme 3 depicts a reaction pathway for the synthesis and labeling radioactive iodine labeled imaging probe PC-004.

PC-003 14: The radiolabeling was accomplished by addition of 0.5-1 mCi of $^{111}$InCl$_3$ to 50-100 mg of 12 in 0.1N ammonium acetate (pH 5.5) buffer and the mixture was incubated at 40° C. for 20 minutes. The mixture was injected as is for RP-HPLC purification. The column elute was monitored by UV absorbance at 254 nm and with a gamma detector. The mobile phase was changed from 40% Solvent A (0.1% TFA in water) and 60% Solvent B (0.1% TFA in 80% aqueous acetonitrile) to 100% Solvent B at 30 min at a flow rate 3 mL/min. The PC-003-$^{111}$In was obtained at a retention time of 14.3 min with a radiochemical yield higher than 90%.

Example 4

Preparation of PC-005

Scheme 4

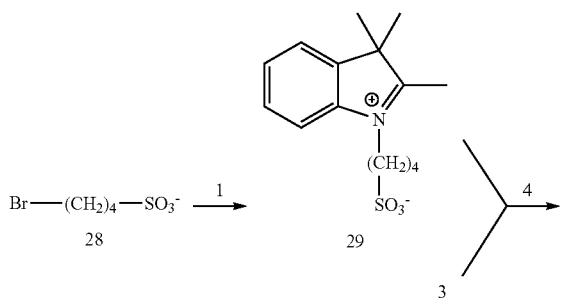

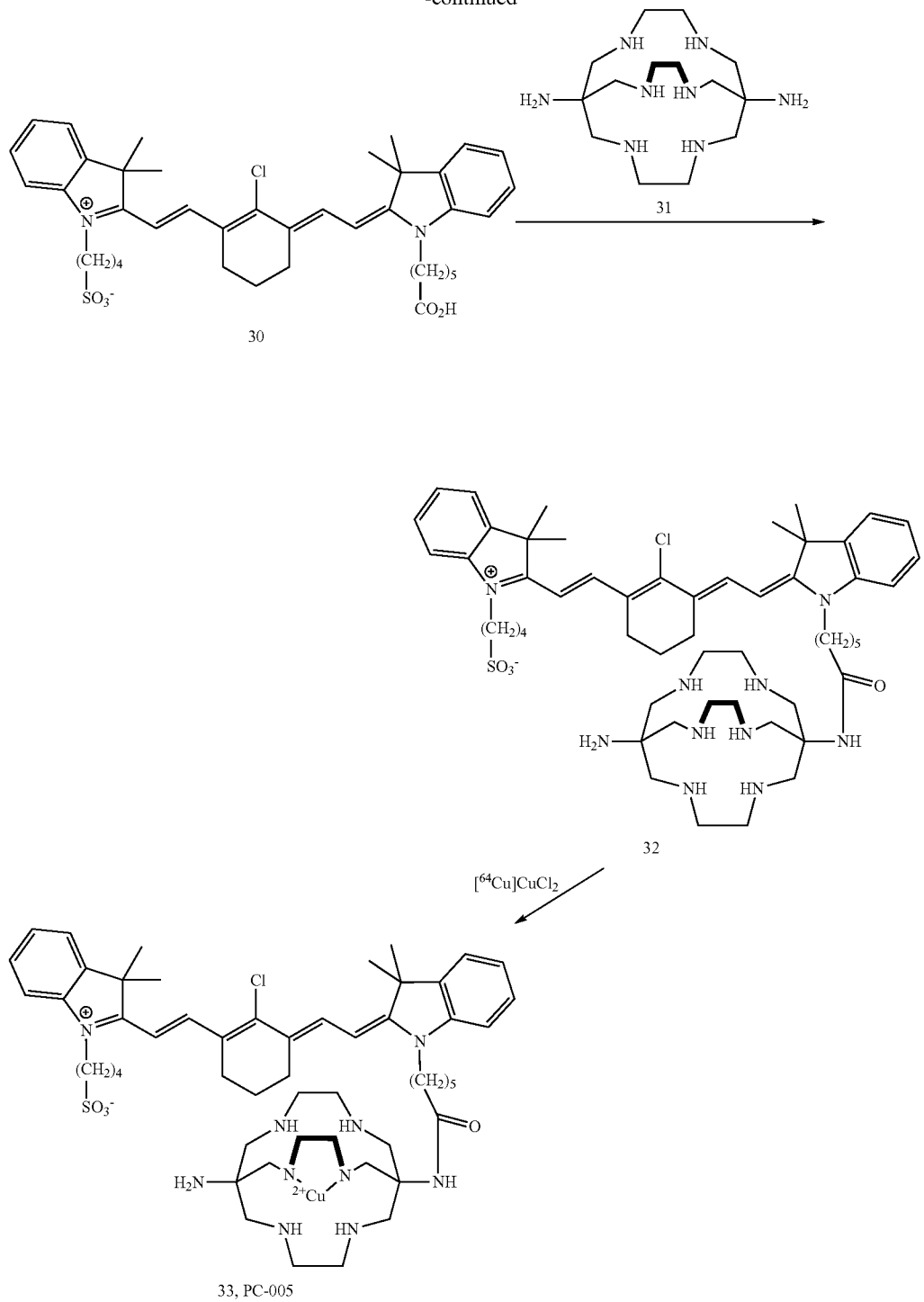

Scheme 4 depicts a reaction pathway for the synthesis and labeling $^{64}$Cu labeled PET probe PC-005.

Synthesis of diiodo-18: 5-Iodo-2,3,3-trimethylindolenine 16: A solution of 4-iodophenylhydrazine 15 (1.37 g, 5.89 mmol), isopropylmethylketone (1.40 mL, 13.0 mmol), EtOH (20 mL) and concentrated H$_2$SO$_4$ (0.3 mL) was heated under reflux for 12 h. After being cooled to room temperature, the mixture was filtered and filtrate was added to distilled water (50 mL). The product was extracted with CH$_2$Cl$_2$ (2×50 mL). The combined organic layer was washed 10% NaHCO$_3$ (2×50 mL) and (3×20 mL) distilled water, dried over sodium sulfate, filtered, and evaporated under reduced pressure to yield 16 (1.63 g, 97.08%) as a brownish liquid. mass spectrum (MALDI-TOF), m/z 286 (M+H).

A solution of 5-iodo-2,3,3-trimethylindolenine 16 and 6-bromohexanoic acid 2 was heated at 110° C. for 8 hrs to produce 1-(5'-carboxypentyl)-5-iodo-2,3,3-trimethylindolinium bromide 17. The compound 17 (100 mg, 0.21 mmol) was mixed with N-[5-anilino-3-chloro-2,4-(propane-1',3'-diyl)-2,4-pentadien-1-ylidene]anilinium chloride 4 (37.4 mg, 0.105 mmol) and sodium acetate (40 mg, 0.49 mmol) in 20 mL of ethanol and the solution was refluxed for 12 min. The solution was then concentrated to dryness and the residue was trituated twice with 5 ml of 2N HCl. The residue was dried under vacuum to yield diiodo 18 as dark solid. mass spectrum (MALDI-TOF), m/z 937.2 (M+H).

Example 5

Scheme 5

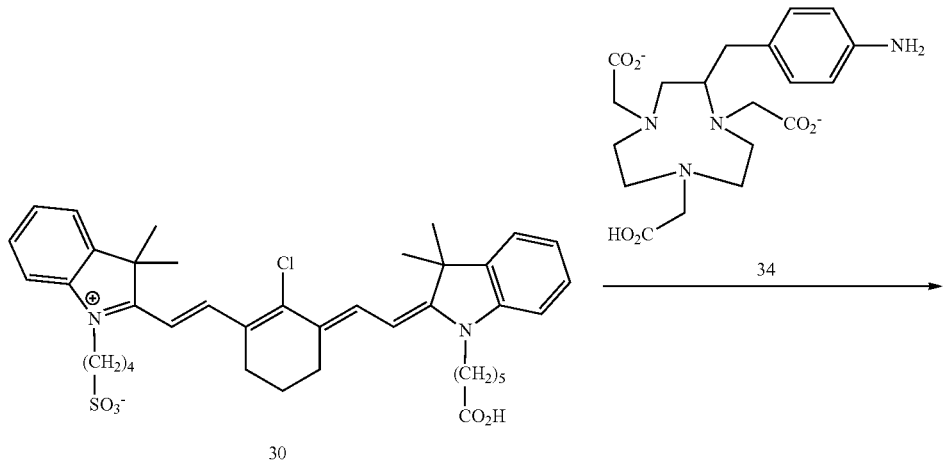

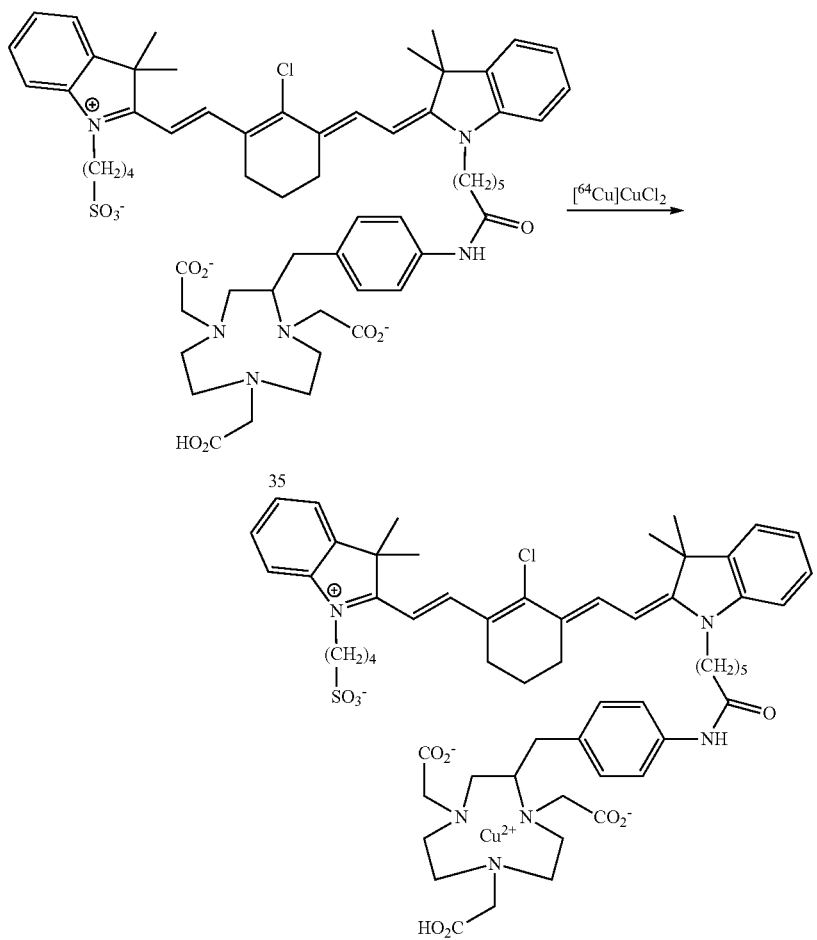

Scheme 5 depicts a reaction pathway for the synthesis and labeling $^{64}$Cu labeled PET probe PC-006.
Example 6
Scheme 6 depicts a reaction pathway for the synthesis and labeling $^{64}$Cu labeled PET probe PC-007.
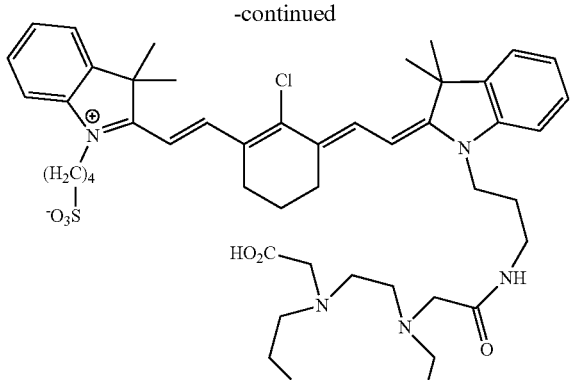
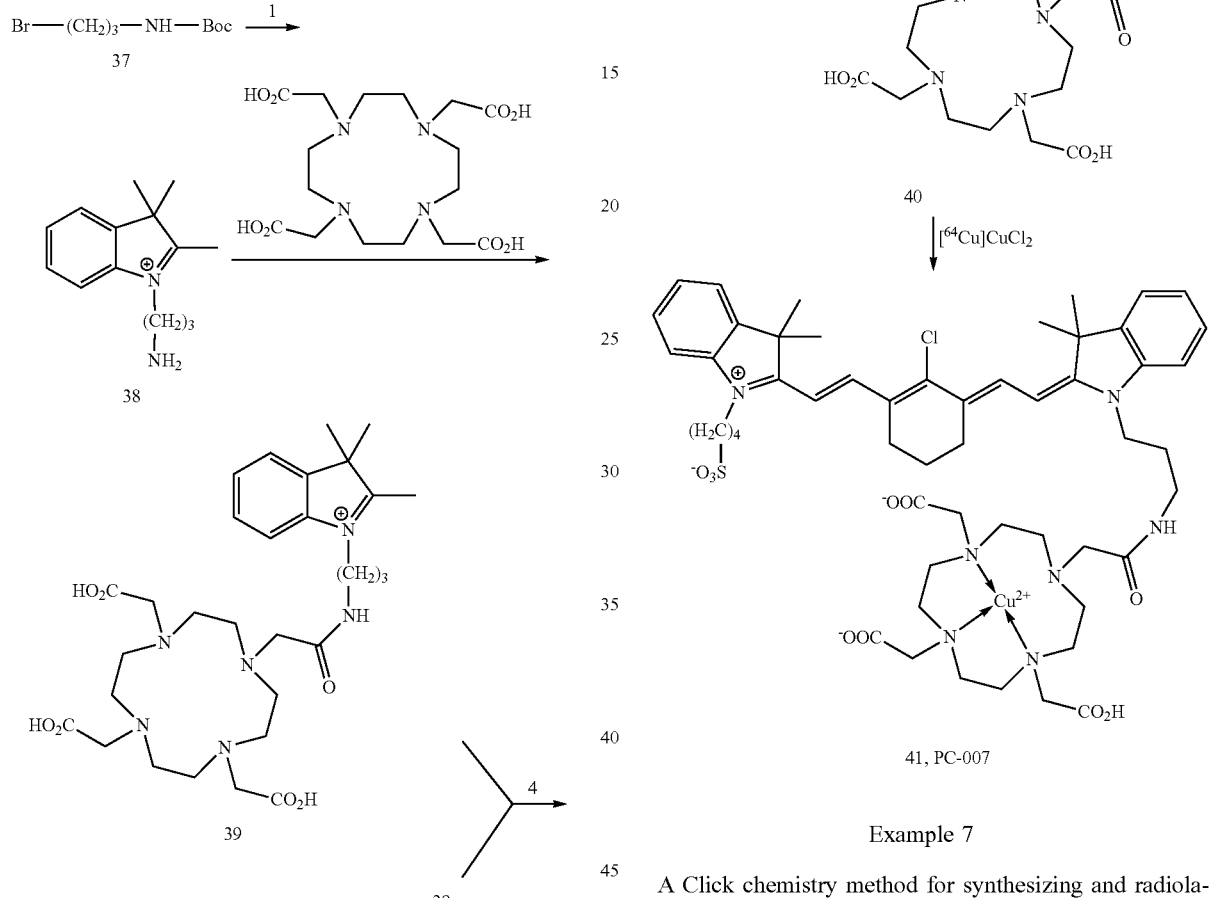
Example 7
A Click chemistry method for synthesizing and radiolabeling of Dual Nuclear/NIR Agents and analogs is depicted in Scheme 7.
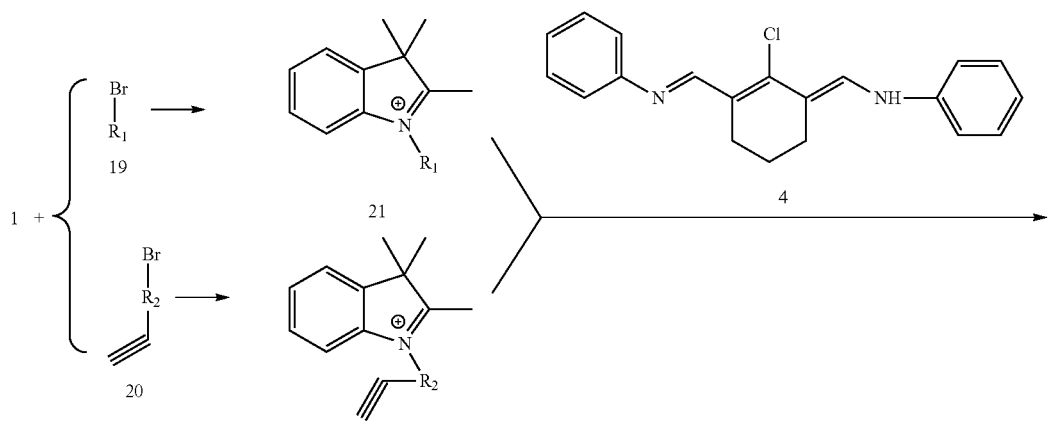

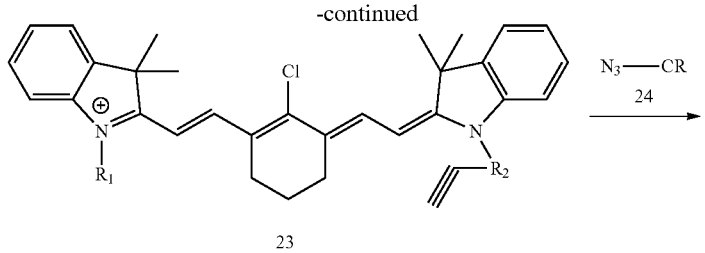

23

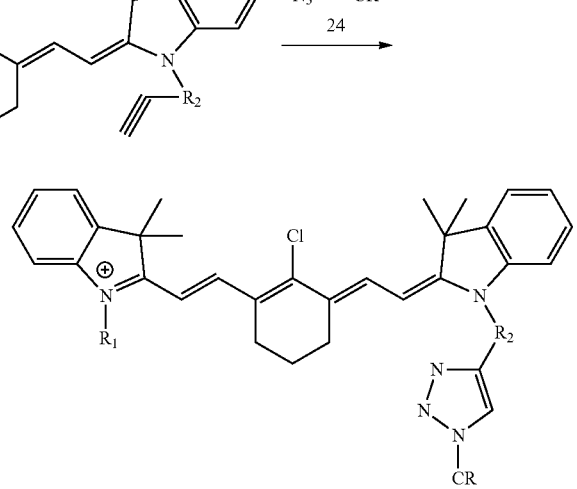

25

R₁ = alkyl, aryl, alkylsulfonato, alkylcarboxylic, alkylamino, PEGyl, PEGylcarboxylic, PEGylamino; R₂ = -ω-acyl-NH——, -alkyl-, PEGyl;
CR = a complex of a metal chelating agent and a radioactive or nonradioactive metal,
a radioiodine or iodine labeled Bolten-Hunter reagent, a radioiodine or iodine labeled tyrosine moiety.

Example 8

A Staudinger ligation method for synthesizing and radiolabeling of Dual Nuclear/NIR Agents and analogs is depicted in Scheme 8.

Scheme 8

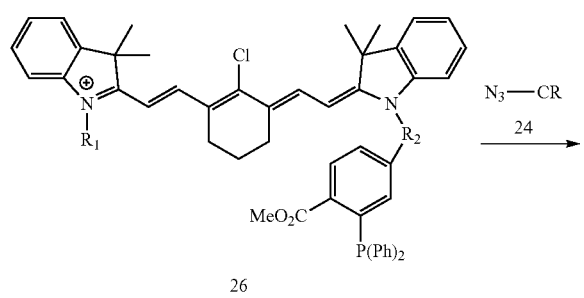

26

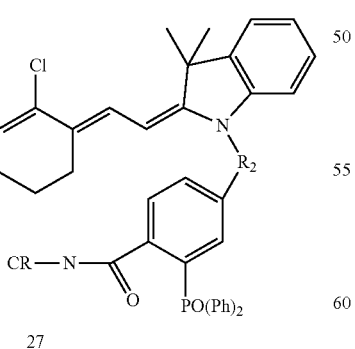

27

R₁ = alkyl, aryl, alkylsulfonato, alkylcarboxylic, alkylamino, PEGyl, PEGylcarboxylic, PEGylamino; R₂ = -ω-acyl-NH——, -alkyl-, PEGyl;
CR = a complex of a metal chelating agent and a radioactive or nonradioactive metal, a radioiodine or iodine labeled Bolten-Hunter reagent, a radioiodine or iodine labeled tyrosine moiety.

Example 9

Evaluation of Radioactive Dual Nuclear/NIR Agents as Nuclear Imaging Agents

Figure 3:
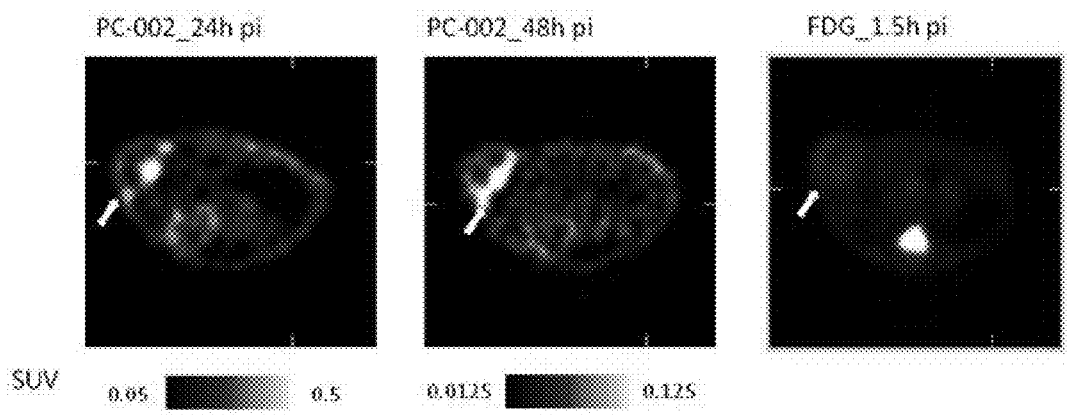
FIG. 3 depicts the transverse PET images of PC-002 at 24 and 48 h post ip injection and $^{18}$F-FDG at 1.5 h post iv injection of the same mouse (20 g) harbored with MCF-7 tumor xenografts in accordance with various embodiments of the present invention. The tumor is indicated with the white arrow. The distribution of the PC-002 in tumor is heterogeneous because the tracer targets only viable cancer tissues.
Figure 4:
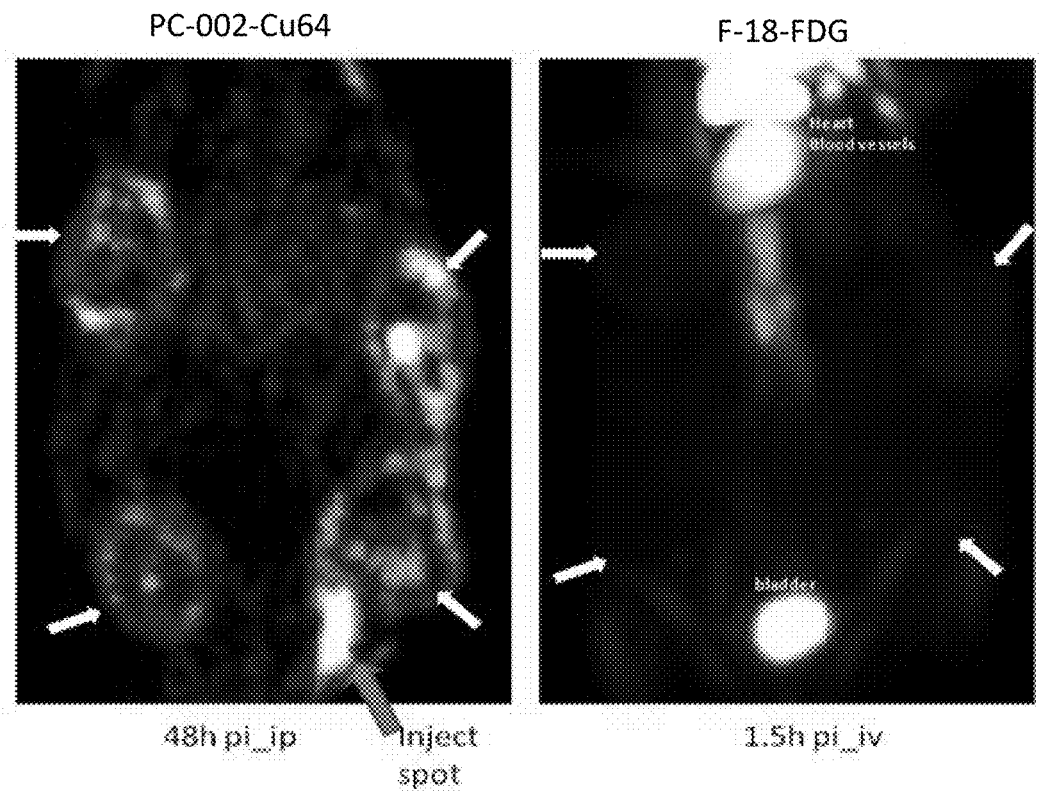
FIG. 4 depicts the comparison of maximal projection images (MPIs) of PC-002 at 48 h post ip injection and $^{18}$F-FDG at 1.5 h post iv injection of the same mouse (20 g) harbored with MCF-7 tumor xenografts in accordance with various embodiments of the present invention. The tumor is indicated with the white arrow. The distribution of the PC-002 in tumor is heterogeneous because the tracer targets only viable cancer tissues. Breast tumors can be clearly visualized by PC-002 but only barely seen by FDG, confirming that the Dual Nuclear/NIR Agents, PC-002 is more effective than the FDA approved $^{18}$F-FDG for imaging of the MCF-7 tumors.
Figure 5:
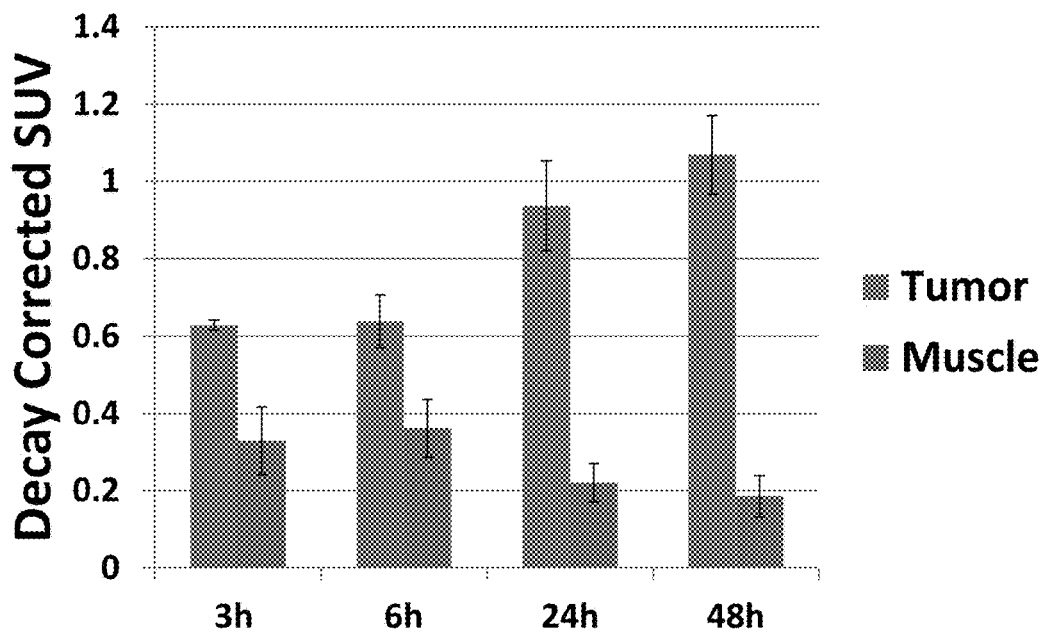
FIG. 5 depicts the SUV measurements of tumor and hind leg muscle at different post injection times in mice with MCF-7 tumor xenografts in accordance with various embodiments of the present invention.
Figure 6:
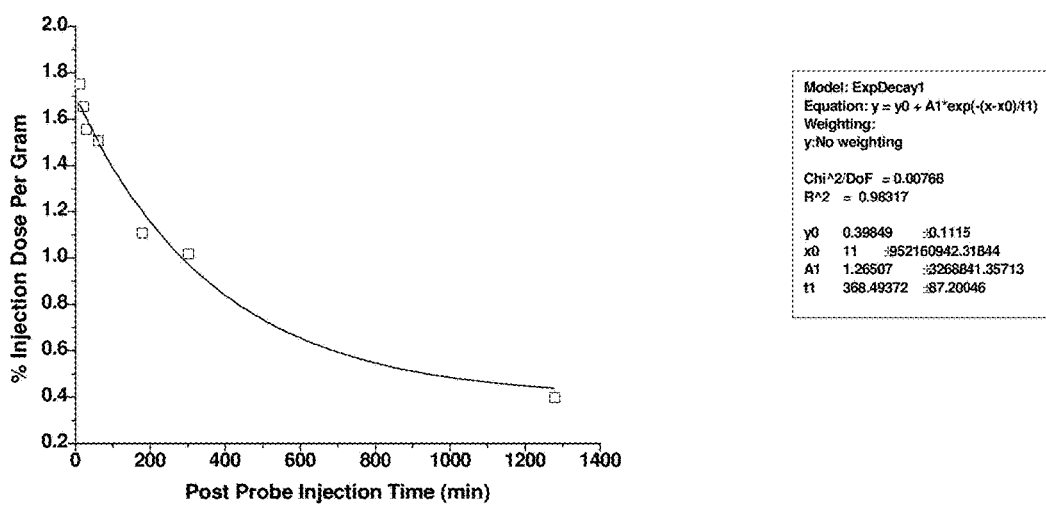
FIG. 6 depicts the blood clearance curve of PC-002 in nude mice in accordance with various embodiments of the present invention. The $T_{1/2}$ is 256.9±13.2 min. (N=3).

PC-001, PC-002, and PC-003 were evaluated as nuclear imaging probe using mice with MCF-7 xenograft tumors. All of the three compounds are suitable candidates for molecular imaging of cancer with microPET or microSPECT modalities. PC-002/PET images were compared with FDG/PET with same mice. PC-002 demonstrated higher tumor contrast and selectivity than FDG (FIGS. 3 and 4). The SUV of MCF-7 tumor was 6 times of the measurement in hind leg muscles (FIG. 5).

Dual Nuclear/NIR Agents showed slow blood clearance. The half-life ($T_{1/2}$) of PC-001, PC-002, and PC-003 is 3, 4.3, and 3 hours, respectively. The long blood circulation times results in good images taken at later hours; for example, 24 to 72 hrs post injection.

Example 10

In Vivo and Ex Vivo Evaluation of PC-002 by Optical Imaging Modalities

Figure 2:
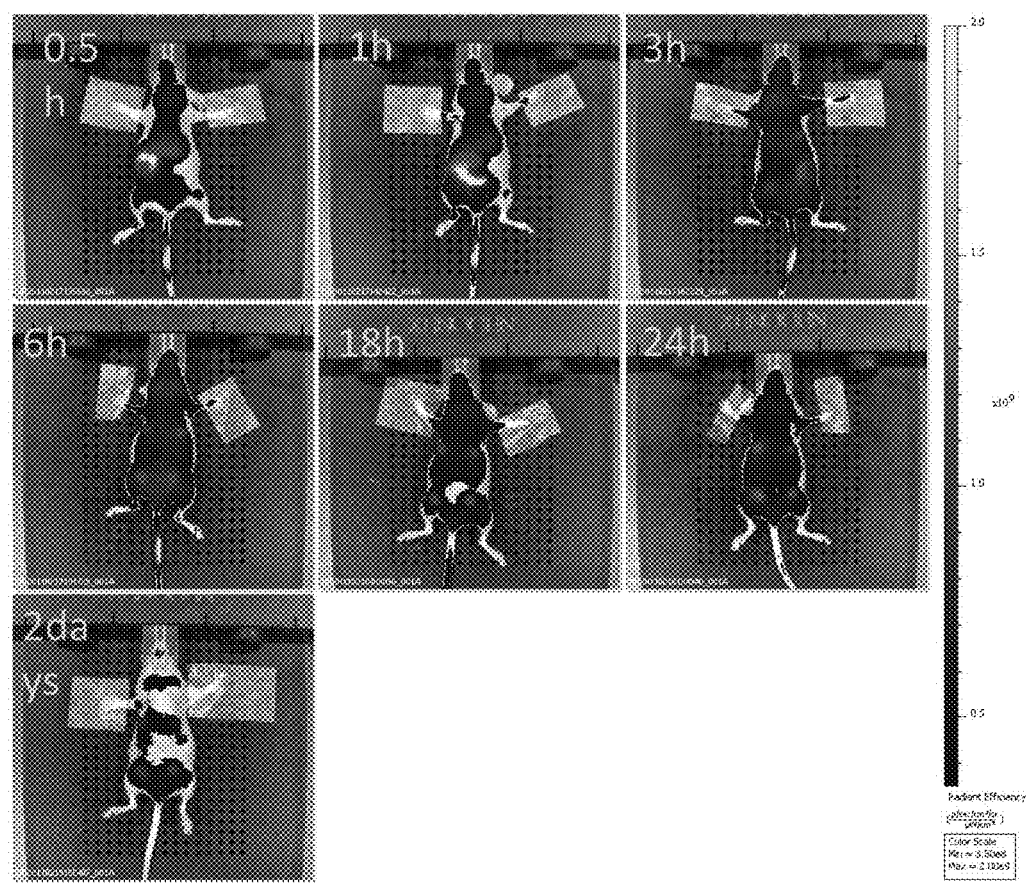
FIG. 2 depicts the NIR fluorescence image of PC-002 with a nude mouse (20 g) with MCF-7 tumor xenografts in accordance with various embodiments of the present invention. PC-002 (10 nmol) in saline (200 ul) was injected via tail vein. The live fluorescence images were performed at time points (as indicated) post injection using an IVIS Spectrum device (Ex/Em=745/800 nm).

The optical imaging property of "cold" counterpart of PC-002, comprising stable copper isotope, was evaluated with mice models with MCF-7, C4-2, and ARCaP$_M$ tumors. In mice with MCF-7 xenografts, tumor uptake of PC-002 was discernable at 3 hrs post injection and contrast of tumor and normal tissues reached most profound at 24 hrs post injection (FIG. 2).

Figure 7:
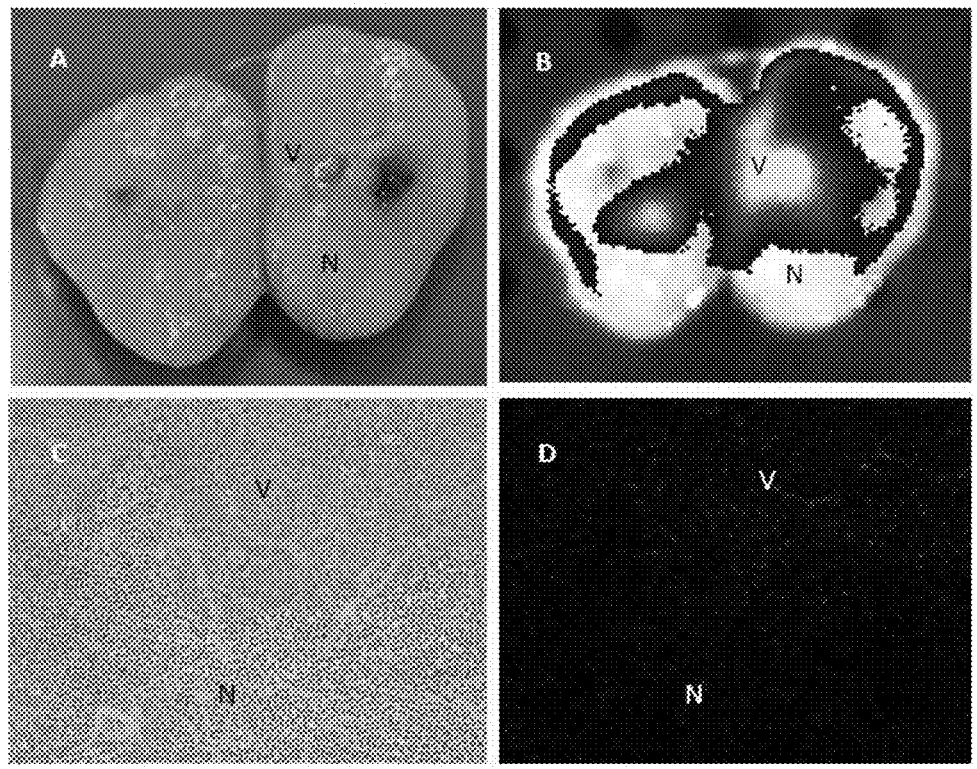
FIG. 7 depicts the correlation of PC-002 uptake and ex vivo images in accordance with various embodiments of the present invention. A MCF-7 xenograft tumor was dissected and cut into two halves. A, the photograph shows viable (V) and necrotic (N) cancer tissues; B, NIR fluorescence picture with the IVIS Spectrum shows the distribution of PC-002 in tumor; C, microscopic image of the H/E stained tumor slice; D, NIR fluorescence microscopic image of the same tumor slice. These results suggest that NIR and PC-002 signals are associated with viable and not necrotic tissues.
Figure 8:
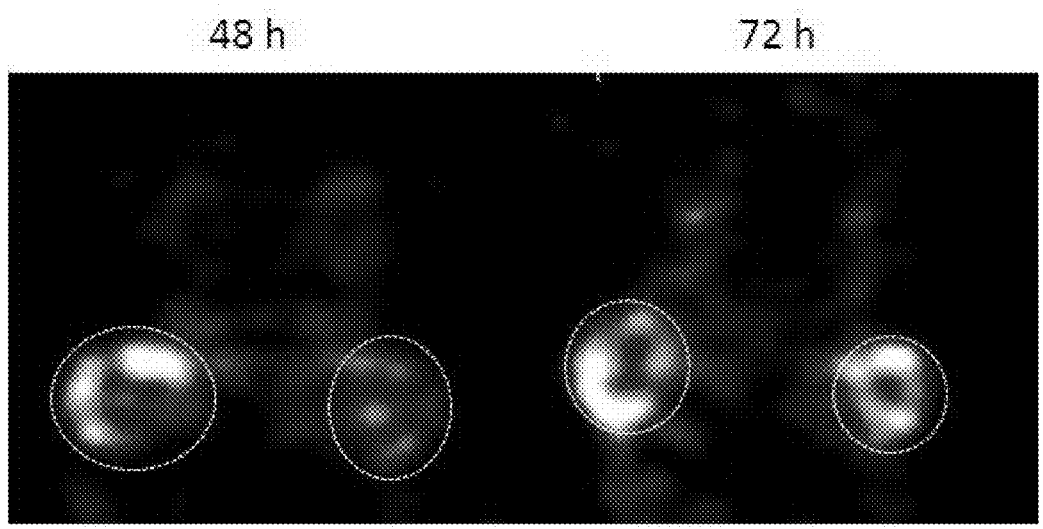
FIG. 8 depicts the transverse PET images of PC-003 at 48 and 72 h post ip injection and with the same mouse (20 g) with MCF-7 tumor xenografts in accordance with various embodiments of the present invention. The tumor is indicated with the circles. The distribution of the PC-003 in tumor is heterogeneous because the tracer targets only viable cancer tissues.

At 24 hrs post PC-002 injection, a MCF-7 xenograft tumor was dissected and cut into two halves. The viable sections of the tumor in white, right photograph matched with PC-002 fluorescence distribution performed using a Caliper Spectrum device (FIG. 7). The cancer cells in the microscopic image of the H/E stained tumor slice were also overlapped with PC-002 NIR fluorescence of the same tumor slice.

Figure 9:
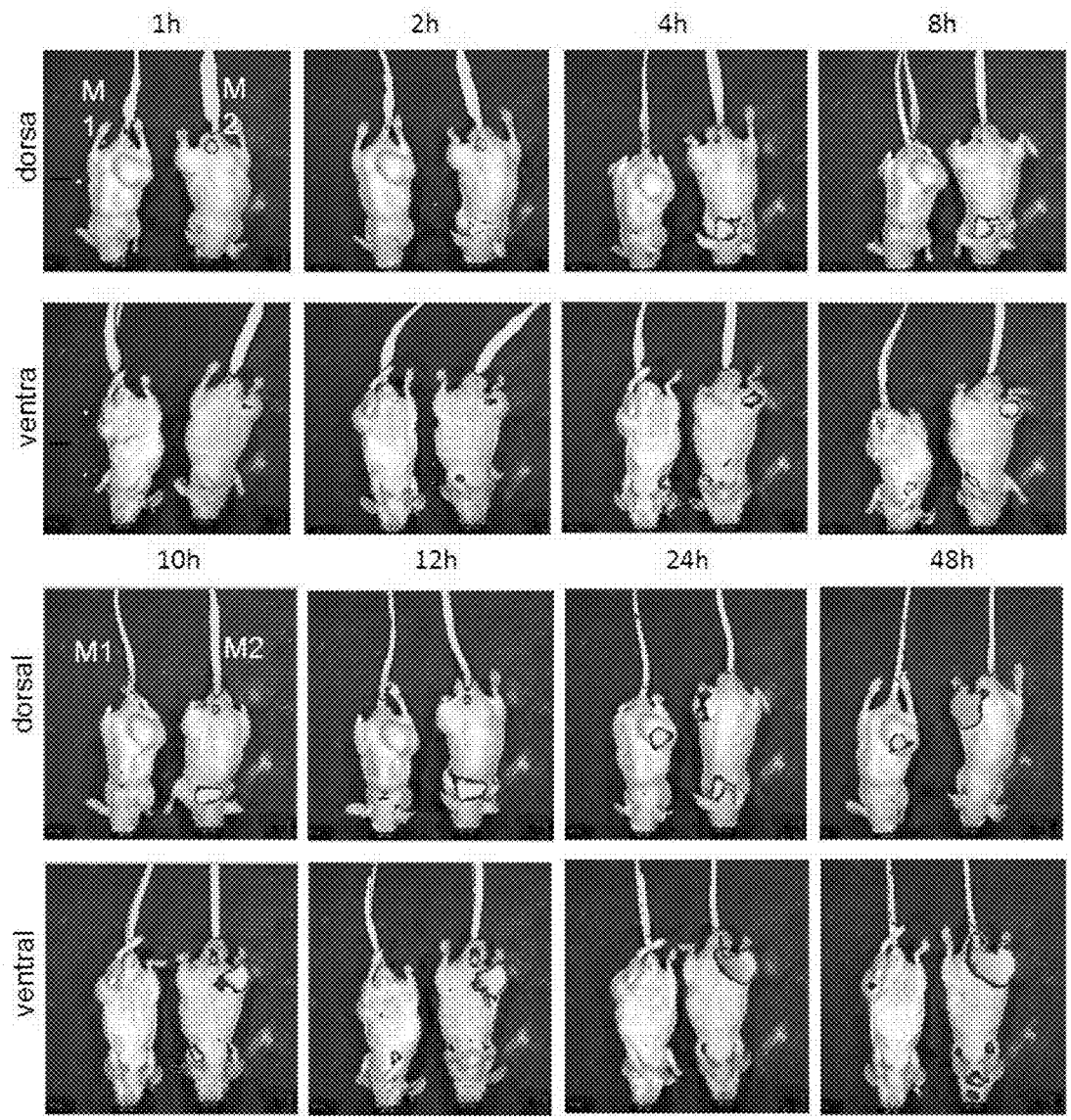
FIG. 9 depicts the NIR fluorescence images of PC-002 with two nude mice, one (M1) with a subcutaneous human prostate cancer C4-2 tumor and the other (M2) with an intratibial human prostate cancer ARCaP$_M$ tumor in accordance with various embodiments of the present invention. PC-002 (2 nmol) in saline (200 ul) was injected via tail vein. The live fluorescence images of dorsal and ventral positions were performed at time points (as indicated) post injection using a Caliper Spectrum device (Ex/Em=745/840 nm). Note intense florescence was found associated with mouse tails due to dye leakage and poor clearance of the dye from the mouse tail regions. The fluorescence signal was found accumulating in subcutaneous tumor beginning at 24 hr while the signal was found at 2 hr in the intratibial tumor in the mouse skeleton. The timing of tumor visualization is a function of blood flow through a particular tumor; in this study, blood flow at the intratibial region is higher than that of the subcutaneous region, due to the fibrotic nature of this human prostate tumor implanted in mouse subcutaneous space.
Figure 10:
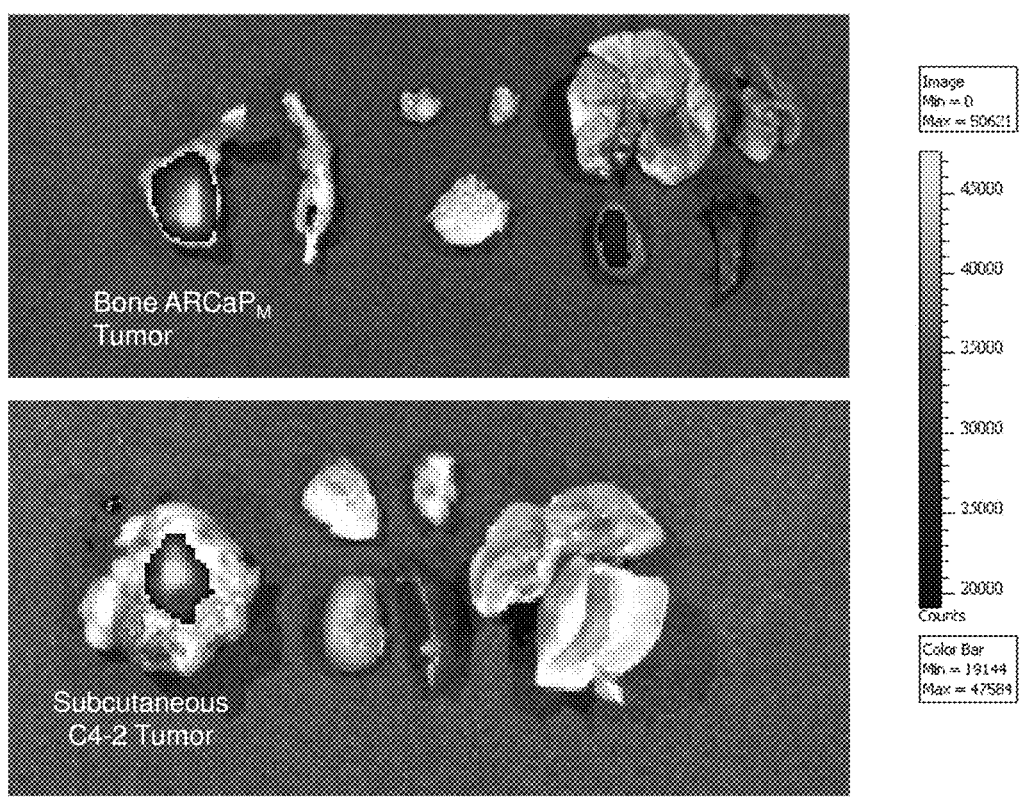
FIG. 10 depicts the tumor and soft tissues harvested after the in vivo imaging and subjected to ex vivo fluorescent imaging to confirm the uptake and retention of the PC-002 by the harvested tumor xenografts in live tissues obtained from mouse tibial bones and at a subcutaneous tumor in accordance with various embodiments of the present invention.

The PC-002 (2 nmole) was intravenously injected into mouse with either subcutaneous C4-2 or tibial ARCaP$_M$ tumors and the mice were subjected to fluorescent imaging using the Xenogen Imaging System at the interval of 1 h, 2 h, 4 h, 8 h, 10 h, 12 h, 24 h and 48 h after the dye injection. The fluorescence signal was found accumulating in subcutaneous C4-2 tumor beginning at 24 hr while the signal was found at 2 hr in the in intratibial ARCaPM tumor in mouse skeleton (FIG. 9). The tumor and soft tissues were harvested after the in vivo imaging at 24 hrs post injection and subject to ex vivo fluorescent imaging to confirm the uptake and retention of PC-002 in tumor only (FIG. 10).

Figure 11:
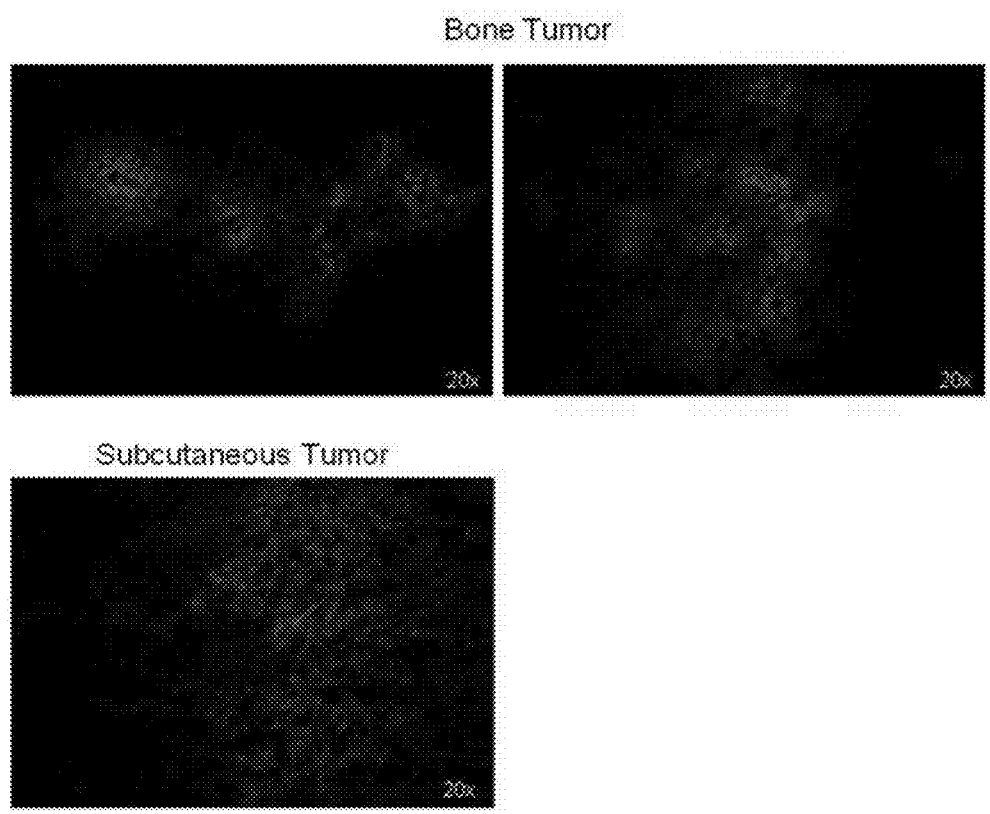
FIG. 11 depicts the harvested bone ARCaP$_M$ and subcutaneous C4-2 human prostate tumors embedded with OCT at −25° C. and subjected to frozen sectioning using Cryostat in accordance with various embodiments of the present invention. The frozen sections were fixed and aqueously mounted and imaged using fluorescent microscopy (200× magnification). Note the Dual Nuclear/NIR Agent was actively uptaken into tumor cells.
Figure 19:
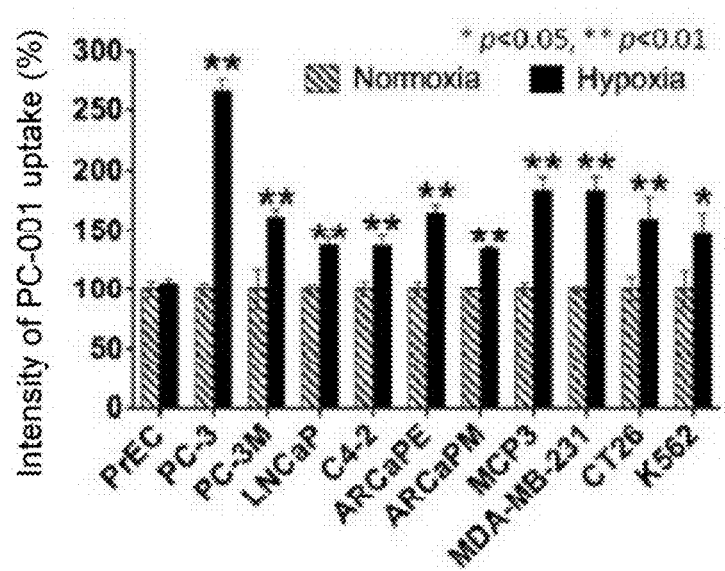
FIG. 19 illustrates increased carbocyanine dye uptake under hypoxic conditions. Human cancer cells were exposed to either normoxia or hypoxia conditions (under 1% $O_2$), and cells were stained with 20 µM PC-001 for 4 hours in triplicate. Note intracellular dye accumulations, as detected by FACS assay, were higher in hypoxia than nomoxia condition, across a wide-spectrum of cell types. Note ulinke tumor cells, normal prostate epithelial cells, PrEC, were unresponsive to hypoxia.

The harvested bone (ARCaP$_M$) and subcutaneous (C4-2) tumors were embedded with OCT at −25° C. and subjected to frozen sectioning using Cryostat. The frozen sections were fixed and aqueously mounted and fluorescent microscopy images (200× magnification) showed PC-002 selectively uptaken in cancer cells (FIG. 11).

Example 11

Development of a Novel Predictor for the Development and Lethal Progression of CRPC Based on OATPs Expression, NIR Dye and Testosterone Uptake, and their Responsiveness to Hypoxia The increased popularity of adopting a surveillance protocol in PCa patients could result in the undertreatment of certain patient populations who harbor CRPC with the potential for lethal metastatic progression. This possibility can be minimized if Pca biopsies or PCa cells in circulating blood can be monitored by imaging with results validated by harvested tissue and cell specimens, for the expression of lethal progression biomarkers. Based on the level of OATPs expression, NIR dye and androgen uptake, and responsiveness to hypoxia, NIR dye-based imaging can be exploited as a new predictor of PCa transition to castration resistance. This concept is based on the clinical observation that CRPC is capable of uptake and metabolizing androgen precursors into biologically active androgens and that CRPC remains responsive to endogenously produced androgens such as adrenal androgens, DHEA and DHEA sulfate, and other peripheral organ-derived androgen precursors. Published studies support the roles of OATPs in mediating androgen uptake by PCa cells. Overexpression and mutation of selective OATPs have also been shown to be associated with high-grade, potentially progressing, with shorter time to progression PCa in men.

Determination of the effects of genetic abrogation of OATP-1B3, -2B1 and/or -5A1 on the growth and metastasis of LNCaPRANKL tumors in mice. Correlation of the growth and behaviors of tumors, such as NIR-dye and testosterone uptake in vitro and in tumors and tumor metastasis are established. Two human prostate cancer models with evidence of developing CRPC and/or bone metastatic disease are used. These are human PCa isogenic cell lines, LNCaPNeo (non-tumorigenic) and LNCaPRANKL (tumorigenic and bone metastatic), and an androgen-responsive (Ar) human PCa xenograft LTL311 model developed by Dr. YZ Wang at Vancouver (LTL311Ar is tumorigenic, and can be promoted to undergo castration-resistant [CR] progression in surgically castrated mice, or become LTL311CR). The advantages of the LNCaP model are that NIR dye, testosterone and adrenal androgen uptake and retention in PCa cells can be determined and compared between cultured cells and live mice, and that the effects of hypoxia on dye and androgen uptake can be experimentally assessed. Since metastasis in the LNCaPRANKL tumor model is robust (100% bone and soft tissue metastases), this provides an opportunity to assess the roles of OATPs on PCa metastases by a genetic KD of OATPs, either individually or together. The advantages of the LTL311 model are that it consistently expresses both AR and PSA throughout the experimental manipulation, and the growth of LTL311 in mice can be promoted to undergo CRPC in castrated hosts. This model allows a comparative study of NIR dye and androgen uptake under various conditions before and after PCa tumors undergo CRPC transition. Two complementary studies are performed: 1). LNCaPRANKL cells, genetically tagged with luciferase, are engineered with stable expression of tetracycline-inducible siRNA-OATP-1B3, -2B1 or -5A1 using pLKO-Tet-on construct developed by Wiederschain; control cells receive the same expression vector except with a scramble siRNA construct. These cells are established and characterized in vitro. 80 adult male nude mice per group are inoculated intracardiacally (to generate experimental bone and soft tissue metastases) with 1×10$^6$ control vector or tet-on stably expressed siRNA-OATP-1B3, -2B1 or -5A1 LNCaPRANKL-Luc cells (20 mice/group). At 8 weeks when tumors begin to form, mice are randomized (10 mice/group) for feeding either tap water or tetracycline-containing water for an additional 4 weeks. PCa are detected by bioluminescence imaging. Mice are injected with PC-001, and NIR-fluorescence imaging of the tumors are co-registered with bioluminescence imaging. The extent of PCa metastases to bone and soft tissues are monitored weekly between 8-12 weeks. At 12 weeks, tumor tissues are harvested from mice and the profiles of 3H-labeled-testosterone, -DHEA and -DHEA sulfate uptake and retention in tumor tissues are determined by our previously published methods34, 35 and correlated with PC-001 uptake using established methods). LTL311 tumor xenografts (2 tumors/mouse) are established at subcutaneous sites in 10 hormone-intact adult male nude mice. Mice are randomized into two groups (5 mice or 10 tumors/group), and are subjected to either sham operation or surgical castration at 10 wks. The ability of tumors to uptake and retain PC-001 are evaluated in these mice every 3 weeks for a period of 12 weeks. At 12 weeks, tumor tissues are harvested from mice and the profiles of 3H-labeled-testosterone, -DHEA and -DHEA sulfate uptake and retention in tumor tissues are determined and correlated with PC-001 uptake using established methods.

Tumor tissues harvested from both of these studies are also subjected to histopathological, immunohistochemical and molecular evaluations, with emphasis on determining the levels of OATPs m-RNA and protein expression, and PC-001 cellular and subcellular localization. These assays are repeated in tissues maintained under hypoxic conditions using our established protocol. Results from these analyses are correlated with serum PSA, a marker for the development of CRPC, and other cell growth (Ki67), angiogenesis (CD31), apoptosis (annexin V, TUNEL), differentiation (neuendocrine and stem cell markers), and behavior (EMT)-associated biomarkers in tissues. Statistical analyses are conducted in consultation with the Cedars Biostatistical Core.

The uptake and retention of three heptamethine cyanine NIR dyes, PC-001, IR783 and IR-780, by a broad spectrum of human and mouse cancer cell lines in vitro and tumor xenografts in vivo, including Pca were reported. This work was confirmed in freshly obtained human renal and bladder cancer surgical specimens. Control specimens or sham-operated mice yield no NIR dye signal (FIG. 12). FIGS. 12A-B illustrate using heptamethine carbocyanines to detect freshly harvested kidney tumor implants as xenografts. Representative results from 4 surgical human kidney specimens are shown in FIG. 12A and FIG. 12B. A. Dices of two human kidney tumor tissue specimens were implanted subcutaneously and were subjected to NIR imaging following PC-001 administration. Note positive signals (upper right panel) were detected in two subcutaneous implants (thick arrows) and the sites of sham implants (thin arrows) had no signal. B. Left panel shows positive NIR imaging after PC-001 administration from additional human kidney tumor tissue dices in subrenal capsular space. Right panel (H&E) shows the confirmation of NIR staining with tumor but not normal cells or necrotic tumor cells within the implanted tumor tissues to confirm the cancerous nature of the specimen. These results suggest that freshly arvested clinical kidney cancer specimens are well perfused by the circulating organic dyes in mouse blood.

PC-001 uptake by both tumor models correlates with the expression of OATP-1B3, -2B1 and/or -5A1 and the uptake of androgens into tumor tissues. PC-001 uptake also correlates with the development of CRPC in both of these tumor models and the potential for bone and soft tissue metastases in the LNCaP model. Heterogeneity of PC-001 uptake could be contributed by the copresence of androgen-responsive and castration-resistant PCa cell populations. These differences can also contribute to the status of hypoxia and the live, dead or adaptive states of the tumor cells since dead cells were found to be incapable of NIR dye uptake. Because hypoxia can activate dye uptake and retention in cancer cells, and hypoxia could potentially enlarge the differences between androgen-responsive versus androgen-resistant PCa cells, we have developed a highly sensitive promoter-reporter assay protocol by creating genetically engineered PCa cells with stable (HRE)5-Luc expression. These cells, when subjected to hypoxia, expressed 25 times more luciferase activity than those maintained in normoxic conditions (FIG. 13). Therefore, these cells can be used to address the questions discussed above generating wider differences, based on reporter read-out, between cells with differential response to hypoxia and among cells undergoing development of castration resistance with the potential of exhibiting bone and soft tissue metastases. Assessment of dye uptake, OATPs expressions, status of hypoxia and the ability of PCa cells to develop CRPC and bone and soft tissue metastases in clinical specimens can be accomplished by the use of tissue biopsies or CTCs; we have successfully demonstrated the detection of a series of cell-signaling-related genes in CTCs isolated directly from PCa patients by a previously established microfluidic-based protocol with isolated PCa cells analyzed by a multiplex quantum-dot based labeling technology developed by our laboratory (FIG. 14). FIG. 14 illustrates mQDL characterization of gene expression in CTCs of Pca patients. Periphery blood samples of PCa patients were used to isolate CTCs based on NIR staining and EpCAM marker expression. The isolated CTCs were queried for expression of important genes associated with Pca progression and bone metastasis with mQDL assay, which was established in our laboratory. Shown is a representative detection of 6 protein levels in a single CTC. This technique can be extended in the future to analyze OATPs, NIR dye uptake, HIF1α. and biomarkers detected in tissues predict lethal bone and soft tissue metastases in CRPC patients. Assuming OATPs and HIF1α are the new predictors for CRPC, it is conceivable that the levels of these gene products, or the polymorphisms of these genes can be detected in tissues and cells at a single cell level. Quantification of the levels of these genes in biopsy tissues and in CTCs by the Vectra multispectral imaging and quantification system at tumor and tumor-associated stroma can be performed and results could allow us to predict the progression of PCa toward CRPC. Due to specific uptake of PC-001 by tumor tissues, a pilot study evaluates if this NIR dye could assist in the identification of surgical margins during robotic surgery for primary PCa. Mice are inoculated with human PCa cells at orthotopic sites using our established protocol. The presence of Pca tumors in the prostate gland are confirmed by bioluminescence imaging. 24-48 h prior to surgery, mice are injected with PCT-001 as described. At the time of the surgery, mice are injected with indocyanine green dye (ICG). Mice are robotically operated under the da Vinci SiR robotic surgical system equipped with a near-infrared 3-D vision system (provided by Dr. David Josephson, a urologic surgeon who routinely performs robotic surgery in patients). Preliminary studies have shown promise of the application of this dye for the imaging of prostate tumors, which gave stronger fluorescence signal than that of the control mouse kidney tissues (FIG. 15). Mice bearing PC-3 tumors were injected with 20 nmoles of PC-001, 24 h prior to sacrifice. Both the tumor and host kidneys were removed and subjected to NIR fluorescence imaging under the daVinci Si® robotic surgical system equipped with NIR fluorescence mode. The tissues were illuminated by a medical laser at 805 nm with emission at 835 nm. Note that PC-3 tumors yield stronger emission than that of the normal mouse kidneys. Background emission from normal kidneys can be reduced by adjusting the dose of NIR dyes and the time prior to imaging (FIG. 15). ICG has been FDA approved for renal perfusion and vessel identification during robotic-assisted laparoscopic partial nephrectomy. Tumor margins are identified by co-registering PC-001 (tumor) and ICG (normal) positively stained cells. The extent of PC-001 uptake into tumor tissue and ICG uptake into normal tissue are used as a guide for more accurately identifying tumor margin upon robotic surgery. Surgical specimens harvesting from the study are subjected to histopathologic, fluorescence microscopic and confocal microscopic imaging analyses.

Example 12

Development of a PET/SPECT Dual Modality Imaging Method with a 64Cu Based Heptamethine Cyanine Dye for Imaging PCa and a 99 mTc-MDP for Detecting Reactive Bone Activity in Mice Harbor with Experimental PCa Bone and Soft Tissue Metastases Cancer bone metastasis is commonly detected by Tc-MDP scintigraphy, but this scan can only detect reactive bone activity and does not simultaneously acquire crucial information on the status of the tumor. In the past, several attractive PET probes, such as $^{18}$F-2-fluoro-2-deoxy-D-glucose (18 F-FDG) or 111In-tagged antibodies, and more recently the development of smaller sized versions of antibodies such as diabodies and minibodies recognizing PSMA and PSCA, have been proposed to detect PCa; but because of their relative large molecular weight as antibodies, potential host immune response to foreign antibodies, and the lack of Pca specificity using 18F-FDG, application of PET/SPECT probe to detect PCa has not been successful. Due to the small molecular weight of PC-002 (<1,000 Da, please see the synthetic Scheme 2), a derivative of PC-001, and its specificity in accumulating in cancer cells upon derivation to 64Cu-PC-002, we demonstrated the ability of 64Cu-PC-002 to accumulate in tumors in mice (FIG. 16). As a small molecule, PC-002 has the advantages of being non-immunogenic, easier to purify and to scale-up, and higher stability for storage and shipping. Because of suboptimal NIR dye signal penetration through deep tissues, we chemically synthesized PC-002, a lead PET 64Cu-DOTA-NIR dye30, to facilitate future translation to the clinic. We showed that this compound has remarkable selectivity for tumor xenografts yielding a small amount of demetallated 64Cu deposit in the liver (FIG. 16). Based on this highly promising result, 64Cu-DOTA-based NIR dye for imaging PCa bone and soft tissue metastases can be used concurrently with 99 mTc-MDP to detect reactive bone activity. For example, this strategy can be used in the robust mouse models of PCa metastasis developed by our laboratory. A dual 64Cu-PC-002 and 99m Tc-MDP imaging modality can be used to detect tumor and bone activity simultaneously for the assessment of PCa tumor metastasis to bone using robust human PCa bone metastatic models. This also allows one to detect soft tissue metastasis by monitoring the accumulation of 64Cu-PC-002 in the metastatic tumors. The dual PET/SPECT imaging technology described herein can be translated to the clinic for simultaneous evaluation of PCa at metastatic sites and reactive bone activity. This new non-invasive imaging protocol could improve the follow-up of patients on surveillance protocols or active pharmacologic intervention trials.

In one example of this approach, human PCa cell lines LNCaPRANKL and ARCaPM, with robust bone and soft tissue metastatic potential is used. $1 \times 10^6$ LNCaPRANKL or ARCaPM cells, genetically tagged with luciferase, is injected through the intracardiac route into 20 adult male nude mice to produce experimental bone and soft tissue metastases. Tumor metastases are assessed 8 weeks post tumor cell inoculation by bioluminescence imaging, and mice positively identified to have tumor metastases are subjected to dual PET and SPECT imaging with 64Cu-PC-002 (200 uCi) and 99 mTc-MDP (300 uCi), respectively. These radiotracer materials are administered via tail veins 24 h (for 64Cu-PC-002) and 3 h (for 99 mTc-MDP) before scanning CT (to acquire anatomical bone structure), SPECT, and PET are continuously performed in a fixed-position of the mouse bed. Trimodal images are reconstructed and fused to show cancer and bone activities at metastatic skeletal sites. In soft tissue metastases, tumor activity is imaged by 64Cu-PC-002 through PET scans. The growth of the tumors and the reactions from the bone are obtained weekly from 8 to 12 weeks after tumor cell inoculation. The uptake of 64Cu-PC-002 by metastatic tumors, at the soft tissues and at the bone sites is monitored and validated by two quantitative methods: 1) to count the total uptake of these radionuclides by quantitative scintillation counting; and 2) to determine the localization of the radionuclides at the cellular level by the use of microautoradiography. Pilot studies are conducted to draw a relationship between tumor and bone (i.e. surrounding the tumor) weight and the total quantitative counts obtained by scintillation counting of the harvested tissues. In addition to quantifying the uptake of 64Cu-PC-002 and 99 mTc-MDP by tumor and bone cells, evaluation of reference areas at bone and soft tissues adjacent to the tumors to understand the nature of reactive bone and stroma, the field effects, and their potential uptake of these radiotracers is performed.

Bone and soft tissue metastases in all of the mice inoculated with these tumor cell lines are detected. Physical locations of the tumors and reactive bone detected by PET/SPECT are to merge with bioluminescence imaging. Since 64Cu-PC-002 and 99 mTc-MDP are accumulated respectively in tumor and bone cells, we expect to detect both of these tracers in bone metastasis but only 64Cu-PC-002 in PCa soft tissue metastasis. The amount of tracer accumulation counted quantitatively by scintillation counting should correlate directly with the size of the tumor or the area of the reactive bone. However, 99 mTc-MDP and 64Cu-PC-002 images cannot be directly correlated in bone metastasis due to physical location of the metastatic bone lesions, the viability of the tumor cells, and the extent of bone reaction to the invading tumors. Further, 64Cu-PC-002 uptake could vary dependent upon the extent of tumor necrosis (dead cancer cells do not uptake 64Cu-PC-002) and hypoxia (which increases 64Cu-PC002 uptake) and this could contribute to discordant PET and SPECT images. Despite these limitations, however, the information acquired can significantly improves artisans' ability to assess tumor growth and therapeutic responses at metastatic sites. Because of a small amount of demetallated 64Cu accumulation in mouse liver, 64Cu-PC-003 is synthesized and DOTA in 64Cu-PC-002 is replaced with TODA to increase the chemical stability of this tumor-specific 64Cu-conjugated NIR dye.

Example 13

Develop 90Y- and 177Lu-Tagged NIR Dyes and Test their Effectiveness in Eradicating Pre-Existing PCa in Mouse Skeleton and Soft Tissues Mechanisms of NIR-dye uptake and accumulation in cancer cells: Because NIR dye uptake can be completely blocked by a specific OATP inhibitor, BSP16, we explored potential expression differences among OATPs between normal (PrEc and P69) and cancerous PCa (PC-3 and PC-3M) cells. FIG. 20 summarizes the relative expression levels of three OATPs, 1B3, 2B1 and 5A1 in normal and cancerous prostate epithelial cells. OATP1B3, 2B1 and 5A1 were found to be overexpressed in PCa cell lines (PC-3 and a highly metastatic PC-3M) when compared to the normal prostate epithelial cell lines (PrEc and P69). Wide-range of mRNA differences, from 1.5- to 1240-fold, based on qRT-PCR, can be detected between PCa and normal prostate epithelial cells. In comparison to the normal prostate epithelial cell lines, all three OATPs were markedly overexpressed in PCa cells. These results were confirmed in human tumor xenograft models and in human PCa specimens. Since OATP-1B3 was reportedly overexpressed in high grade human prostate tumors, we investigated whether genetic knockdown (KD) OATP-1B3 levels can affect NIR-dye uptake.

PC-001 was shown to accumulate specifically in cancer tissues with long retention time (at least 1 week). This property is exploited for the synthesis and testing of a novel class of 90Y- and 177Lu-tagged PC-001 radiopharmaceuticals (the T1/2s for 90Y- and 177Lu are 2.67 and 6.71 days, respectively) which can be delivered directly to PCa cells and exert direct cytotoxic effects on the growth of PCa tumors by specifically killing the metastatic PCa tumors in mice. This approach avoids collateral damage to normal cells and tissues. 90Y- and 177Lu radionuclide-tagged PC-001 derivatives are expected to emit β- and γ-particles which can damage DNA at the cellular level and cause cell death. The use of these radiopharmaceuticals also helps us detect the extent of accumulation of radioactivity in tumors via SPECT imaging. This approach leads to a better understanding of the potential contrast effectiveness of radiopharmaceuticals by delivering them directly to cancer cells as opposed to external beams applying radiation from external sources.

The synthetic strategy described in Scheme 6 is applied for creating highly effective 90Y- and 177Lu-tagged PC-007 derivatives, 90Y-PC-007 and 177Lu-PC-007. First, this Scheme described the organic synthesis of precursor 40. Subsequently, 40 is conjugated with commercial [90Y]YCl3 or [177Lu]LuCl3 accordingly. All new compounds are characterized by NMR and/or mass spectroscopy. The relevant pharmacokinetic and pharmacodynamic parameters, such as stability in serum, blood clearance, and biodistribution in mouse models, of the new radiopharmaceuticals are determined according to our previous reports.

$1 \times 10^6$ LNCaPRANKL (to generate more osteolytic responses) or ARCaPM (to generate mixed osteoblastic and osteolytic responses) PCa cells, genetically tagged with luciferase, are injected by the intracardiac route into 60 adult male nude mice to produce experimental bone and soft tissue metastases according to established protocols. 30 mice are inoculated with LNCaPRANKL and 30 mice are inoculated with ARCaPM. Tumor metastases are assessed 8 weeks post tumor cell inoculation by bioluminescence imaging and mice positively identified to have tumor metastases are randomized into three groups by cell lines (10 mice/group). One group is treated with 90Y-PC-007, one group is treated with 177 Lu-PC-007, and a third group is treated with vehicle. Tumor growth is followed by luciferase bioluminescence imaging and the extent of tumor and bone responses to the cytotoxic effects of these radiopharmaceuticals by dual PET and SPECT imaging with 64Cu-PC-002 (200 uCi) and 99 mTc-MDP (300 uCi), respectively, as described above. At the end of treatment, tumor tissues are harvested from host mice and subjected to histopathologic and immunohistochemical analyses (Ki-67, TUNEL, and CD-31 for cell proliferation, apoptosis and angiogenesis, with images digitized and immunostaining intensity per cell recorded using a Vectra system).

In comparison to the generic control PC-001, both 90Y- and 177Lu tagged PC-007 are expected to induce dramatic shrinkage of PCa tumors at metastatic bone and soft tissue sites. Positive tumor responses to therapy is reflected by markedly reduced luciferase bioluminescence imaging, 64Cu-PC-002 imaging associated with tumors and 99 mTc-MDP imaging associated with bone. Mechanisms of tumor shrinkage by 90Y- and 177Lu-PC-007 could involve local DNA damage to both tumor and supporting stroma and this is confirmed by increased apoptosis and decreased proliferation and angiogenesis at the cellular level, as revealed by immunohistchemical staining. Both the LNCaP and ARCaP tumor models, with either osteolytic or mixed osteolytic/osteoblastic tumors, respond to this therapy. Potential improvement of therapeutic effects of 90Y- and 177Lu-tagged PC-007 can be achieved by synthesizing nanoparticle-based derivatives of these reagents to increase the delivery of radioactive doses to tumor cells. While this approach is effective, precautions need to be exercised to avoid the formation of large-sized particles through self-assembly of 90Y- and 177Lu-PC-007. The large sizes of these compounds could result in accumulation of these radiopharmaceuticals in the reticular endothelial system and could result in damage to normal organs such as liver and kidney.

REFERENCES

Andriole, G. L., R. L. Grubb, S. S. Buys, D. Chia, T. R. Church, M. N. Fouad, E. P. Gelmann, P. A. Kvale, D. J. Reding, J. L. Weissfeld, L. A. Yokochi, E. D. Crawford, B. O'Brien, J. D. Clapp, J. M. Rathmell, T. L. Riley, R. B. Hayes, B. S. Kramer, G. Izmirlian, A. B. Miller, P. F. Pinsky, P. C. Prorok, J. K. Gohagan, and C. D. Berg. 2009. Mortality Results from a Randomized Prostate-Cancer Screening Trial. New England Journal of Medicine 360 (13):1310-1319.

Schröder, F. H., J. Hugosson, M. J. Roobol, T. L. J. Tammela, S. Ciatto, V. Nelen, M. Kwiatkowski, M. Lujan, H. Lilja, M. Zappa, L. J. Denis, F. Recker, A. Berenguer, L. Määttänen, C. H. Bangma, G. Aus, A. Villers, X. Rebillard, T. van der Kwast, B. G. Blijenberg, S. M. Moss, H. J. de Koning, and A. Auvinen. 2009. Screening and Prostate-Cancer Mortality in a Randomized European Study. New England Journal of Medicine 360 (13):1320-1328.

Wang, Y. C. 1980. Review of excipients and pH's for parenteral products used in the United States. Journal of the Parenteral Drug Association 34 (6):452-462.

Yang, X., C. Shi, R. Tong, W. Qian, H. E. Zhau, R. Wang, G. Zhu, J. Cheng, V. W. Yang, T. Cheng, M. Henary, L. Strekowski, and L. W. K. Chung. 2010. Near IR Heptamethine Cyanine Dyeâ€" Mediated Cancer Imaging. Clinical Cancer Research 16 (10):2833-2844.

Various embodiments of the invention are described above in the Detailed Description. While these descriptions directly describe the above embodiments, it is understood that those skilled in the art can conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it are obvious to those skilled in the art that, based upon the teachings herein, changes and modifications can be made without departing from this invention and its broader aspects and, therefore, the appended claims are to encompass within their scope all such changes and modifications as are within the true spirit and scope of this invention. It are understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

It is to be understood that this invention is not limited to the particular polymers, synthetic techniques, active agents, and the like as such can vary. It is also to be understood that the terminology used herein is for describing particular embodiments only, and is not intended to be limiting.

It must be noted that, as used in this specification, the singular forms "a," "an," and "the" include plural referents unless the context clearly dictates otherwise. Thus, for example, reference to an "excipient" includes a single excipient as well as two or more of the same or different excipients, reference to a "compound" includes a single compound as well as two or more compounds, and the like.

What is claimed is:
1. A Dual Nuclear/NIR Agent having one of the following structures:
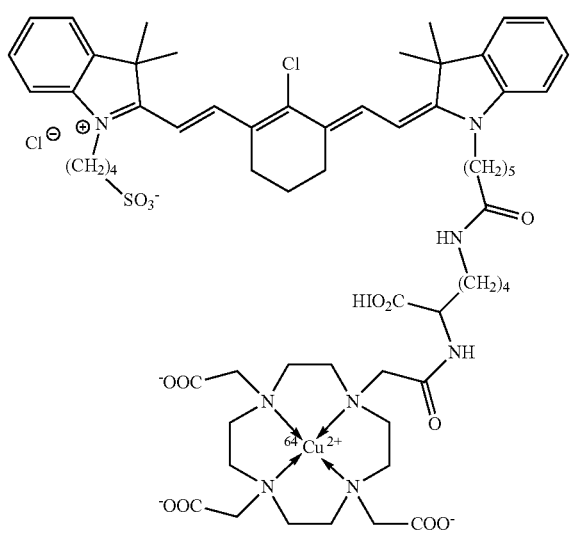
PC-1001
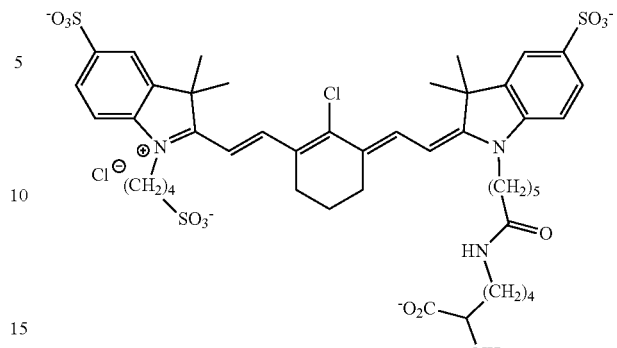
PC-1002
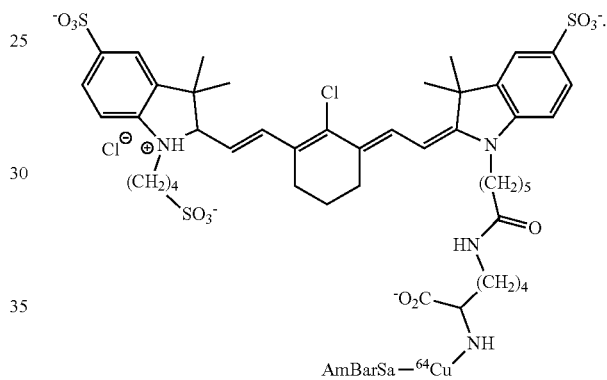
PC-1003
2. A pharmaceutical composition comprising the Dual Nuclear/NIR Agent according to claim 1, and at least one pharmaceutically acceptable carrier.
* * * * *

UNITED STATES PATENT AND TRADEMARK OFFICE
CERTIFICATE OF CORRECTION

| | |
|---|---|
| PATENT NO. | : 9,610,370 B2 |
| APPLICATION NO. | : 14/350194 |
| DATED | : April 4, 2017 |
| INVENTOR(S) | : Chung et al. |

It is certified that error appears in the above-identified patent and that said Letters Patent is hereby corrected as shown below:

In the Specification

In Column 1, after the paragraph Cross Reference to Related Applications, insert the following paragraph at Line 19:
--STATEMENT REGARDING FEDERALLY SPONSORED RESEARCH AND DEVELOPMENT
This invention was made with government support under Grant No. CA098912, awarded by the National Institutes of Health. The Government has certain rights in the invention.--

Signed and Sealed this
Seventeenth Day of September, 2024

Katherine Kelly Vidal
*Director of the United States Patent and Trademark Office*